US011246638B2

(12) United States Patent
Bonutti et al.

(10) Patent No.: US 11,246,638 B2
(45) Date of Patent: Feb. 15, 2022

(54) METHODS AND DEVICES FOR UTILIZING BONDABLE MATERIALS

(71) Applicant: P Tech, LLC, Effingham, IL (US)

(72) Inventors: Peter M. Bonutti, Manalapan, FL (US); Matthew J. Cremens, Effingham, IL (US); Justin E Beyers, Effingham, IL (US)

(73) Assignee: P TECH, LLC, Effingham, IL (US)

( * ) Notice: Subject to any disclaimer, the term of this patent is extended or adjusted under 35 U.S.C. 154(b) by 0 days.

(21) Appl. No.: 15/224,823

(22) Filed: Aug. 1, 2016

(65) Prior Publication Data

US 2016/0346025 A1 Dec. 1, 2016

Related U.S. Application Data

(63) Continuation of application No. 12/711,540, filed on Feb. 24, 2010, now Pat. No. 9,439,642, which is a (Continued)

(51) Int. Cl.
*A61B 17/80* (2006.01)
*A61B 17/88* (2006.01)
(Continued)

(52) U.S. Cl.
CPC ...... *A61B 17/8836* (2013.01); *A61B 17/0401* (2013.01); *A61B 17/68* (2013.01);
(Continued)

(58) Field of Classification Search
CPC ........... A61B 17/72–7291; A61B 17/80–8095; A61B 17/84–8695; A61F 2/44–447
See application file for complete search history.

(56) References Cited

U.S. PATENT DOCUMENTS

| 319,296 A | 6/1885 | Molesworth |
|---|---|---|
| 668,878 A | 2/1901 | Jensen |

(Continued)

FOREIGN PATENT DOCUMENTS

| CA | 2641580 | 8/2007 |
|---|---|---|
| CA | 2680827 | 9/2008 |

(Continued)

OTHER PUBLICATIONS

Enabling Local Drug Delivery-Implant Device Combination Therapies, Surmodics, Inc., (c) 2003.
(Continued)

*Primary Examiner* — Eduardo C Robert
*Assistant Examiner* — Steven J Cotroneo
(74) *Attorney, Agent, or Firm* — Stinson LLP

(57) ABSTRACT

The invention primarily relates to fastening and stabilizing tissues, implants, and/or bondable materials, such as the fastening of a tissue and/or implant to a bondable material, the fastening of an implant to tissue, and/or the fastening of an implant to another implant. This may involve using an energy source to bond and/or mechanically to stabilize a tissue, an implant, a bondable material, and/or other biocompatible material. The invention may also relate to the use of an energy source to remove and/or install an implant and/or bondable material or to facilitate solidification and/or polymerization of bondable material.

20 Claims, 34 Drawing Sheets

Related U.S. Application Data continuation-in-part of application No. 12/202,210, filed on Aug. 28, 2008, now Pat. No. 8,496,657, and a continuation-in-part of application No. 11/689,670, filed on Mar. 22, 2007, now Pat. No. 9,610,073, and a continuation-in-part of application No. 11/671,556, filed on Feb. 26, 2007, now Pat. No. 9,421,005, and a continuation-in-part of application No. 11/416,618, filed on May 3, 2006, now Pat. No. 7,967,820.

(60) Provisional application No. 61/155,133, filed on Feb. 24, 2009.

(51) Int. Cl.

| | | |
|---|---|---|
| *A61B 17/68* | (2006.01) | |
| *A61B 17/70* | (2006.01) | |
| *A61B 17/72* | (2006.01) | |
| *A61B 17/86* | (2006.01) | |
| *A61F 2/30* | (2006.01) | |
| *A61F 2/46* | (2006.01) | |
| *A61L 24/00* | (2006.01) | |
| *A61L 24/04* | (2006.01) | |
| *A61B 17/04* | (2006.01) | |
| *A61B 17/32* | (2006.01) | |
| *A61B 17/11* | (2006.01) | |
| *A61B 17/00* | (2006.01) | |
| *A61F 2/08* | (2006.01) | |
| *A61F 2/32* | (2006.01) | |
| *A61F 2/34* | (2006.01) | |
| *A61F 2/36* | (2006.01) | |
| *A61F 2/38* | (2006.01) | |
| *A61F 2/40* | (2006.01) | |
| *A61F 2/42* | (2006.01) | |
| *A61F 2/44* | (2006.01) | |
| *A61F 2/06* | (2013.01) | |
| *A61F 2/28* | (2006.01) | |

(52) U.S. Cl.
CPC ...... *A61B 17/7059* (2013.01); *A61B 17/7233* (2013.01); *A61B 17/7266* (2013.01); *A61B 17/866* (2013.01); *A61B 17/8685* (2013.01); *A61B 17/88* (2013.01); *A61B 17/8872* (2013.01); *A61F 2/30* (2013.01); *A61F 2/46* (2013.01); *A61L 24/001* (2013.01); *A61L 24/046* (2013.01); *A61B 17/11* (2013.01); *A61B 17/1128* (2013.01); *A61B 17/1146* (2013.01); *A61B 2017/005* (2013.01); *A61B 2017/044* (2013.01); *A61B 2017/0409* (2013.01); *A61B 2017/1107* (2013.01); *A61B 2017/32007* (2017.08); *A61F 2/0811* (2013.01); *A61F 2/3094* (2013.01); *A61F 2/30721* (2013.01); *A61F 2/30756* (2013.01); *A61F 2/32* (2013.01); *A61F 2/34* (2013.01); *A61F 2/36* (2013.01); *A61F 2/3603* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4081* (2013.01); *A61F 2/4202* (2013.01); *A61F 2/44* (2013.01); *A61F 2/4455* (2013.01); *A61F 2/468* (2013.01); *A61F 2002/067* (2013.01); *A61F 2002/2817* (2013.01); *A61F 2002/30062* (2013.01); *A61F 2002/30065* (2013.01); *A61F 2002/30067* (2013.01); *A61F 2002/3068* (2013.01); *A61F 2002/30133* (2013.01); *A61F 2002/30451* (2013.01); *A61F 2002/30576* (2013.01); *A61F 2002/30604* (2013.01); *A61F 2002/30677* (2013.01); *A61F 2002/30785* (2013.01); *A61F 2002/30787* (2013.01); *A61F 2002/30878* (2013.01); *A61F 2002/30892* (2013.01); *A61F 2002/30894* (2013.01); *A61F 2002/30971* (2013.01); *A61F 2002/30973* (2013.01); *A61F 2002/3401* (2013.01); *A61F 2002/3403* (2013.01); *A61F 2002/444* (2013.01); *A61F 2002/4619* (2013.01); *A61F 2002/4683* (2013.01); *A61F 2210/0004* (2013.01); *A61F 2210/0071* (2013.01); *A61F 2220/0058* (2013.01); *A61F 2230/0015* (2013.01); *A61F 2250/0068* (2013.01); *A61F 2310/00011* (2013.01); *A61F 2310/00365* (2013.01); *A61F 2310/00383* (2013.01); *A61F 2310/00952* (2013.01)

(56) References Cited

U.S. PATENT DOCUMENTS

| | | | |
|---|---|---|---|
| 668,879 | A | 2/1901 | Miller |
| 702,789 | A | 6/1902 | Gibson |
| 862,712 | A | 8/1907 | Collins |
| 2,121,193 | A | 12/1932 | Hanicke |
| 2,187,852 | A | 8/1936 | Friddle |
| 2,178,840 | A | 11/1936 | Lorenian |
| 2,199,025 | A | 4/1940 | Conn |
| 2,235,419 | A | 3/1941 | Callahan |
| 2,248,054 | A | 7/1941 | Becker |
| 2,270,188 | A | 1/1942 | Longfellow |
| 2,518,276 | A | 8/1950 | Braward |
| 2,557,669 | A | 6/1951 | Lloyd |
| 2,566,499 | A | 9/1951 | Richter |
| 2,621,653 | A | 12/1952 | Briggs |
| 2,725,053 | A | 11/1955 | Bambara |
| 2,830,587 | A | 4/1958 | Everett |
| 3,204,635 | A | 9/1965 | Voss |
| 3,347,234 | A | 10/1967 | Voss |
| 3,367,809 | A | 2/1968 | Soloff |
| 3,391,690 | A | 7/1968 | Armao |
| 3,477,429 | A | 11/1969 | Sampson |
| 3,513,848 | A | 5/1970 | Winston |
| 3,518,993 | A | 7/1970 | Blake |
| 3,577,991 | A | 5/1971 | Wilkinson |
| 3,596,292 | A | 8/1971 | Erb |
| 3,608,539 | A | 9/1971 | Miller |
| 3,625,220 | A | 12/1971 | Engelsher |
| 3,648,705 | A | 3/1972 | Lary |
| 3,653,388 | A | 4/1972 | Tenckhoff |
| 3,656,476 | A | 4/1972 | Swinney |
| 3,657,056 | A | 4/1972 | Winston |
| 3,678,980 | A | 7/1972 | Putshall |
| 3,709,218 | A * | 1/1973 | Halloran ............... A61B 17/72 606/64 |
| 3,711,347 | A | 1/1973 | Wagner |
| 3,760,808 | A | 9/1973 | Pleuer |
| 3,788,318 | A | 1/1974 | Kim |
| 3,789,852 | A | 2/1974 | Kim |
| 3,802,438 | A | 4/1974 | Wolvek |
| 3,807,394 | A | 4/1974 | Attenborough |
| 3,809,075 | A | 5/1974 | Matles |
| 3,811,449 | A | 5/1974 | Pravlee |
| 3,825,010 | A | 7/1974 | McDonald |
| 3,833,003 | A | 9/1974 | Taricco |
| 3,835,849 | A | 9/1974 | McGuire |
| 3,842,824 | A | 10/1974 | Neurfeld |
| 3,857,396 | A | 12/1974 | Hardwick |
| 3,867,932 | A | 2/1975 | Huene |
| 3,875,652 | A | 4/1975 | Arnold |
| 3,888,405 | A | 6/1975 | Jones et al. |
| 3,898,992 | A | 8/1975 | Balamuth |
| 3,918,442 | A | 11/1975 | Nikolaev |
| 3,968,800 | A | 7/1976 | Vilasi |
| 4,023,559 | A | 5/1977 | Gaskell |
| 4,064,566 | A | 12/1977 | Fletcher |
| 4,089,071 | A | 5/1978 | Kainberz |

(56) References Cited

U.S. PATENT DOCUMENTS

| | | | |
|---|---|---|---|
| 4,156,574 A | 5/1979 | Boben |
| 4,164,794 A | 8/1979 | Spector |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu |
| 4,257,411 A | 3/1981 | Cho |
| 4,265,231 A | 5/1981 | Scheller |
| 4,281,649 A * | 8/1981 | Derweduwen ..... A61B 17/1725 606/64 |
| 4,291,698 A | 9/1981 | Fuchs |
| 4,309,488 A | 1/1982 | Heide |
| 4,320,762 A | 3/1982 | Bentov |
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | Charlson |
| 4,437,191 A | 3/1984 | Van Der Zel |
| 4,437,362 A | 3/1984 | Hurst |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | D'Holla |
| 4,535,772 A | 8/1985 | Sheehan |
| 4,547,327 A | 10/1985 | Bruins |
| 4,556,350 A | 12/1985 | Bernhardt |
| 4,566,138 A | 1/1986 | Lewis |
| 4,589,868 A | 5/1986 | Dretler |
| 4,590,928 A | 5/1986 | Hunt |
| 4,597,379 A | 7/1986 | Kihn |
| 4,599,085 A | 7/1986 | Riess |
| 4,601,893 A | 7/1986 | Cardinal |
| 4,606,335 A | 8/1986 | Nedeen |
| 4,621,640 A | 11/1986 | Mulhollan |
| 4,630,609 A | 12/1986 | Chin |
| 4,632,101 A | 12/1986 | Freedland |
| 4,645,503 A | 2/1987 | Lin |
| 4,653,487 A | 3/1987 | Maale |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,685,458 A | 8/1987 | Leckrone |
| 4,691,741 A | 9/1987 | Affa et al. |
| 4,705,040 A | 11/1987 | Mueller |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |
| 4,768,507 A | 9/1988 | Fischell |
| 4,772,286 A | 9/1988 | Goble |
| 4,773,406 A | 9/1988 | Spector et al. |
| 4,766,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hiavacek |
| 4,817,591 A | 4/1989 | Klaue |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill |
| 4,899,744 A | 2/1990 | Fujitsuka |
| 4,901,721 A | 2/1990 | Hakki |
| 4,911,718 A | 3/1990 | Lee et al. |
| 4,919,194 A | 4/1990 | Gery et al. |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green |
| 4,935,026 A | 6/1990 | Drews |
| 4,935,028 A | 6/1990 | Drews |
| 4,945,625 A | 8/1990 | Winston |
| 4,946,468 A | 8/1990 | Libarid |
| 4,954,126 A | 9/1990 | Wallsten |
| 4,955,910 A | 9/1990 | Bolesky |
| 4,957,498 A | 9/1990 | Caspari |
| 4,961,741 A | 10/1990 | Hayhurst |
| 4,963,151 A | 10/1990 | Ducheyne |
| 4,966,583 A | 10/1990 | Debbas |
| 4,968,315 A | 11/1990 | Gattuma |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,046,513 A | 6/1991 | Gattuma |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,114 A * | 8/1991 | Chapman ............... A61B 17/72 606/286 |
| 5,041,129 A | 8/1991 | Hayhurst |
| 5,047,055 A | 9/1991 | Bao |
| 5,051,049 A | 9/1991 | Wills |
| 5,053,046 A | 10/1991 | Janese |
| 5,053,047 A | 10/1991 | Kuslich |
| 5,059,193 A | 10/1991 | Kuslich |
| 5,059,260 A | 10/1991 | Winters |
| 5,061,274 A | 10/1991 | Kensey |
| 5,061,286 A | 10/1991 | Lyle |
| 5,069,674 A | 12/1991 | Fearnot |
| 5,078,744 A | 1/1992 | Hayhurst |
| 5,078,745 A | 1/1992 | Rhenter |
| 5,084,050 A | 1/1992 | Draenert |

(56) References Cited

U.S. PATENT DOCUMENTS

| | | |
|---|---|---|
| 5,084,051 A | 1/1992 | Tormala |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Derier |
| 5,102,417 A | 4/1992 | Palmaz |
| 5,102,421 A | 4/1992 | Anspach |
| 5,108,399 A | 4/1992 | Eitenmuller |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,493 A | 6/1993 | Raad |
| 5,219,359 A | 6/1993 | McQuilkin |
| 5,226,899 A | 7/1993 | Lee |
| 5,234,006 A | 8/1993 | Eaton |
| 5,234,425 A | 8/1993 | Fogarty |
| 5,236,438 A | 8/1993 | Wilk |
| 5,236,445 A | 8/1993 | Hayhurst |
| 5,242,902 A | 9/1993 | Murphy |
| 5,254,113 A | 10/1993 | Wilk |
| 5,258,007 A | 11/1993 | Spetzler |
| 5,258,015 A | 11/1993 | Li |
| 5,258,016 A | 11/1993 | Dipoto |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Habermeyer |
| 5,282,832 A | 2/1994 | Toso |
| 5,290,281 A * | 3/1994 | Tschakaloff ....... A61B 17/8085 219/229 |
| 5,304,119 A | 4/1994 | Balaban |
| 5,306,280 A | 4/1994 | Bregen |
| 5,306,301 A | 4/1994 | Graf |
| 5,306,309 A | 4/1994 | Wagner et al. |
| 5,315,741 A | 5/1994 | Dubberke |
| 5,318,570 A | 6/1994 | Hood |
| 5,318,588 A | 6/1994 | Horzewski |
| 5,320,611 A | 6/1994 | Bonutti |
| 5,324,308 A | 6/1994 | Pierce |
| 5,328,480 A | 7/1994 | Melker |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot |
| 5,330,486 A | 7/1994 | Wilkinson |
| 5,336,231 A | 8/1994 | Adair |
| 5,336,240 A | 8/1994 | Metzler |
| 5,339,799 A | 8/1994 | Kami |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,366,480 A | 11/1994 | Corriveaau |
| 5,370,646 A | 12/1994 | Reese |
| 5,370,660 A | 12/1994 | Weinstein |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,173 A | 2/1995 | Wilk |
| 5,395,308 A | 3/1995 | Fox |
| 5,397,311 A | 3/1995 | Walker |
| 5,400,805 A | 3/1995 | Warren |
| 5,403,312 A | 4/1995 | Yates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Skikhman |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr |
| 5,447,503 A | 9/1995 | Miller |
| 5,449,372 A | 9/1995 | Schmaltz |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donnell |
| 5,464,426 A | 11/1995 | Bonutti |
| 5,464,427 A | 11/1995 | Curtis |
| 5,470,337 A | 11/1995 | Moss |
| 5,472,444 A | 12/1995 | Huebner |
| 5,474,554 A | 12/1995 | Ku |
| 5,478,351 A | 12/1995 | Meade |
| 5,478,353 A | 12/1995 | Yoon |
| 5,480,403 A | 1/1996 | Lee |
| 5,486,197 A | 1/1996 | Le |
| 5,487,844 A | 1/1996 | Fujita |
| 5,488,958 A | 2/1996 | Topel |
| 5,496,292 A | 3/1996 | Burnham |
| 5,496,335 A | 3/1996 | Thomason |
| 5,496,348 A | 3/1996 | Bonutti |
| 5,499,382 A | 3/1996 | Nusinov et al. |
| 5,500,000 A | 3/1996 | Feagin |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,522,844 A | 6/1996 | Johnson |
| 5,522,845 A | 6/1996 | Wenstrom |
| 5,522,846 A | 6/1996 | Bonutti |
| 5,527,341 A | 6/1996 | Gogolewski |
| 5,527,342 A | 6/1996 | Pietrzak |
| 5,527,343 A | 6/1996 | Bonutti |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,718 A | 7/1996 | Bartlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin |

(56) References Cited

U.S. PATENT DOCUMENTS

| | | |
|---|---|---|
| 5,569,305 A | 10/1996 | Bonutti |
| 5,569,306 A | 10/1996 | Thal |
| 5,571,190 A | 11/1996 | Ulrich et al. |
| 5,573,517 A | 11/1996 | Bonutti |
| 5,573,538 A | 11/1996 | Laboureau |
| 5,573,542 A | 11/1996 | Stevens |
| 5,575,801 A | 11/1996 | Habermeyer |
| 5,580,344 A | 12/1996 | Hasson |
| 5,584,835 A | 12/1996 | Greenfield |
| 5,584,860 A | 12/1996 | Goble |
| 5,584,862 A | 12/1996 | Bonutti |
| 5,591,206 A | 1/1997 | Moufarrege |
| 5,593,422 A | 1/1997 | Moufarrege |
| 5,593,425 A | 1/1997 | Bonutti |
| 5,593,625 A | 1/1997 | Riebel |
| 5,601,557 A | 2/1997 | Hayhurst |
| 5,601,558 A | 2/1997 | Torrie |
| 5,601,595 A | 2/1997 | Schwartz |
| 5,607,427 A | 3/1997 | Tschakaloff |
| 5,609,595 A | 3/1997 | Jennig |
| 5,618,314 A | 4/1997 | Harwin |
| 5,620,461 A | 4/1997 | Muijs Van De Moer |
| 5,626,612 A | 5/1997 | Bartlett |
| 5,626,614 A | 5/1997 | Hart |
| 5,626,718 A | 5/1997 | Philippe |
| 5,628,751 A | 5/1997 | Sander |
| 5,630,824 A | 5/1997 | Hart |
| 5,634,926 A | 6/1997 | Jobe |
| 5,635,784 A | 6/1997 | Seale |
| 5,643,274 A | 7/1997 | Sander |
| 5,643,293 A | 7/1997 | Kogasaka |
| 5,643,295 A | 7/1997 | Yoon |
| 5,643,321 A | 7/1997 | McDevitt |
| 5,645,553 A | 7/1997 | Kolesa |
| 5,645,597 A | 7/1997 | Krapiva |
| 5,645,599 A | 7/1997 | Samani |
| 5,649,955 A | 7/1997 | Hashimoto |
| 5,649,963 A | 7/1997 | McDevitt |
| 5,651,377 A | 7/1997 | O'Donnell |
| 5,658,313 A | 8/1997 | Thal |
| 5,660,225 A | 8/1997 | Saffran |
| 5,662,658 A | 9/1997 | Wenstrom |
| 5,665,089 A | 9/1997 | Dall |
| 5,665,109 A | 9/1997 | Yoon |
| 5,667,513 A | 9/1997 | Torrie |
| 5,669,917 A | 9/1997 | Sauer |
| 5,674,240 A | 10/1997 | Bonutti |
| 5,681,310 A | 10/1997 | Yuan |
| 5,681,333 A | 10/1997 | Burkhart |
| 5,681,351 A | 10/1997 | Jamiolkowski |
| 5,681,352 A | 10/1997 | Clancy |
| 5,685,820 A | 11/1997 | Riek |
| 5,688,283 A | 11/1997 | Knapp |
| 5,690,654 A | 11/1997 | Ovil |
| 5,690,655 A | 11/1997 | Hart |
| 5,690,676 A | 11/1997 | Dipoto |
| 5,693,055 A | 12/1997 | Zahiri |
| 5,697,950 A | 12/1997 | Fucci |
| 5,702,397 A | 12/1997 | Gonie |
| 5,702,462 A | 12/1997 | Oberlander |
| 5,707,395 A | 1/1998 | Li |
| 5,713,903 A | 2/1998 | Sander |
| 5,713,921 A | 2/1998 | Bonutti |
| 5,718,717 A | 2/1998 | Bonutti |
| 5,720,747 A | 2/1998 | Burke |
| 5,725,541 A | 3/1998 | Anspach |
| 5,725,556 A | 3/1998 | Moser |
| 5,725,582 A | 3/1998 | Bevan |
| 5,730,747 A | 3/1998 | Ek |
| 5,733,306 A | 3/1998 | Bonutti |
| 5,720,753 A | 4/1998 | Sander |
| 5,735,875 A | 4/1998 | Bonutti |
| 5,735,877 A | 4/1998 | Pagedas |
| 5,735,899 A | 4/1998 | Schwartz |
| 5,741,282 A | 4/1998 | Anspach |
| 5,752,952 A | 5/1998 | Adamson |
| 5,752,974 A | 5/1998 | Rhee |
| 5,755,809 A | 5/1998 | Cohen |
| 5,762,458 A | 6/1998 | Wang |
| 5,766,221 A | 6/1998 | Benderev |
| 5,769,894 A | 6/1998 | Ferragamo |
| 5,772,672 A | 6/1998 | Toy |
| 5,776,151 A | 7/1998 | Chan |
| 5,779,706 A * | 7/1998 | Tschakaloff ....... A61B 17/8085 219/229 |
| 5,782,862 A | 7/1998 | Bonutti |
| 5,785,713 A | 7/1998 | Jobe |
| 5,792,096 A | 8/1998 | Rentmeester |
| 5,797,931 A | 8/1998 | Bito |
| 5,800,537 A | 9/1998 | Bell |
| 5,807,403 A | 9/1998 | Beyar |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey |
| 5,824,009 A | 10/1998 | Fukuda |
| 5,830,125 A | 11/1998 | Scribner |
| 5,836,897 A | 11/1998 | Sakural |
| 5,839,899 A | 11/1998 | Robinson |
| 5,843,178 A | 12/1998 | Vanney |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan |
| 5,897,574 A | 4/1999 | Bonutti |
| 5,899,911 A | 5/1999 | Carter |
| 5,899,921 A | 5/1999 | Caspari |
| 5,906,579 A | 5/1999 | Salm |
| 5,906,625 A | 5/1999 | Bito |
| 5,908,429 A | 6/1999 | Yoon |
| 5,911,721 A | 6/1999 | Nicholson |
| 5,918,604 A | 7/1999 | Whelan |
| 5,919,193 A | 7/1999 | Slavitt |
| 5,919,208 A | 7/1999 | Valenti |
| 5,919,215 A | 7/1999 | Wiklund |
| 5,921,986 A | 7/1999 | Bonutti |
| 5,925,064 A | 7/1999 | Meyers |
| 5,928,244 A | 7/1999 | Tovey |
| 5,928,267 A | 7/1999 | Bonutti |
| 5,931,838 A | 8/1999 | Vito |
| 5,931,869 A | 8/1999 | Boucher |
| 5,940,942 A | 8/1999 | Fong |
| 5,941,900 A | 8/1999 | Bonutti |
| 5,945,002 A | 9/1999 | Bonutti |
| 5,947,982 A | 9/1999 | Duran |
| 5,948,000 A | 9/1999 | Larsen |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | Dipoto |
| 5,961,499 A | 10/1999 | Bonutti |
| 5,961,521 A | 10/1999 | Roger |
| 5,961,554 A | 10/1999 | Janson |
| 5,964,765 A | 10/1999 | Fenton |
| 5,964,769 A | 10/1999 | Wagner |
| 5,968,046 A | 10/1999 | Castleman |
| 5,968,047 A | 10/1999 | Reed |
| 5,980,520 A | 11/1999 | Vacaillie |
| 5,980,559 A | 11/1999 | Bonutti |
| 5,984,929 A | 11/1999 | Bashiri |
| 5,989,282 A | 11/1999 | Bonutti |
| 5,993,458 A | 11/1999 | Vaitekunas |
| 5,993,477 A | 11/1999 | Vaitekunas |
| 6,007,567 A | 12/1999 | Bonutti |
| 6,007,580 A | 12/1999 | Lehto |

(56) References Cited

U.S. PATENT DOCUMENTS

| | | | |
|---|---|---|---|
| 6,010,525 A | 1/2000 | Bonutti | |
| 6,010,526 A | 1/2000 | Sandstrom | |
| 6,017,321 A | 1/2000 | Boone | |
| 6,033,429 A | 3/2000 | Magovern | |
| 6,033,430 A | 3/2000 | Bonutti | |
| 6,045,551 A | 4/2000 | Bonutti | |
| 6,050,998 A | 4/2000 | Fletcher | |
| 6,056,751 A * | 5/2000 | Fenton, Jr. | A61B 17/0401 606/151 |
| 6,056,772 A | 5/2000 | Bonutti | |
| 6,056,773 A | 5/2000 | Bonutti | |
| 6,059,797 A | 5/2000 | Mears | |
| 6,059,817 A | 5/2000 | Bonutti | |
| 6,059,827 A | 5/2000 | Fenton | |
| 6,063,095 A | 5/2000 | Wang | |
| 6,066,151 A | 5/2000 | Miyawaki | |
| 6,066,160 A | 5/2000 | Colvin | |
| 6,066,166 A | 5/2000 | Bischoff | |
| 6,068,637 A | 5/2000 | Popov | |
| 6,077,277 A | 6/2000 | Mollenauer | |
| 6,077,292 A | 6/2000 | Bonutti | |
| 6,080,161 A * | 6/2000 | Eaves, III | A61B 17/68 606/329 |
| 6,083,522 A | 7/2000 | Chu | |
| 6,086,593 A | 7/2000 | Bonutti | |
| 6,086,608 A | 7/2000 | Ek | |
| 6,090,072 A | 7/2000 | Kratoska | |
| 6,099,531 A | 8/2000 | Bonutti | |
| 6,099,537 A | 8/2000 | Sugai | |
| 6,099,550 A | 8/2000 | Yoon | |
| 6,099,552 A | 8/2000 | Adams | |
| 6,102,850 A | 8/2000 | Wang | |
| 6,106,545 A | 8/2000 | Egan | |
| 6,117,160 A | 9/2000 | Bonutti | |
| 6,120,536 A | 9/2000 | Ding | |
| 6,125,574 A | 10/2000 | Ganaja | |
| 6,126,677 A | 10/2000 | Ganaja | |
| 6,139,320 A | 10/2000 | Hahn | |
| RE36,974 E | 11/2000 | Bonutti | |
| 6,149,669 A | 11/2000 | Li | |
| 6,152,949 A | 11/2000 | Bonutti | |
| 6,155,756 A | 12/2000 | Mericle | |
| 6,159,224 A | 12/2000 | Yoon | |
| 6,159,234 A | 12/2000 | Bonutti | |
| 6,171,307 B1 | 1/2001 | Orlich | |
| 6,174,324 B1 | 1/2001 | Egan | |
| 6,179,840 B1 | 1/2001 | Bowman | |
| 6,179,850 B1 | 1/2001 | Goradia | |
| 6,187,008 B1 | 2/2001 | Hamman | |
| 6,190,400 B1 | 2/2001 | Van De Moer | |
| 6,190,401 B1 | 2/2001 | Green | |
| 6,200,322 B1 | 3/2001 | Branch | |
| 6,214,049 B1 | 4/2001 | Gayer et al. | |
| 6,217,591 B1 | 4/2001 | Egan | |
| 6,224,593 B1 | 5/2001 | Ryan | |
| 6,224,630 B1 | 5/2001 | Bao | |
| 6,228,086 B1 | 5/2001 | Wahl | |
| 6,231,592 B1 | 5/2001 | Bonutti | |
| 6,238,395 B1 | 5/2001 | Bonutti | |
| 6,238,396 B1 | 5/2001 | Lombardo | |
| 6,258,091 B1 | 7/2001 | Sevrain | |
| 6,264,675 B1 | 7/2001 | Brotz | |
| 6,267,761 B1 | 7/2001 | Ryan | |
| 6,273,717 B1 | 8/2001 | Hahn | |
| 6,280,474 B1 | 8/2001 | Cassidy | |
| 6,286,746 B1 | 9/2001 | Egan | |
| 6,287,325 B1 | 9/2001 | Bonutti | |
| 6,293,961 B2 | 9/2001 | Schwartz | |
| 6,306,159 B1 | 10/2001 | Schwartz | |
| 6,309,405 B1 | 10/2001 | Bonutti | |
| 6,312,448 B1 | 11/2001 | Bonutti | |
| 6,338,730 B1 | 1/2002 | Bonutti | |
| 6,340,365 B2 | 1/2002 | Dittrich | |
| 6,348,056 B1 | 2/2002 | Bates | |
| 6,358,271 B1 | 3/2002 | Egan | |
| 6,364,897 B1 | 4/2002 | Bonutti | |
| 6,368,325 B1 | 4/2002 | McKinley | |
| 6,368,343 B1 | 4/2002 | Bonutti | |
| 6,371,957 B1 | 4/2002 | Amrein | |
| 6,409,742 B1 | 6/2002 | Fulton | |
| 6,409,768 B1 | 6/2002 | Tepic et al. | |
| 6,419,704 B1 | 7/2002 | Ferree | |
| 6,423,088 B1 | 7/2002 | Fenton | |
| 6,425,919 B1 | 7/2002 | Lambrecht | |
| 6,428,562 B2 | 8/2002 | Bonutti | |
| 6,432,115 B1 | 8/2002 | Mollenauer | |
| 6,447,516 B1 | 9/2002 | Bonutti | |
| 6,450,985 B1 | 9/2002 | Schoelling | |
| 6,461,360 B1 | 10/2002 | Adams | |
| 6,475,230 B1 | 11/2002 | Bonutti | |
| 6,488,196 B1 | 12/2002 | Fenton | |
| 6,500,195 B2 | 12/2002 | Bonutti | |
| 6,503,259 B2 | 1/2003 | Huxel | |
| 6,530,933 B1 | 3/2003 | Yeung | |
| 6,535,764 B2 | 3/2003 | Imran | |
| 6,544,267 B1 | 4/2003 | Cole | |
| 6,545,390 B1 | 4/2003 | Hahn | |
| 6,547,792 B1 | 4/2003 | Tsuji | |
| 6,551,304 B1 | 4/2003 | Whalen | |
| 6,554,852 B1 | 4/2003 | Oberlander | |
| 6,527,774 B2 | 5/2003 | Lieberman | |
| 6,558,390 B2 | 5/2003 | Cragg | |
| 6,568,313 B2 | 5/2003 | Fukui | |
| 6,569,187 B1 | 5/2003 | Bonutti | |
| 6,572,635 B1 | 6/2003 | Bonutti | |
| D477,776 S | 7/2003 | Pontaoe | |
| 6,557,426 B2 | 7/2003 | Reinemann | |
| 6,585,750 B2 | 7/2003 | Bonutti | |
| 6,585,764 B2 | 7/2003 | Wright | |
| 6,592,609 B1 | 7/2003 | Bonutti | |
| 6,594,517 B1 | 7/2003 | Nevo | |
| 6,605,090 B1 * | 8/2003 | Trieu | A61B 17/8042 606/281 |
| 6,610,080 B2 | 8/2003 | Morgan | |
| 6,618,910 B1 | 9/2003 | Pontaoe | |
| 6,623,486 B1 | 9/2003 | Weaver | |
| 6,623,487 B1 * | 9/2003 | Goshert | A61B 17/68 606/329 |
| 6,626,944 B1 | 9/2003 | Taylor | |
| 6,632,245 B2 | 10/2003 | Kim | |
| 6,635,073 B2 | 10/2003 | Bonutti | |
| 6,638,279 B2 | 10/2003 | Bonutti | |
| 6,641,592 B1 | 11/2003 | Sauer | |
| 6,645,227 B2 | 11/2003 | Fallin | |
| 6,652,585 B2 * | 11/2003 | Lange | A61B 17/7059 606/29 |
| 6,666,877 B2 | 12/2003 | Morgan | |
| 6,669,705 B2 | 12/2003 | Westhaver | |
| 6,679,888 B2 | 1/2004 | Green | |
| 6,685,750 B1 | 2/2004 | Plos | |
| 6,699,240 B2 | 3/2004 | Francischelli | |
| 6,702,821 B2 | 3/2004 | Bonutti | |
| 6,705,179 B1 | 3/2004 | Mohtasham | |
| 6,709,436 B1 * | 3/2004 | Hover | A61B 17/72 606/62 |
| 6,709,457 B1 | 3/2004 | Otte | |
| 6,719,765 B2 | 4/2004 | Bonutti | |
| 6,719,797 B1 | 4/2004 | Ferree | |
| 6,722,552 B2 | 4/2004 | Fenton | |
| 6,733,531 B1 | 5/2004 | Trieu | |
| 6,764,514 B1 | 7/2004 | Li | |
| 6,770,078 B2 | 8/2004 | Bonutti | |
| 6,780,198 B1 | 8/2004 | Gregoire | |
| 6,786,989 B2 | 9/2004 | Torriani | |
| 6,796,003 B1 | 9/2004 | Marvel | |
| 6,818,010 B2 | 11/2004 | Eichhorn | |
| 6,823,871 B2 | 11/2004 | Schmieding | |
| 6,860,885 B2 | 3/2005 | Bonutti | |
| 6,878,167 B2 | 4/2005 | Ferree | |
| 6,890,334 B2 | 5/2005 | Fenton | |
| 6,899,722 B2 | 5/2005 | Bonutti | |
| 6,913,666 B1 | 7/2005 | Aeschlimann | |
| 6,916,321 B2 | 7/2005 | TenHuisen | |
| 6,921,264 B2 | 7/2005 | Mayer | |

(56) References Cited

U.S. PATENT DOCUMENTS

| | | |
|---|---|---|
| 6,923,824 B2 | 8/2005 | Morgan |
| 6,932,835 B2 | 8/2005 | Bonutti |
| 6,942,684 B2 | 9/2005 | Bonutti |
| 6,944,111 B2 | 9/2005 | Nakamura |
| 6,955,540 B2 | 10/2005 | Mayer |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer |
| 7,018,380 B2 | 3/2006 | Dole |
| 7,033,379 B2 | 4/2006 | Jeterson |
| 7,048,755 B2 | 5/2006 | Bonutti |
| 7,066,960 B1 | 6/2006 | Dickman |
| 7,087,073 B2 | 8/2006 | Bonutti |
| 7,094,251 B2 | 8/2006 | Bonutti |
| 7,104,996 B2 | 9/2006 | Bonutti |
| 7,128,761 B2 | 10/2006 | Kuras et al. |
| 7,128,763 B1 | 10/2006 | Blatt |
| 7,147,652 B2 | 12/2006 | Bonutti |
| 7,160,405 B2 | 1/2007 | Aeschlimann |
| 7,179,259 B1* | 2/2007 | Gibbs ............... A61B 17/1753 606/64 |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian |
| 7,250,051 B2 | 7/2007 | Francischelli |
| 7,252,685 B2 | 8/2007 | Bindseil |
| 7,273,497 B2 | 9/2007 | Ferree |
| 7,329,263 B2 | 2/2008 | Bonutti |
| 7,335,205 B2 | 2/2008 | Aeschlimann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2* | 3/2009 | Raterman ........... B05C 11/1042 438/17 |
| 7,632,272 B2 | 12/2009 | Munro et al. |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton |
| 8,147,514 B2 | 4/2012 | Bonutti |
| 8,162,977 B2 | 4/2012 | Bonutti |
| 2001/0002440 A1 | 5/2001 | Bonutti |
| 2001/0009250 A1 | 7/2001 | Herman |
| 2001/0041916 A1 | 11/2001 | Bonutti |
| 2002/0016593 A1 | 2/2002 | Hearn |
| 2002/0016633 A1 | 2/2002 | Lin |
| 2002/0019649 A1 | 2/2002 | Sikora |
| 2002/0026244 A1 | 2/2002 | Trieu |
| 2002/0029083 A1 | 3/2002 | Zucherman |
| 2002/0029084 A1 | 3/2002 | Paul |
| 2002/0045902 A1 | 4/2002 | Bonutti |
| 2002/0062153 A1 | 5/2002 | Paul |
| 2002/0082529 A1 | 6/2002 | Suorsa |
| 2002/0099379 A1 | 7/2002 | Adam |
| 2002/0103495 A1 | 8/2002 | Dole |
| 2002/0120336 A1 | 8/2002 | Santilli |
| 2002/0123750 A1 | 9/2002 | Eisermann |
| 2002/0183762 A1 | 12/2002 | Anderson |
| 2002/0188301 A1 | 12/2002 | Dallara |
| 2003/0009224 A1 | 1/2003 | Kuras |
| 2003/0039196 A1 | 2/2003 | Nakamura |
| 2003/0040758 A1 | 2/2003 | Wang |
| 2003/0065361 A1 | 4/2003 | Dreyfuss |
| 2003/0105474 A1 | 6/2003 | Bonutti |
| 2003/0158582 A1 | 8/2003 | Bonutti |
| 2003/0118518 A1 | 9/2003 | Hahn |
| 2003/0167072 A1 | 9/2003 | Oberlander |
| 2003/0181800 A1 | 9/2003 | Bonutti |
| 2003/0187506 A1 | 10/2003 | Ross et al. |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler |
| 2003/0225438 A1 | 12/2003 | Bonutti |
| 2003/0229361 A1 | 12/2003 | Jackson |
| 2004/0010287 A1 | 1/2004 | Bonutti |
| 2004/0030341 A1* | 2/2004 | Aeschlimann ........ B29C 66/727 606/232 |
| 2004/0034357 A1 | 2/2004 | Beane |
| 2004/0068320 A1 | 4/2004 | Robie et al. |
| 2004/0097939 A1 | 5/2004 | Bonutti |
| 2004/0098050 A1 | 5/2004 | Foerster |
| 2004/0138703 A1 | 7/2004 | Alleyne |
| 2004/0143334 A1 | 7/2004 | Ferree |
| 2004/0167548 A1 | 8/2004 | Bonutti |
| 2004/0220616 A1 | 11/2004 | Bonutti |
| 2004/0225325 A1 | 11/2004 | Bonutti |
| 2004/0225371 A1 | 11/2004 | Roger |
| 2004/0230223 A1 | 11/2004 | Bonutti |
| 2004/0236374 A1 | 11/2004 | Bonutti |
| 2004/0243241 A1 | 12/2004 | Istephanous et al. |
| 2005/0033366 A1 | 2/2005 | Cole |
| 2005/0038514 A1 | 2/2005 | Helm |
| 2005/0043796 A1 | 2/2005 | Grant |
| 2005/0071012 A1 | 3/2005 | Serhan |
| 2005/0085817 A1 | 4/2005 | Ringeisen |
| 2005/0090827 A1 | 4/2005 | Gedebou |
| 2005/0096699 A1 | 5/2005 | Wixey |
| 2005/0113928 A1 | 5/2005 | Cragg |
| 2005/0126680 A1 | 6/2005 | Aeschlimann |
| 2005/0143826 A1 | 6/2005 | Zucherman |
| 2005/0240227 A1 | 6/2005 | Bonutti |
| 2005/0149024 A1 | 7/2005 | Ferrante |
| 2005/0149029 A1 | 7/2005 | Bonutti |
| 2005/0177162 A1 | 8/2005 | McLeod et al. |
| 2005/0203521 A1 | 9/2005 | Bonutti |
| 2005/0216008 A1 | 9/2005 | Zwirnmann et al. |
| 2005/0216059 A1 | 9/2005 | Bonutti |
| 2005/0216087 A1 | 9/2005 | Zucherman |
| 2005/0222620 A1 | 10/2005 | Bonutti |
| 2005/0234019 A1 | 10/2005 | Gall |
| 2005/0246021 A1 | 11/2005 | Ringeisen |
| 2005/0261684 A1 | 11/2005 | Shaolian |
| 2005/0267481 A1 | 12/2005 | Carl |
| 2005/0267534 A1 | 12/2005 | Bonutti |
| 2006/0009855 A1 | 1/2006 | Goble |
| 2006/0015101 A1 | 1/2006 | Warburton |
| 2006/0015108 A1 | 1/2006 | Bonutti |
| 2006/0024357 A1 | 2/2006 | Carpenter |
| 2006/0026244 A1 | 2/2006 | Watson |
| 2006/0064095 A1 | 3/2006 | Senn |
| 2006/0089646 A1 | 4/2006 | Bonutti |
| 2006/0122600 A1 | 6/2006 | Cole |
| 2006/0122704 A1 | 6/2006 | Vresilovic |
| 2006/0142799 A1 | 6/2006 | Bonutti |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0229715 A1 | 10/2006 | Istephanous et al. |
| 2006/0235470 A1 | 10/2006 | Bonutti |
| 2006/0241695 A1 | 10/2006 | Bonutti |
| 2006/0264950 A1* | 11/2006 | Nelson ............... A61B 17/7208 606/916 |
| 2006/0265009 A1 | 11/2006 | Bonutti |
| 2006/0265011 A1 | 11/2006 | Bonutti |
| 2007/0032825 A1 | 2/2007 | Bonutti |
| 2007/0088362 A1 | 4/2007 | Bonutti |
| 2007/0118129 A1* | 5/2007 | Fraser .................... A61F 2/0811 606/71 |
| 2007/0123878 A1* | 5/2007 | Shaver .................... A61B 17/72 606/64 |
| 2007/0198555 A1 | 8/2007 | Friedman |
| 2007/0265561 A1 | 11/2007 | Yeung |
| 2007/0270833 A1 | 11/2007 | Bonutti |

(56) References Cited

U.S. PATENT DOCUMENTS

| | | | |
|---|---|---|---|
| 2008/0021474 A1 | 1/2008 | Bonutti | |
| 2008/0039845 A1 | 2/2008 | Bonutti | |
| 2008/0039873 A1 | 2/2008 | Bonutti | |
| 2008/0046090 A1 | 2/2008 | Paul | |
| 2008/0097448 A1 | 4/2008 | Binder | |
| 2008/0108897 A1 | 5/2008 | Bonutti | |
| 2008/0108916 A1 | 5/2008 | Bonutti | |
| 2008/0114399 A1 | 5/2008 | Bonutti | |
| 2008/0132950 A1* | 6/2008 | Lange | A61B 17/7059 606/246 |
| 2008/0140116 A1 | 6/2008 | Bonutti | |
| 2008/0140117 A1 | 6/2008 | Bonutti | |
| 2008/0195145 A1 | 8/2008 | Bonutti | |
| 2008/0269753 A1* | 10/2008 | Cannestra | A61B 17/7059 606/70 |
| 2008/0269808 A1* | 10/2008 | Gall | A61B 17/7225 606/299 |
| 2009/0024161 A1 | 1/2009 | Bonutti | |
| 2009/0093684 A1 | 4/2009 | Schorer | |
| 2009/0138014 A1 | 5/2009 | Bonutti | |
| 2009/0194969 A1 | 8/2009 | Bearey | |
| 2010/0211120 A1 | 2/2010 | Bonutti | |
| 2011/0060375 A1 | 3/2011 | Bonutti | |
| 2011/0295253 A1 | 12/2011 | Bonutti | |
| 2012/0165841 A1 | 6/2012 | Bonutti | |
| 2012/0191140 A1 | 7/2012 | Bonutti | |
| 2012/0197316 A1 | 8/2012 | Mayer | |
| 2012/0215233 A1 | 8/2012 | Bonutti | |

FOREIGN PATENT DOCUMENTS

| | | |
|---|---|---|
| CA | 2698057 | 3/2009 |
| DE | 1903316 B2 | 10/1964 |
| DE | 3517204 | 11/1986 |
| DE | 3722538 | 1/1989 |
| DE | 9002844 U1 | 1/1991 |
| EP | 0784454 | 5/1996 |
| EP | 0773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 199112779 | 9/1991 |
| WO | 199323094 | 11/1993 |
| WO | 1994008642 | 4/1994 |
| WO | 199516398 | 6/1995 |
| WO | 199531941 | 11/1995 |
| WO | 1996014802 | 11/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2010099222 | 2/2010 |

OTHER PUBLICATIONS

Stent Based Delivery of Sirolimus Reduces Neointimal Formation in a Porcine Coronary Model, Takeshi Suzuki, American Heart Association, Inc. (c) 2001.

Why Tie a Knot When You Can Use Y-Knot48, Innovasive Devices Inc., (c) 1998.

Ask Oxford projection, compact oxford english dicitionary: projection, Mar. 30, 2009.

Ask Oxford projection, compact oxford english dicitionary: slit, Mar. 30, 2009.

Non-Final Office Action dated Jul. 22, 2015 relating to U.S. Appl. No. 12/711,540, 9 pages.

Final Office Action dated Dec. 22, 2014 relating to U.S. Appl. No. 12/711,540, 5 pages.

Non-Final Office Action dated Mar. 11, 2014 relating to U.S. Appl. No. 12/711,540, 12 pages.

Final Office Action dated May 13, 2013 relating to U.S. Appl. No. 12/711,540, 6 pages.

Non-Final Office Action dated Jul. 12, 2012 relating to U.S. Appl. No. 12/711,540, 5 pages.

510k, Modified Mitek 3.5mm Absorbable Suture Anchor System, Jun. 9, 1997, K970896.

510K, Summary for Arthrex Inc.'s Bio-Interference Screw, Sep. 9, 1997, K971358.

510k, Surgicraft Bone Tie, Sep. 25, 1998, K982719.

Karlsson et al, Repair of Bankart lesions with a suture anchor in recurrent dislocation of the shoulder, Scand. j. of Med & Science in Sports, 1995, 5:170-174.

Madjar et al, Minimally Invasive Pervaginam Procedures, for the Treatment of Female Stress Incontinence . . . , Artificial Organs, 22 (10) 879-885, 1998.

Nowak et al, Comparative Study of Fixation Techniques in the Open Bankart Operation Using Either a Cannulated Screw or Suture-Anchors, Acta Orthopcedica Belgica, vol. 64—Feb. 1998.

Packer et al, Repair of Acute Scapho-Lunate Dissociation Facilitated by the "Tag"* Suture Anchor, Journal of Hand Surgery (British and European Volume, 1994) 19B: 5: 563-564.

Richmond, Modificatio of the Bankart reconstruction with a suture anchor, Am J Sports Med, vol. 19, No. 4, p. 343-346, 1991.

Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb. 1998): pp. 118-122.

Tfix, Acufex just tied the knot., Am. J. Sports Med., vol. 22, No. 3, May-Jun. 1994.

Wong et al, Case Report: Proper Insertion Angle is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb. 2010),: pp. 286-290.

Cobb et al, Late Correction of Malunited Intercondylar Humeral Fractures Intra-Articular Osteotomy and Tricortical Bone Grafting, J BoneJointSurg [Br] 1994; 76-B:622-6.

Fellinger, et al, Radial avulsion of the triangular fibrocartilage complex in acute wrist trauma: a new technique for arthroscopic repair, Jun. 1997, Arthroscopy vol. 13 No. 3 p. 370-4.

Hecker et al, Pull-out strength of suture anchors for rotator cuff and Bankart lesion repairs, Nov.-Dec. 1993, The American Journal of Sports Medicine, vol. 21 No. 6 p. 874-9.

Hernigou et al, Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.

Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.

Mosca et al, Calcaneal Lengthening for Valgus Deformity of the Hindfoot: Results in Children Who Had Severe, Symptomatic Flatfoot and Skewfoot, J Bone Joint Surg,, 1195—p. 499-512.

Murphycet al, Radial Opening Wedge Osteotomy in Madelung's Deformity, J. Hand Surg, vol. 21 A No. 6 Nov. 1996, p. 1035-44.

Biomet, Stanmore Modular Hip, J. Bone Joint Surg., vol. 76-B : No. Two, Mar. 1994.

Petition for Inter Partes Review of U.S. Pat. No. 5,980,559, IPR 2013-00603, Filing Date Sep. 24, 2013.

Declaration of David Kaplan, Ph.D. Regarding U.S. Pat. No. 5,980,559, IPR 2013-00603, Sep. 24, 2013.

(56) References Cited

OTHER PUBLICATIONS

Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, For Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740.
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy fhe Journal of Arthroscopic and Related Surgery, Aug. 1996.
Meniscus Replacement with Bone Anchors: A Surgical Technique, Arthroscopy: The Journal of Arcioscopic and Related Surgery, 1994.
Problem Solving Report Question No. 1014984.066, Ultrasonic Welding, (c) 1999.
Dukane Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Arthrex, Protect your graft, Am J Sports Med, vol. 22, No. 4, Jul.-Aug. 1994.
Barrett et al., T-Fix endoscopic meniscal repair technique and approach to different types of tears, Apr. 95, Arthroscopy 2 vol 11 No 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510K, arthrex pushlock, Jun. 29, 2005, K051219.
510K, mitek micro anchor, Nov. 6, 1996, K962511.
510K, Multitak Suture System, Jan. 10, 1997, K964324.
Non-Final Office action for U.S. Appl. No. 15/436,168, dated Jun. 4, 2018, 12 pages.
Textured Surface Technology, Branson Technolog, Branson Ultrasonics Corp., (c) 1992.

\* cited by examiner

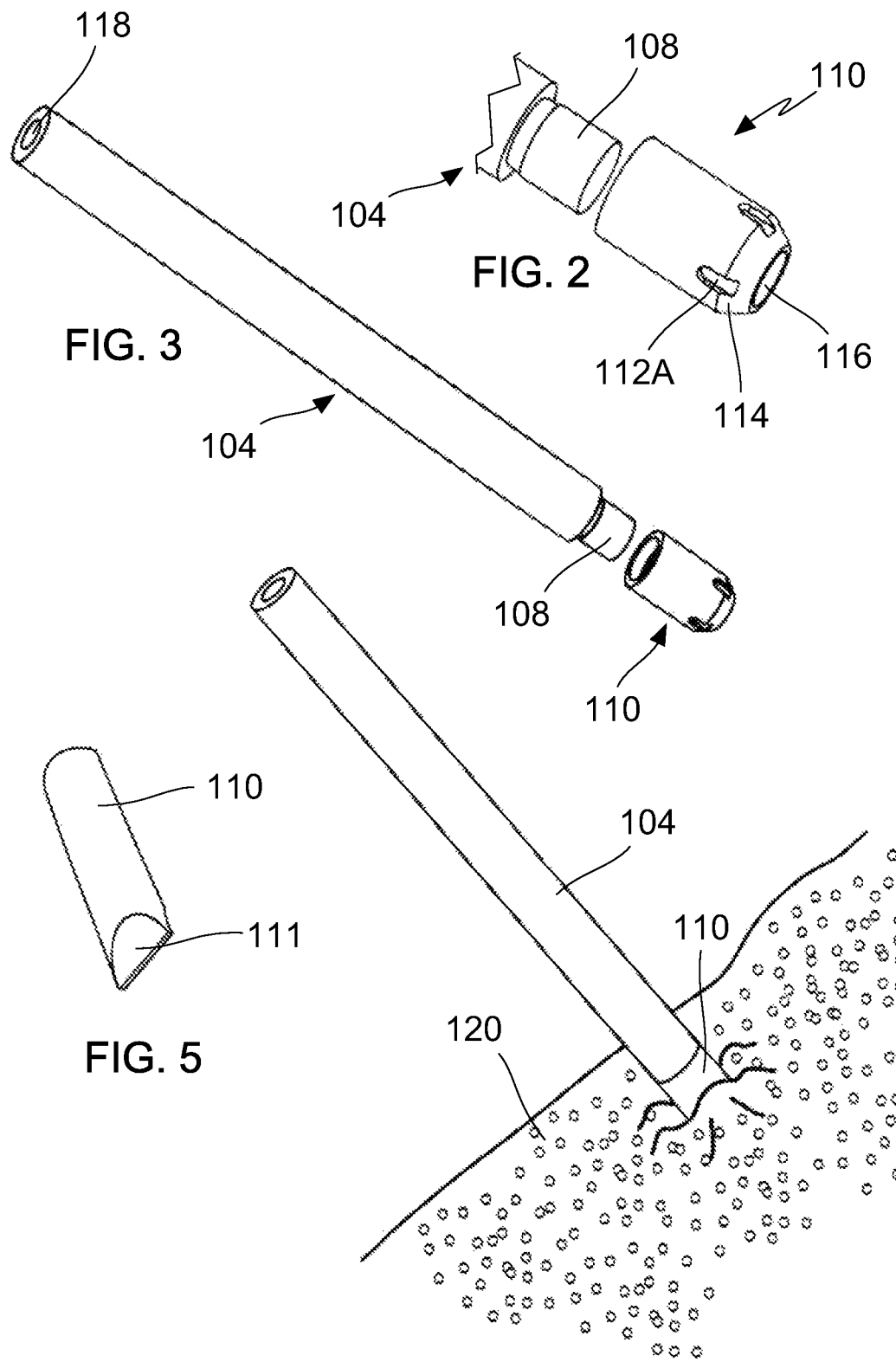

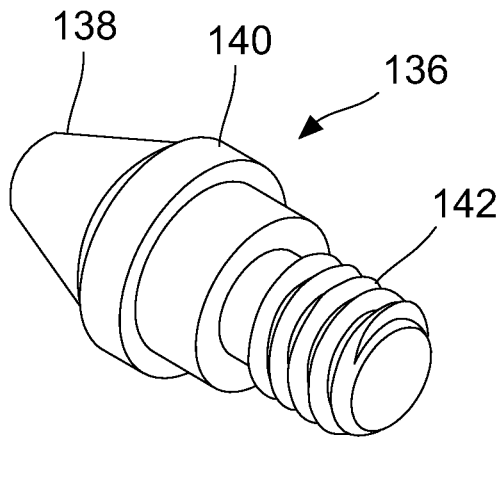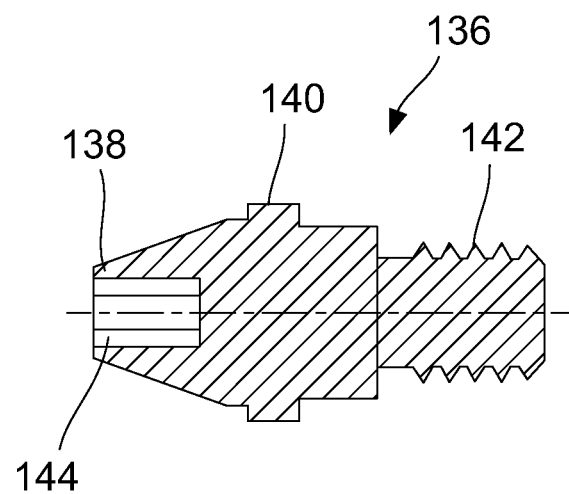
FIG. 11                FIG. 12
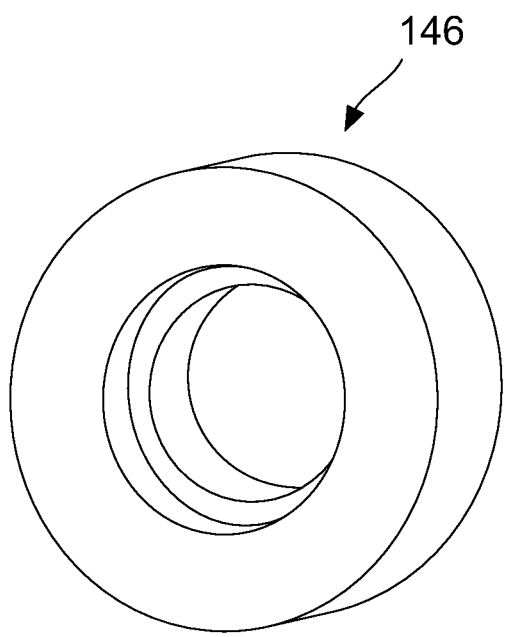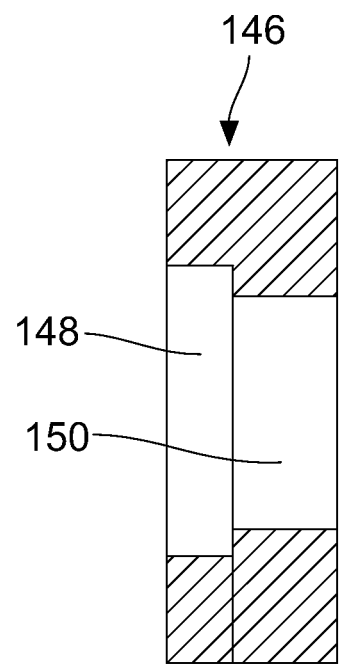
FIG. 13                FIG. 14

METHODS AND DEVICES FOR UTILIZING BONDABLE MATERIALS

CROSS REFERENCE TO RELATED APPLICATIONS

This non-provisional application is a continuation of U.S. patent application Ser. No. 12/711,540 filed Feb. 24, 2010, which is based upon and herein claims priority to U.S. Provisional No. 61/155,133 filed Feb. 24, 2009. This application is related to U.S. patent application Ser. No. 12/202,210 filed Aug. 28, 2008, U.S. patent application Ser. No. 11/689,670 filed Mar. 22, 2007, U.S. patent application Ser. No. 11/671,556 filed Feb. 6, 2007, and U.S. patent application Ser. No. 11/416,618 filed May 3, 2006, the entire contents of each are hereby expressly incorporated by reference into this disclosure as if set forth fully herein.

FIELD OF THE INVENTION

The invention relates to the fastening and stabilizing of tissues, implants, and bondable materials, such as the fastening of a tissue and/or implant to a bondable material, the fastening of an implant to tissue, and/or the fastening of an implant to another implant. This may involve using an energy source to bond and/or mechanically stabilize a tissue, an implant, a bondable material, and/or other biocompatible material. The present invention also relates to the use of an energy source to remove and/or install an implant and/or bondable material or to facilitate solidification and/or polymerization of bondable material.

BACKGROUND OF THE INVENTION

Body tissue often requires repair and stabilization to address weak or fractured bone, torn ligament or tendon, ripped muscle, or separation of soft tissue from bone. There are numerous methods to facilitate this repair and stabilization. For example, weak or fractured bones can be reinforced with bondable material, i.e. bone cement. Over time, these bondable materials may loosen due to tissue deterioration, improper installation of bondable materials, or deterioration of the bondable materials over potentially damaging to the tissue. After the bondable material is sufficiently removed using conventional methods, bondable material is reapplied to the tissue. Therefore, previous stabilization methods provided for the reapplication of bondable materials and did not utilize existing bondable materials. There is a need for an improved method to utilize existing bondable materials to stabilize tissue and implants.

In another example, bondable materials are used for the installation of implants, i.e. example bone cement. However, some implants loose stability over time. Previous stabilization methods require removal of the implant and the remaining bondable material left on the bone. After the bondable materials are removed, new bondable material is applied to the implant and/or bone. Again, this is a time consuming process, potentially damaging the surrounding tissue during the removal of the implant and remaining bondable material.

Bone plates may be positioned internal to the skin, i.e. positioned against the fractured bone, or may be positioned external to the skin with rods connecting the bone and plate. Conventional bone plates are particularly well-suited to promote healing of the fracture by compressing the fracture ends together and drawing the bone into close apposition with other fragments and the bone plate. However, one drawback with plates and screws is that with the dynamic loading placed on the plate, loosening of the screws, and loss of stored compression can result. There is a need for additional fixation devices and methods related to bone plates and other implants providing support to bone.

In addition to internal or external bone plates, surgeons sometimes use intramedullary rods to repair long bone fractures, such as fractures of the femur, radius, ulna, humerus, fibula, and tibia. The rod or nail is inserted into the medullary canal of the bone and affixed therein by screws or bolts. After complete healing of the bone at the fracture site, the rod may be removed through a hole drilled in the end of the bone. One problem associated with the use of today's intramedullary rods is that it is often difficult to treat fractures at the end of the long bone. Fastener members, such as bolts, are positioned through the cortical bone and into threaded openings in the rod. However, the number and positioning of the bolt/screw openings are limited at the tip of the rod because of the decreased surface area of the rod and the reduced strength at the tip of the rod. Fractured bone sections at the distal end of a femur, for example, may not be properly fastened to using conventional intramedullary rod stabilization techniques. Therefore, additional fixation devices and methods are required for use with intramedullary rods.

Other common methods to address weak or fractured bones use a combination of bone screws, bone plates, and intramedullary rods. Conventional methods of using bone screws required a sufficient depth within the bone to stabilize a bone plate. However, weak or fracture bones have limited purchase, as portions of the bone may be unfit for the use of bone screws. Furthermore, if an intramedullary rod has been used to stabilize the bone, the fixation area is further limited as surgeons generally avoid tapping into areas of bone with an underlying intramedullary rod. An improved method of stabilizing existing bone plates and intramedullary rods is needed.

Existing systems and techniques for repairing tissue, like the ones previously described, can be complex, time consuming, lack the characteristic of being employed with precision, be damaging to tissue, and/or fail to provide a robust fastening of tissue. Therefore, there is a need for an apparatus and method for the fastening of tissue that involves a reduction in completion time, greater strength and precision, utilization of previously implanted materials, and preservation of living tissue. There is a need for a system that utilizes of previously installed fixation devices and techniques.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 illustrates an embedding implant and end effector of the invention;

FIG. 3 illustrates an alternative view of FIG. 2;

FIG. 4 illustrates an embedding implant connected to an end effector and embedded in a bondable material;

FIG. 5 illustrates an alternative welding horn or embedding implant of the invention;

FIG. 11 illustrates an alternative configuration of the fastening implant of FIG. 9;

FIG. 12 illustrates a cross section through the center of a long axis of the fastening implant of FIG. 11;

FIG. 13 illustrates a washer for use with implants of the invention;

FIG. 14 illustrates a cross section through the center of a long axis of FIG. 13;

SUMMARY

Figure 1:
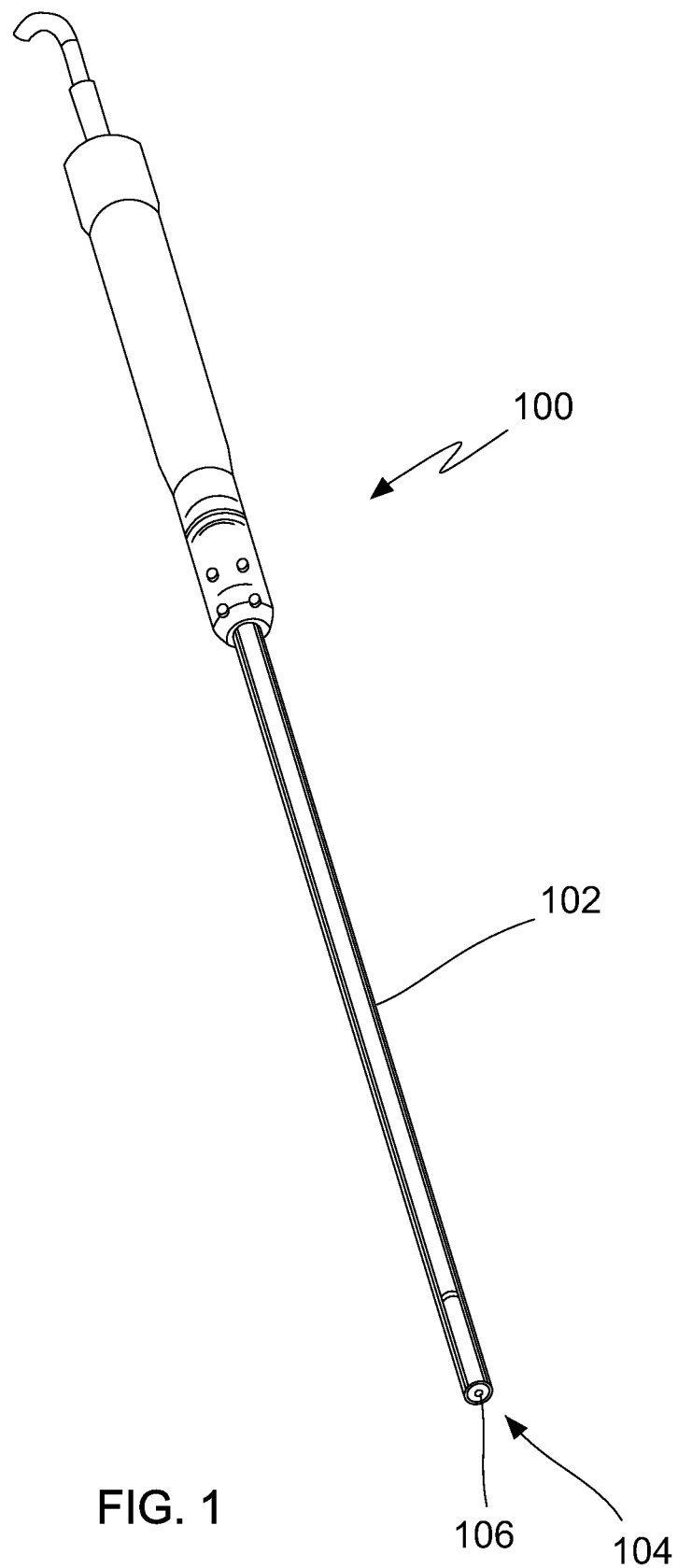
FIG. 1 is a perspective view of an exemplary vibratory energy device.
Figure 6:
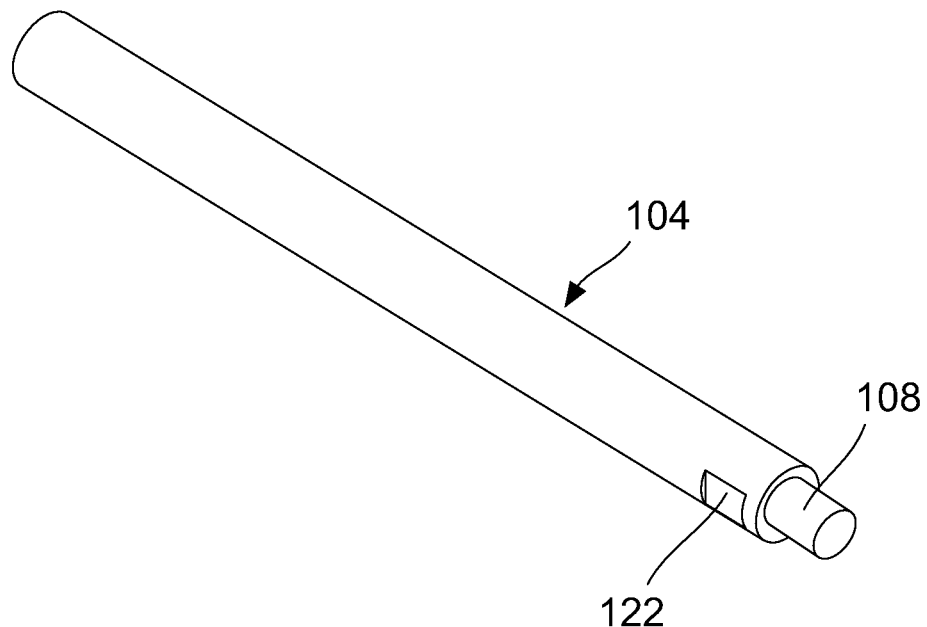
FIG. 6 illustrates an alternative configuration of the end effector of FIG. 3.
Figure 7:
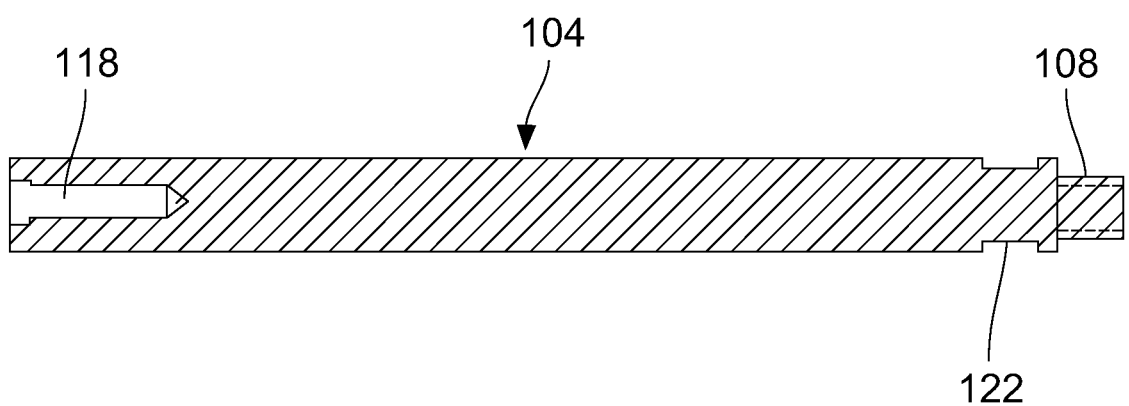
FIG. 7 illustrates a cross section through the center of a long axis of the end effector of FIG. 6.

As is described in further detail below, fasteners may be embedded within solidified bondable material, for example a grouting agent such as bone cement (PMMA) or other acrylic based material. In an embodiment in accordance with the invention, an embedding fastener may be connected to an end effector of a vibratory energy generator. The embedding fastener may be adapted to enter and engage the bondable material that has been locally melted by vibratory energy, and to be securely retained therein once the bondable material has cooled and hardened.

The end effector may be provided in any of a variety of shapes, one example being an elongated rod or shaft, connectable to a hand piece at a proximal end, and operative to transmit vibratory energy at a distal end. The fastener may be adapted to connect to the distal end of the end effector, for example by mechanical interlocking, threading, twist lock configurations, friction fitting, or adhesive attachment. The mechanical connection must be operative, however, to communicate the vibratory energy from the end effector to the fastener.

The fastener is adapted to be securely retained within the bondable material or adhesive, in one embodiment, by being provided with a shaped or contoured surface upon which the adhesive may grip once hardened. A roughened or porous surface may be provided alone or in combination with a shaped surface to increase purchase in bondable material and/or facilitate an interference fit.

The fastener may further be provided with a taper at a leading end which first enters the adhesive. The taper improves performance, at least, by promoting accurate tracking and movement of the fastener into the adhesive, piercing tissue, and facilitating initial melting by concentrating vibratory energy over a smaller surface region.

In a further embodiment of the invention, the embedded bone cement fastener (also referred to as an embedding fastener or embedding implant) described above is provided with one or more radial gaps, chambers, or ports, extending from a central bore. A polymeric fastener is inserted within the central bore, and vibratory energy is applied to the polymeric fastener, whereby polymer at the interface between the embedded fastener and the polymeric fastener melts. When the polymer melts, and particularly as pressure is applied to the polymeric fastener in the direction of insertion, polymer enters the ports, flowing in a direction away from the central bore. When vibratory energy is discontinued, the polymer solidifies, and the polymer fastener is thereafter secured within the embedding fastener.

The embodiments of the present invention may be utilized with limitless fixation techniques and in conjunction with other fasteners and implants. Furthermore, the embodiments herein may assist in the installation and removal of tissue and implants. Moreover, the embodiments of the present invention may assist in the delivery of therapeutic agents and employ methods that facilitate tissue growth and repair. In addition, the embodiments herein may be used to apply vibratory energy to remove and/or install an implant in bondable material or to facilitate solidification and/or polymerization of the bondable material.

DETAILED DESCRIPTION

The invention relates to the devices and methods for the utilization of bondable materials and bondable materials, fixation and fastening of tissue to tissue, an implant to tissue, and an implant to an implant both inside and outside the body. The invention additionally relates to removing and anchoring implants to bondable materials and/or other biocompatible materials, anchoring implants using previously implanted and hardened bondable materials, and fixation using vibratory energy, mixing, solidifying, bonding, and/or mechanical interlocking of materials. The present invention also relates to the use of an energy source to install and/or remove an implant or bondable material or to facilitate the solidification and/or polymerization of a bondable material The methods and devices disclosed herein may be used in conjunction with any medical procedure on the body. The stabilization, fastening, and/or repair of tissue or an implant may be performed in connection with any medical procedure related to a joint, bone, muscle, ligament, tendon, cartilage, capsule, organ, skin, nerve, vessel, or other body parts. For example, tissue may be stabilized during intervertebral disc surgery, kyphoplasty, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

Also, an implant may be inserted within the body and fastened to tissue with the present invention. Such implant insertion procedures include, but are not limited to, partial or total knee replacement surgery, hip replacement surgery, shoulder replacement surgery, bone fastening surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal (porous or nonporous), polymer, composite, or ceramic. Collagen may provide the benefit of bolstering tissue growth. Additionally, a desiccated collagen may be used to absorb surrounding fluid, which may provide the additional benefit of applying pressure on the tissue being repaired. Other implants include breast implants, biodegradable plates, porcine or bovine patches, metallic fasteners, compliant bearing for medial compartment of the knee, nucleus pulposus prosthetic, stent, suture, suture anchor, tissue graft, tissue scaffold, biodegradable collagen scaffold, and polymeric or other biocompatible scaffold. The scaffold may include fetal cells, stem cells, embryonic cells, enzymes, and proteins.

In this application, the term "bondable" or "bondable material" is used to refer to the materials discussed herein, as well as any material, suitable for in vivo applications, which can be softened and made flowable by the application of heat (such as heat produced with vibratory energy such as ultrasonic energy), and which, when softened, may become tacky and will bond to other materials and will flow to fill available space. Thus, the material may be thermoplastic, but it may also exhibit tackiness or bonding ability when in its plastic form. Many materials suitable for in vivo applications are made of or incorporate such bondable materials. Generally speaking, the amount of heat needed to soften and make flowable should be within a temperature range that does not produce substantial thermal tissue necrosis. Alternatively stated, the amount of heat required to soften the bondable material during vibratory bonding is substantially confinable, due to the thermal properties of the bondable material, to an area of contact between the objects which are being bonded, thereby protecting living body tissue near the contact between the two objects from substantial thermal tissue necrosis. Any embodiment herein may be used with any of the materials and/or applications disclosed herein or known in the art.

The fixation and fastening system and other embodiments of the present invention contemplates the use any materials that may include or be used in conjunction with bondable materials for bonding and/or staking within the human body. Implants that may be used as fasteners may also be referred to as fastening implants. Bondable material used may include, but are not limited to, biocompatible, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, bondable material, and combinations thereof. Bondable material may also include polymethyl methacrylate (known as "PMMA" or "bone cement"), glue, adhesive, and/or other grouting agents or acrylic materials used for fixation.

In this application, "bond", "bonded", and "bonding" includes, but is not limited to, attaching, engaging, connecting, binding, adhering, and/or fastening one or more materials through resistive heating, mechanical interlocking, application of force, application of grouting agents (i.e. bone cement), adhesives and/or solvents, spraying, radiofrequency, vibratory energy (i.e. ultrasound), microwave, laser, electromagnetic, electro shockwave therapy, plasma energy (hot or cold), and other suitable method described herein or known in the art.

Preferably, materials of the present invention can melt with the application of energy, becoming gel-like, tacky, and/or soft. The energy source and the technique used to bond and/or stake the material within the body can be selected to minimize or avoid damage to surrounding body tissue. Exemplary materials that may be used may include polymers, ceramics, composites, and metals, although other materials may also be suitable for use with the invention. While the present invention contemplates the use of any of these materials in any of the following embodiments, polymeric material is used in the following examples and description simply to illustrate how the invention may be used.

There are a limitless number of materials may be used for the present invention. Examples of amorphous polymers are polycarbonate (LEXAN), polystyrene, polysulfone (ULDALL), and acrylics polycarbonate (ABS and styrenes). Examples of semi-crystalline polymers include acetyl (DELRIN), nylon, polyester, polyethylene, polyether ether ketone, polypropylene, polyvinylchloride (PVC), and Caprolactam. Biodegradable semi-crystalline polymers may include polylactic acid and polyglycolic acid. Copolymers of PGA and PLA may also be used. Poly-1-lactide (PLLA) or other forms of PLA may also be used. Other polymers which may be used with the present invention, either as a thermoplastic or non-thermoplastic, are polyethylene glycol (PEG)-copolymers and D,L-lactide-co-glycolide polyesters. Some semi-crystalline materials are particularly suitable for surgical bonding and/or staking, especially vibratory bonding and staking. Examples of such materials include PAEK (polyaryletherketone), including PEEK (polyetheretherketone) and PEKK (polyetherketoneketone).

In addition to PEEK and the other polymers described herein, the implants, devices, and methods of the present invention may use keratin, a naturally occurring polymer. Keratin may be vibratory bonded or staked to itself, to other implants, or within tissue. This may be performed in the operating room or intracorporeally. Keratin may be bonded to collagen or to other known polymers. In an exemplary application, keratin may be used to fasten tissue to bone since keratin has BMP and tissue scaffold properties. It is contemplated that any of devices and methods disclosed herein may utilize keratin alone or in combination with PEEK, polylactic acid, or other polymer. Keratin may be used to make fasteners, disc replacements, joint replacement components, stents, cell scaffolds, drug reservoirs, etc. Also, joint bearing surfaces may include keratin with or without collagen or chondrocytes. The bearing surfaces may be fastened to a joint component using PEEK or PLA fasteners.

Another polymer that can be used with the present invention is a class of natural materials, called polyhydroxyalkanoates, or PHA polymers. These polymers are synthesized in nature by numerous microorganisms, and they have been recently recognized as the fifth class of naturally occurring biopolymers (along with the polyamino acids, polynucleic acids, polysaccharides, and polyisoprenoids). Unlike the other naturally occurring biological polymers, however, the PHA polymers are thermoplastic, i.e. they may be repeatedly softened with heat and hardened with cooling. As such, these polymers can be processed much like other plastics. A specific example of a PHA polymer that could be used is poly-4-hydroxybutyrate material. Such PHA polymers are available from Tepha Inc of Lexington, Mass.

Fasteners of the invention may utilize or be coated with polymethylmethacrylate (PMMA), in order to promote bonding with PMMA used in the body, or PMMA could be incorporated into polymer of the fastener, or deposited within cavities or shapes formed in the fastener surface, including threaded, roughened, porous, or nano textures. A fastener may be thus coated with PMMA, or formed entirely of PMMA, and may be heat bonded, advantageously using ultrasound, to another PMMA surface or other adhesive surface, otherwise as described herein with respect to bone cement. Although PMMA, known generally as bone cement, and other polymers may function more as a grouting agent than a cement or adhesive. The term "bondable material" is used throughout the specification for simplicity.

In accordance with the invention, metals are advantageously connected with fasteners incorporating polymeric materials. Any of a variety of metals may be used, either smooth or formed with at least portions formed of metal, or a roughened or porous surface, or formed with cavities or other shapes upon which polymeric material may mold, enter, adhere, or otherwise affix. The polymer is softened in accordance with the invention through the application of heat, including heat created using vibratory energy, to become tacky, or sufficiently softened in order to bond on a microscopic level, or a macroscopic level through adaptation to the surface structure of the metal. For use in vivo, biocompatible metals are used, including stainless steel, nitinol or other SMA (shape metal alloy), tantalum, porous tantalum, titanium, cobalt-chrome alloys, and other metals such as are known to those skilled in the art. Additional related information, including bonding polymers and metals, and polymer to polymer bonding of implant materials, may be found in U.S. Pat. No. 5,163,960 entitled "Surgical devices assembled using bondable materials", and U.S. Pat. No. 7,104,996 entitled "Method of performing surgery", the contents of each of which being incorporated herein by reference.

The fastening device of the present invention may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable polymer layer or layers.

The therapeutic agents may also be placed within one or more cavities disposed in a fastening device of the present invention. Different agents may be disposed in different cavities of the device to specifically tailor the implant for a particular patient. Dosages of the therapeutic agent may be the same or different within each of cavities as well. The cavities may include a cover which may release the agent in a controlled or timed manner. The cover may be biodegradable or bioerodible to allow the agent to release to surrounding tissue. Examples of suitable therapeutic agents include bone growth inducing material, bone morphogenic proteins, osteoinductive materials, apatite compositions with collagen, demineralized bone powder, or any agent previously listed. U.S. patent application Ser. No. 11/549,994 entitled "Drug Eluting Implant" discloses means for delivering therapeutic agents. The above-mentioned patent application is incorporated by reference herein in its entirety.

The fastening devices of this and other embodiments of the invention may be used in combination with fasteners in the prior art. Examples of fasteners, implants, and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 12/202,210; 10/102,413; 10/228,855; 10/779,978; 10/780,444; and 10/797,685. The above cited patents and patent applications are hereby incorporated by reference in their entirety.

With reference to FIG. 1, any known energy emitting instrument may be used with the surgical system of the present invention. Instrument 100 may produce energy such as resistive heating, radiofrequency, ultrasound (vibratory), microwave, laser, electromagnetic, electro shockwave therapy, plasma energy (hot or cold), and other suitable energy disclosed herein or known in the art. FIG. 1 illustrates an exemplary handpiece or instrument 100 that may be used with the present invention. The instrument 100 may be a vibratory energy generator with a sheath 102 to cover and protect the end effector 104 and engage a fastener/implant near engagement feature 106. As will be discussed below, the instrument may be used to bond and/or mechanically interlock fasteners and other embodiments the present invention. Additional embodiments of instrument 100 are disclosed in U.S. patent application Ser. No. 12/202,210 entitled "Methods and Devices for Utilizing Thermal Energy to Bond, Stake and/or Remove Implants", which is incorporated by reference herein.

With reference to FIGS. 2-7, end effector 104 may be utilized with anchor or embedding fastener 110. Embedding fastener 110 may also be referred to as an embedding implant. FIG. 2 illustrates end effector 104 that connects to embedding fastener 110 with distal end 108. The connection between distal end 108 and embedding fastener 110 may utilize threads, magnetism, friction, taper, ball and socket, linkage, adhesive, interlocking shapes, and other connections known in the art. Additionally, distal end 108 and embedding fastener 110 may be permanently or detachably connected.

As shown in FIG. 2, embedding fastener 110 may further be provided with a taper 114, which first enters bondable material 120 in FIG. 4. Taper 114 may improve performance, for example, by promoting accurate tracking and movement of embedding fastener 110 into bondable material 120, piercing body tissue, and facilitating initial melting by concentrating vibratory energy over a smaller surface region. Although embedding fastener 110 may be made of any material described herein or known in the art, it may be preferable to use titanium.

As discussed in further detail below, embedding fastener 110 may also have feature 112 and/or feature 116, either or both may be a surface feature, recess, or pass through a portion or the entirety of embedding fastener 110.

Referring to FIG. 3, an embodiment of end effector 104 may have proximal end 118 to the other components of instrument 100. The connection between instrument 100 and proximal end 118 may be threaded, magnetic, friction, hex, ball and socket, linkage, adhesive, and other methods disclosed herein or known in the art.

As shown in FIGS. 3-7, end effector 104 may be provided in any of a variety of shapes, one example being an elongated rod or shaft, connectable to a hand piece at a proximal end 118, and operative to transmit vibratory energy at a distal end 108. While a rod shape is shown and selected for reduced manufacturing cost, end effector 104 may have the form of box or hex channel, oval or other shape, provided it communicates vibratory energy to a distal end 108, an attached fastener, or embedding fastener 110. Additionally, feature 111 of FIG. 5 may be used on embedding fastener 110 or integrated into end effector 104 (not shown).

In an additional embodiment, embedding fastener 110 is adapted to connect to distal end 108 of end effector 104 by mechanical interlocking, as by a bore in embedding fastener 110, sized to receive distal end 108 of end effector 104, optionally provided with internal or external threading (not shown), wherein post 108 has mating threads. Additionally, the connection may be threaded, magnetic, friction, hex, ball and socket, linkage, adhesive, and other methods disclosed herein or known in the art. Similarly, a bore or aperture may be provided in end effector 104, mateable with a post or projection on embedding fastener 110. Other mechanical connections are contemplated, including twist lock configurations, friction fitting, or adhesive attachment. The mechanical connection should preferably be operative to communicate vibratory energy from end effector 104 to embedding fastener 110, as by a firm mechanical connection.

As shown in an embodiment of FIG. 4, embedding fastener 110 may be adapted to be securely retained within bondable material 120 by being provided with a shaped or contoured surface upon which the softened bondable may adhere. A roughened or porous surface may be provided alone or in combination with shaped surface thereby providing for increased purchase in bondable material 120.

With reference to FIG. 4, embedding fastener 110 may be embedded within solidified bone bondable material 120, for example PMMA, acrylic based adhesive, or other bondable materials. In the present invention, embedding fastener 110 is connected to end effector 104 of an embodiment of instrument 100, such as a vibratory energy generator as shown in FIG. 1. Embedding fastener 110 is adapted to enter and engage bondable material 120 or bondable material 120 that has been locally melted by vibratory energy (as shown in FIG. 4), through contact between embedding fastener 110 and bondable material 120 during operation of instrument 100. Embedding fastener 110 is securely retained by bondable material 120 once the latter has hardened. Although the embodiment in FIG. 4 may be used under a limitless number of configurations and settings, Table 1 is being set forth with operative examples:

TABLE 1

Figure 20:
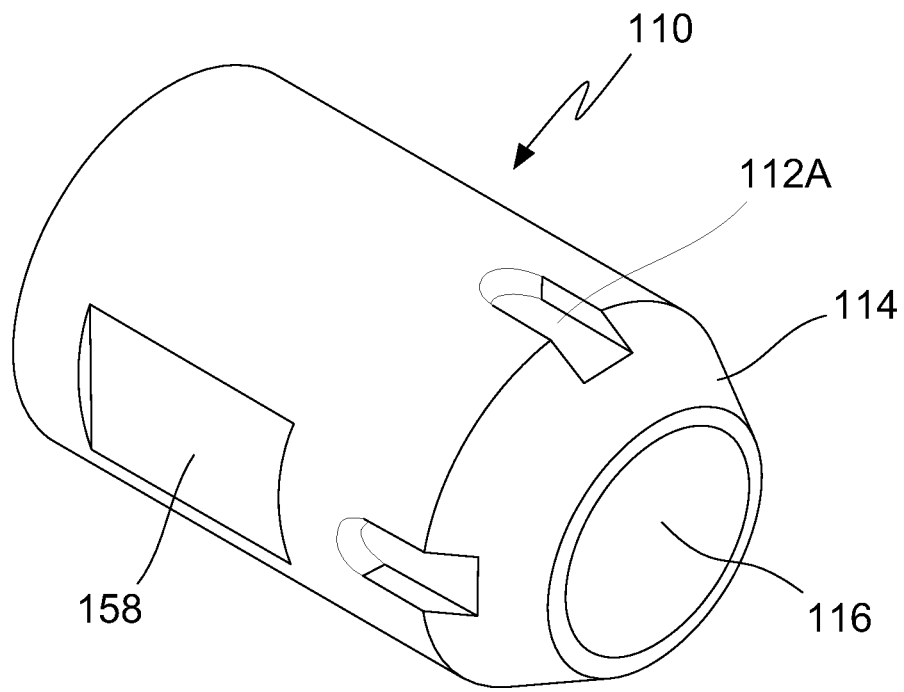
FIG. 20 illustrates an alternative configuration of an embedding implant.
Figure 21:
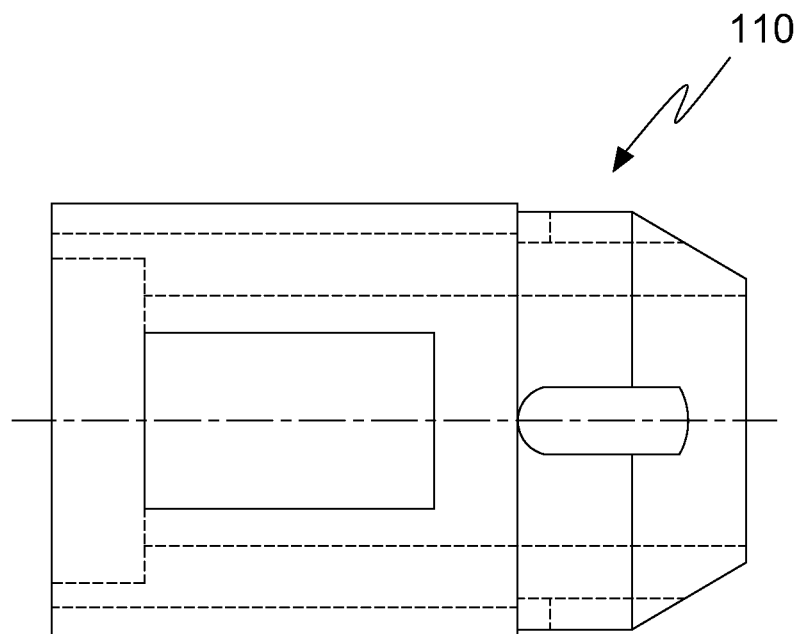
FIG. 21 illustrates a cross section through the center of a long axis of FIG. 20.
Figure 22:
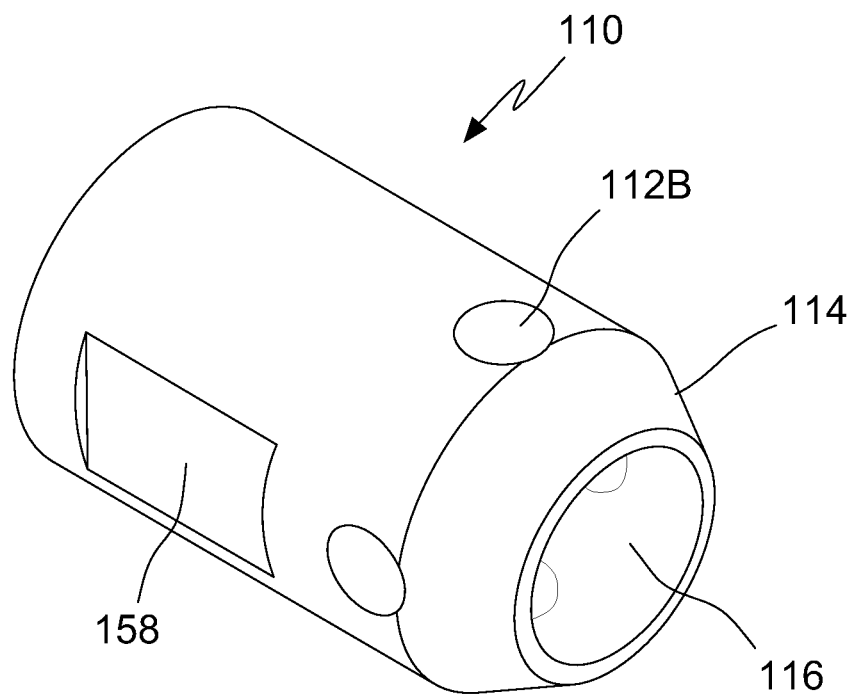
FIG. 22 illustrates an alternative configuration of the embedding implant of FIG. 2.
Figure 23:
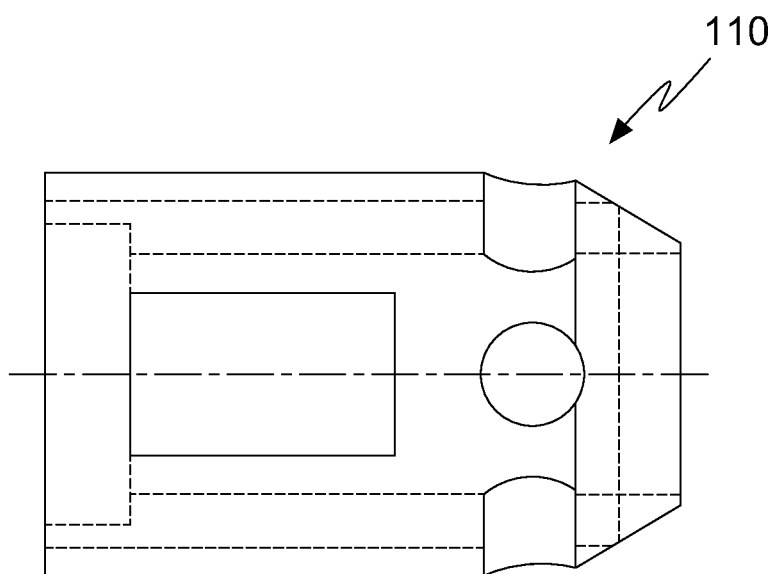
FIG. 23 illustrates a cross section through the center of a long axis of FIG. 22.
Figure 24:
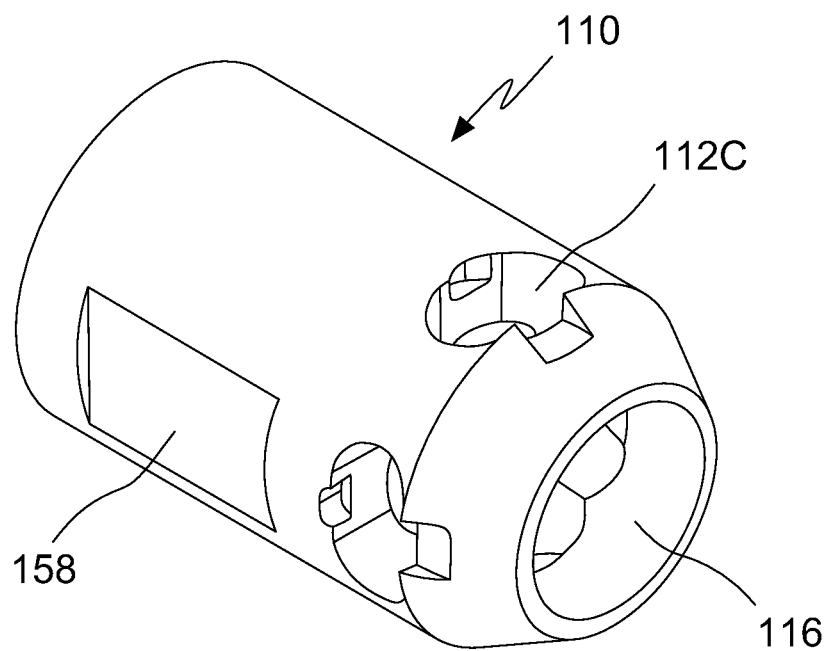
FIG. 24 illustrates an alternative configuration of the embedding implant of FIG. 2.
Figure 25:
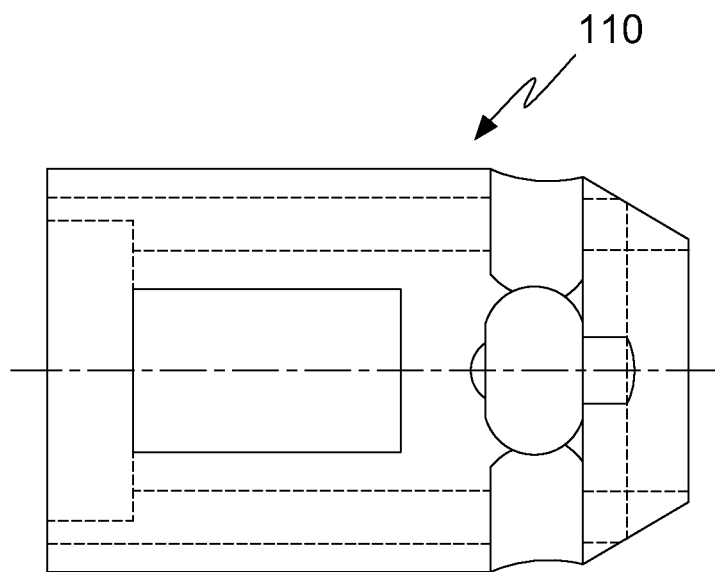
FIG. 25 illustrates a cross section through the center of a long axis of FIG. 24.

Titanium Embedding Fastener Bonded into PMMA
Embedding Fastener Type: Shown in FIG. 20
Instrument: Handpiece SN0105 with tuning of 39,000-45,000 Hz
System Settings:
Sample 1: 40,850 Hz, 100W, 2.0 sec weld time
Sample 2: 40,750 Hz, 75 W, 1.5 sec weld time
Sample 3: 40,800 Hz, 75 W, 1.0 sec weld time
Sample 4: 40,750 Hz, 75 W, 1.0 sec weld time

| Test Sample Number | Power (watts) | Time (sec) | Force Applied to Break (lbs.) | Deformation Depth (inches) |
|---|---|---|---|---|
| 1 | 63 | 2.56 | 46.7 | 0.116 |
| 2 | 48 | 2.01 | 61.9 | 0.119 |
| 3 | 48 | 1.58 | 32.5 | 0.109 |
| 4 | 48 | 1.47 | 31.5 | 0.098 |

Figure 9:
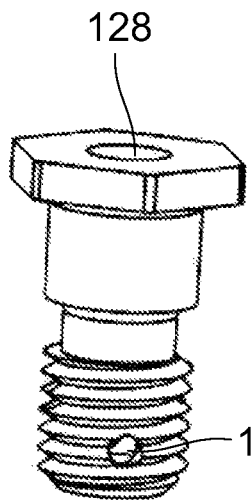
FIG. 9 illustrates an alternative view of FIG. 8.
Figure 8:
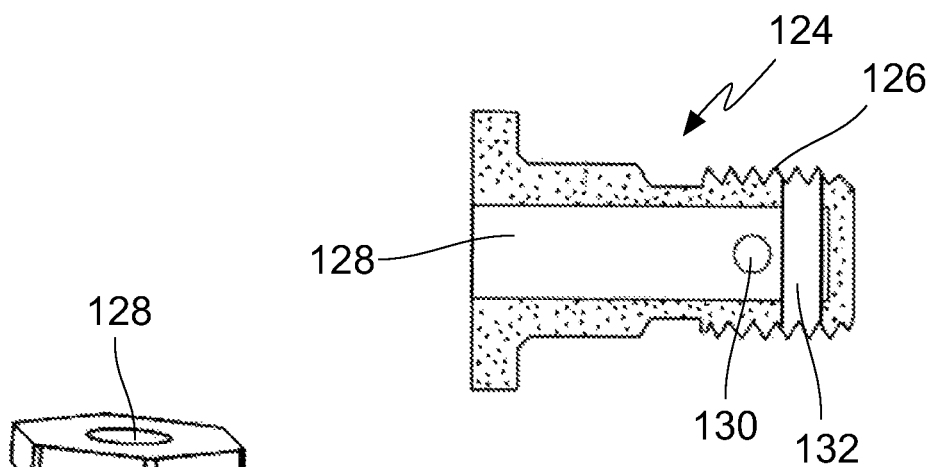
FIG. 8 illustrates a cross section through the center of a long axis of a fastening implant.
Figure 10:
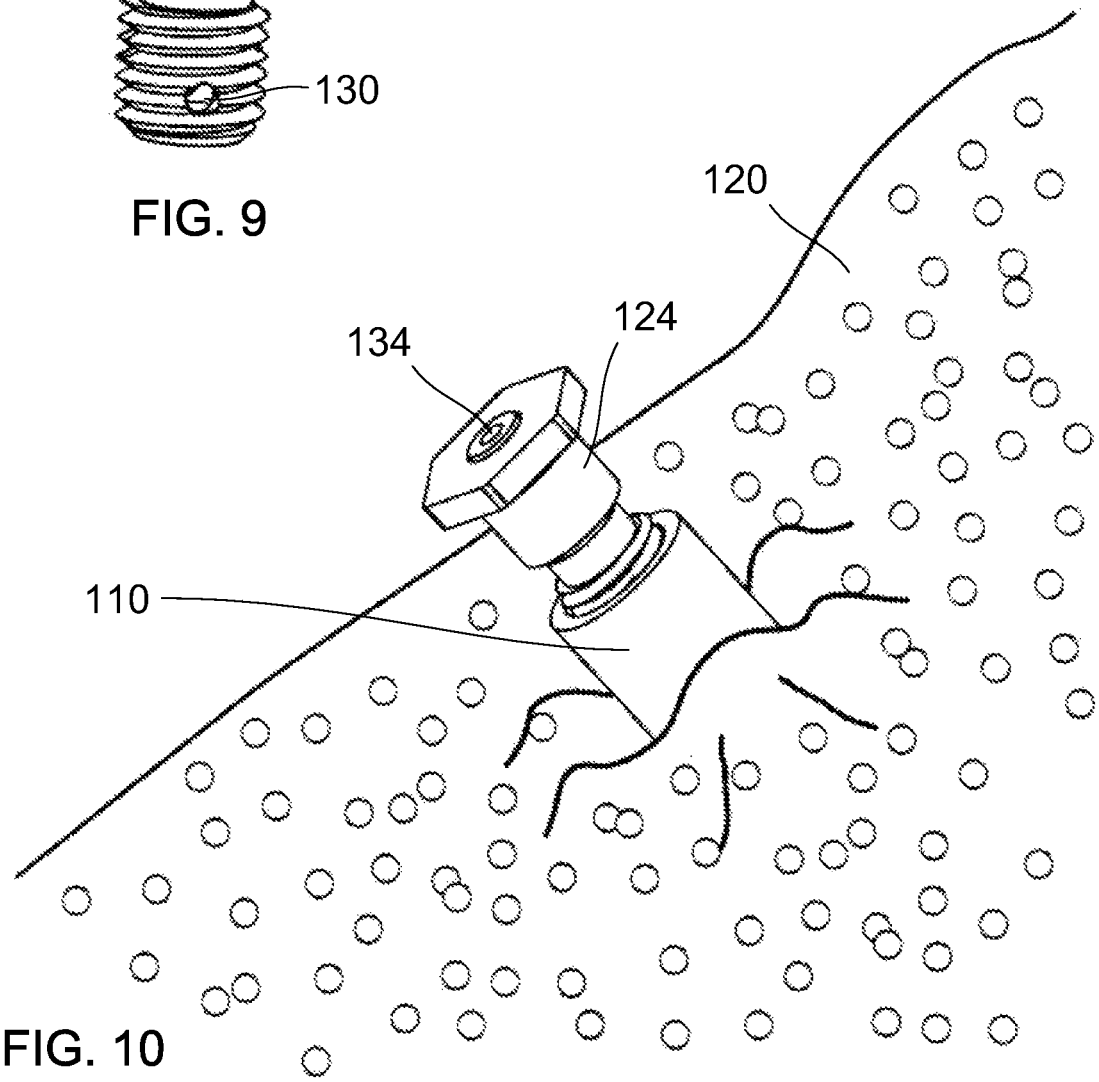
FIG. 10 illustrates the embedding implant embedded in bondable material and engaged with a fastening implant.

Once anchored, end effector 104 and embedding fastener 110, embedded in bondable material 120, may remain connected. Alternatively, end effector 104 may be removed and another fastener of a similar or different design may be connected to an implanted embedding fastener 110 as shown in FIGS. 8-10. In a further embodiment, fastener 124 such as described in the incorporated patents and applications may be fastened to an implanted or installed embedding fastener 110. Fastener 124 may have fastener bore 128 as shown in FIGS. 8-9. Referring to FIG. 10, a bondable insert 134 may be secured into fastener bore 128. Bondable insert 134 may be secured by press fitting, threading, or bonding to fastener bore 128 and/or embedding fastener 110. The fastener 124 may be utilized as detailed in U.S. patent application Ser. No. 12/202,210, which has been incorporated by reference herein. In further embodiments, any fastener described in the related references cited in paragraph [0001] or discussed herein may be fastened to the embedding fastener 110, then secured in its respective manner.

In an additional embodiment, embedding fastener 110 may be used to remove an implant and/or bondable material 120. For example, the ability of conventional medical tools to remove a previously installed implant or bone cement may be limited. Embedding fastener 110 may be used to obtain additional fixation. Once embedding fastener 100 is secured to the implant and/or bondable material 120, force and/or vibratory energy may be used to remove the implant and/or bondable material 120.

Figure 15:
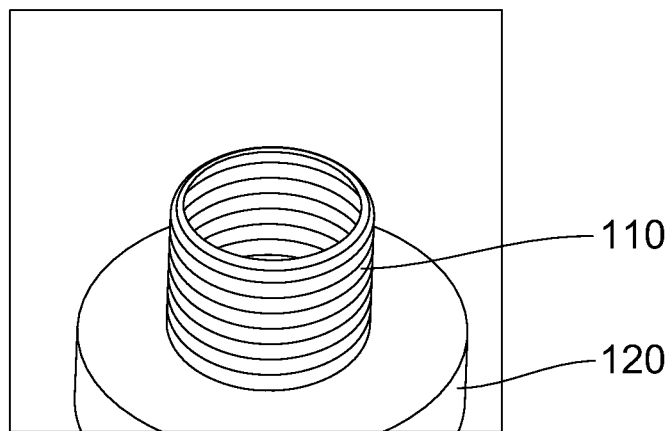
FIG. 15 illustrates embedding implant embedded in bondable material.
Figure 16:
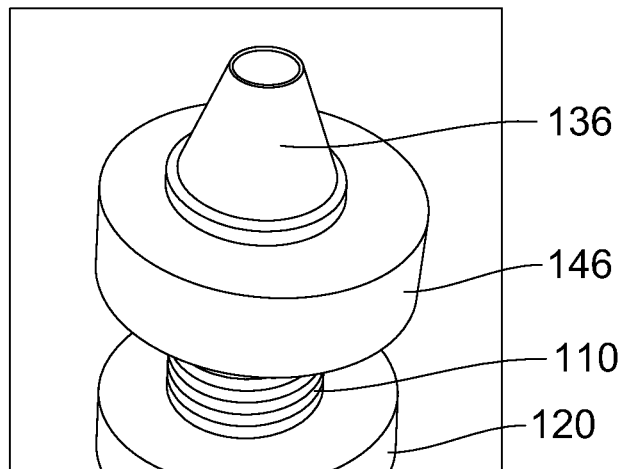
FIG. 16 illustrates the fastening implant of FIG. 11 disposed in the washer of FIG. 13 and engaged with the embedding implant of FIG. 15.
Figure 17:
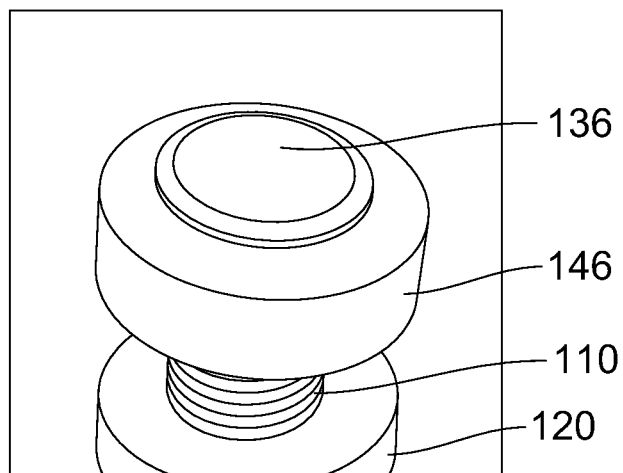
FIG. 17 illustrates the fastener of FIG. 11 bonded and/or staked to the washer of FIG. 13.

FIGS. 11-17 show an additional embodiment for use with an implanted embedding fastener 110. Fastener 136 is show in FIGS. 11-12 and washer 146 is shown in FIGS. 13-14. Although fastener 136 and washer 146 may be made of any material disclosed herein or known in the art, it may be preferable to use PEEK. After embedding fastener 110 has been secured with respect to bondable material 120, fastener 136 may be engaged into embedding fastener 110. In another embodiment, washer 146 may be used in conjunction with fastener 136 as shown in FIGS. 15-17. Additionally, fastener 136 may be bonded to embedding fastener 110 and/or washer 146.

Figure 18:
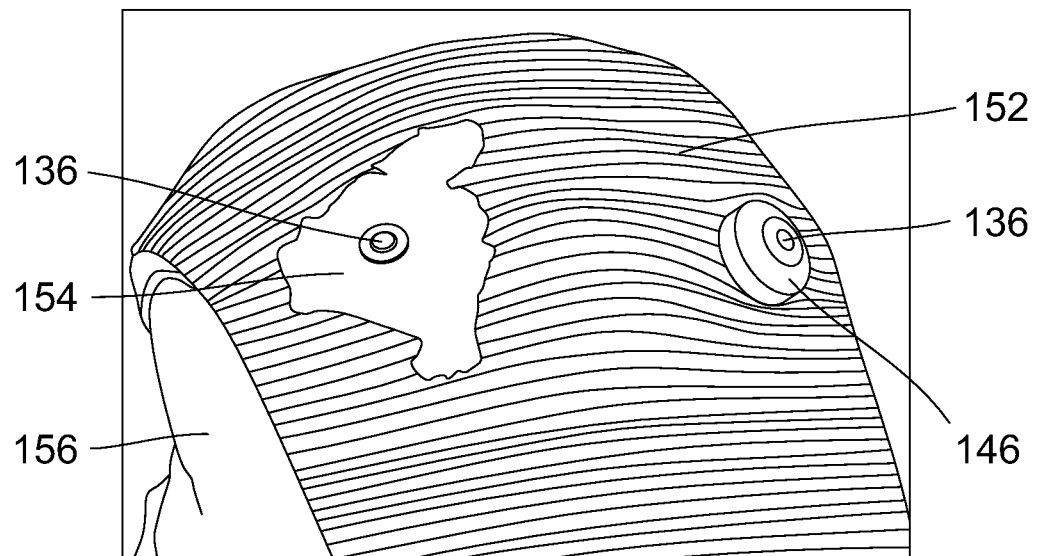
FIG. 18 illustrates alternative configurations of implant of the invention.
Figure 19:
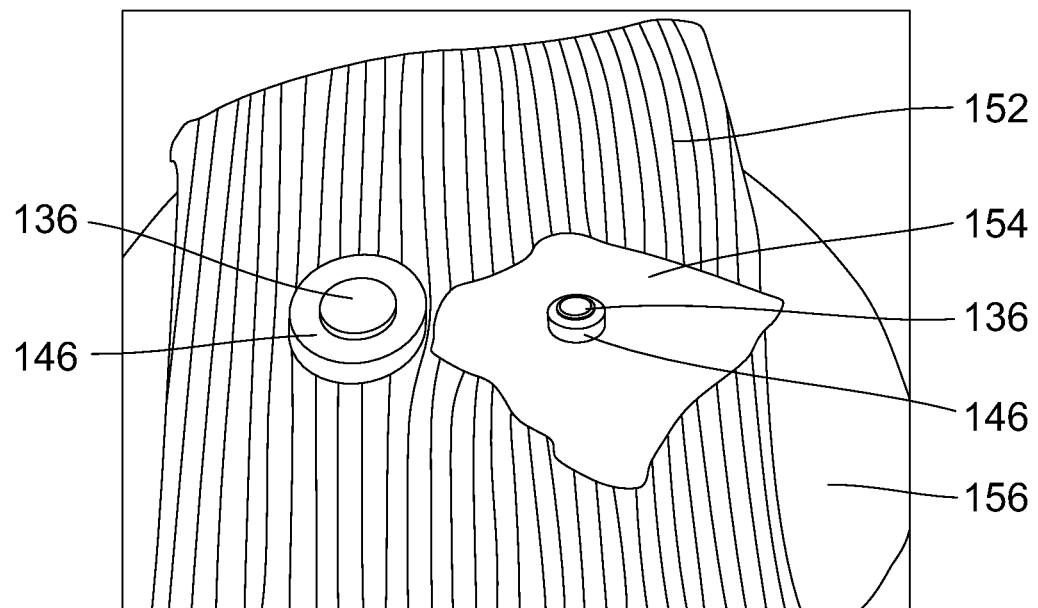
FIG. 19 illustrates alternative configurations of FIG. 18.

Referring to FIGS. 18-19, fastener 136, washer 146, and/or tissue implant 154 may be used to secure soft tissue 152 to hard tissue 156, for example to secure the rotator cuff tissue to the proximal humerus or for any other procedure disclosed herein. Additionally, washer 146 and/or tissue implant 154 could be made of collagen or other materials that promote tissue growth.

With reference to FIGS. 20-25, embedding fastener 110 may be provided with channel 112. For example, channel 112A, 112B, 112C, and/or 116 may be used. Channel 112 may extend through the surface of embedding fastener 110 to facilitate the bonding of embedding fastener 110 to bondable material 120, fastener 136, and/or any fastener disclosed herein. Channel 112 may provide a path for softened and/or molten bondable material to be displaced, providing room for entry of embedding fastener 110. Channel 116 may also include radial gaps, chambers, or ports. To accommodate for embedding fastener 110 displacing a substantial amount of material, channels may be extended along the entire length of embedding fastener 110, and may further extend along end effector 104. Channel 116 may be further operative to reduce the possibility of rotation of fastener 110 within bondable material 120. Channel 116 is thus disposed to extend into bondable material 120 after insertion, and may extend to the face of embedding fastener 110. Additionally, embedding fastener 110 may have feature 158 to help attach and remove it from end effector 104.

Figure 26:
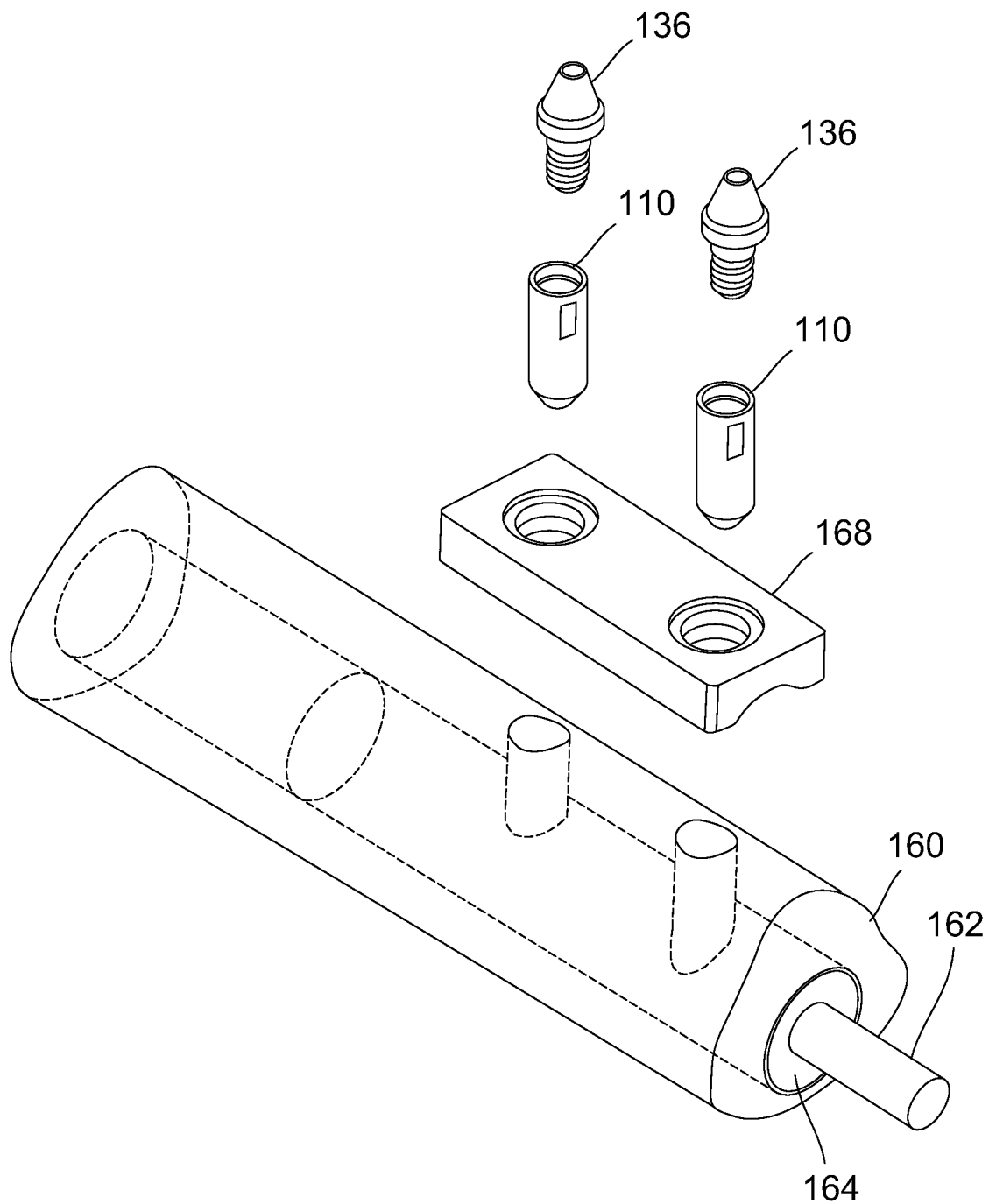
FIG. 26 illustrates the use of a fastening implant and an embedding implant to secure a supporting implant.
Figure 27:
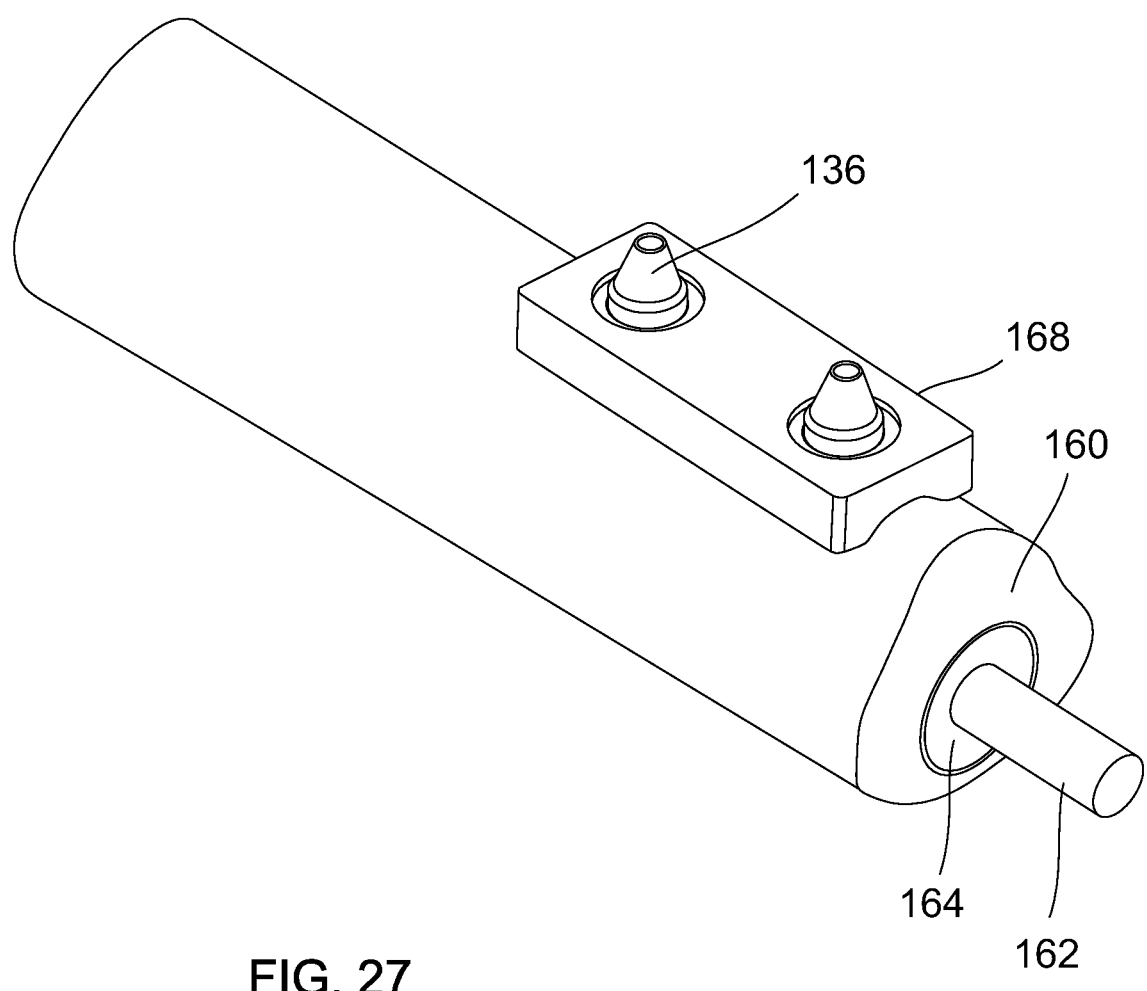
FIG. 27 illustrates the assembled configuration of FIG. 26.

In an embodiment shown in FIGS. 26-27, implant 162 may be coated in bondable material 164 and implanted in body tissue 160. For example, a metal rod coated with bone cement may be placed in the intramedullary canal of a bone. In an embodiment, support 168 may be placed in a location to facilitate stabilization. Support 168 and/or washer 146 may be referred to as a supporting implant. One or more holes may be formed in body tissue 160 and up to or into bondable material 164 to coincide with the holes in support 168. Embedding fastener 110 may be placed through the holes in body tissue 160 and secured to and/or bonded to bondable material 164 as discussed herein. Then, one or more of fastener 136 are secured to and/or bonded to the one or more embedding fastener 110, thereby securing support 168 relative to body tissue 160.

Figure 28:
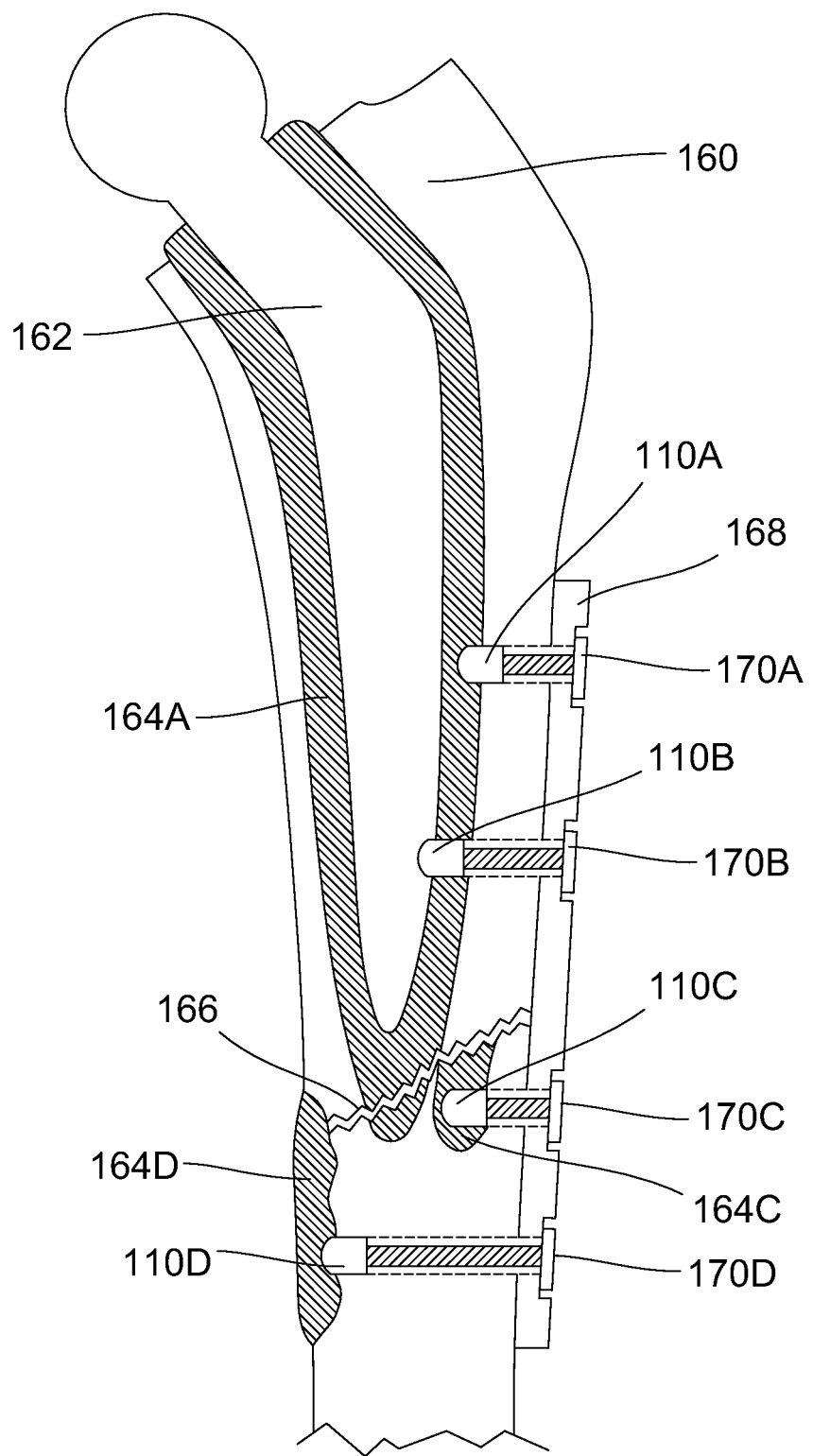
FIG. 28 illustrates devices and methods related to utilization of implants and bondable materials.

Referring to FIG. 28, implant 162 may be installed in a body tissue 160 with bondable material 164, for example bone cement. Bondable material 164 may be any material described herein or known in the art. Implant 162 may require stabilization because implant 162 has become loose and/or requires stabilization due to tissue defect 166, for example a periprosthetic fracture. Tissue defect 166 may include, but is not limited to, damaged, deformed, and/or diseased bone, muscle, ligament, tendon, cartilage, capsule, organ, skin, nerve, vessel, or other body part. For example, a femur may be fractured or contain osteoporosis. Support 168 is fixed to body tissue 160 with fastener 170 to provide stabilization. Support 168 may be an internal bone plate, an external bone plate, a spinal plate, a wedge, a cushion, a pad, or other biocompatible support used for stabilization of tissue and/or implants. Fastener 170 may be any fastener described herein or any other biocompatible fastener known in the art.

In an embodiment, implant 162 has been previously installed and requires stabilization. One or more holes are formed through body tissue 160 and up to or into bondable material 164. Embedding fastener 110 is inserted through a hole and bonded to bondable material 164 by utilizing instrument 100 described above. Fastener 170 engages embedding fastener 110 to secure support 168 to body tissue 160. The head of fastener 170 may be deformed and/or bonded to support 168 to reduce loosening of fastener 170.

Embedding fastener 110 can also be bonded to bondable material 164C/D that is within or on the surface of body tissue 160. For example, bondable material may have been used to repair tissue defect 166. Bondable material 164 may be within or on the surface of body tissue 160. A hole is formed up to or into the bondable material 164. Embedding fastener 110 is bonded into bondable material 164. Fastener 170 passes through support 168 and into engagement with embedding fastener 110 to secure support 168 relative to body tissue 160.

In another embodiment, embedding fastener 110A/B can be bonded to and/or into implant 162. The procedure is performed as described above, except the embedding fastener 110 may be bonded directly to implant 162.

In another embodiment, bondable material 164 may asymmetrically cover all or a portion of implant 162. The thickness of bondable material 164 could vary in the radial direction or along the length of implant 162. An asymmetrically coated implant 162 may provide additional purchase for fastener 136 or indication of orientation or position of implant 162.

In an additional embodiment, indirect visualization may be used to identify and/or change the orientation or position of implant 162 or fastener 136. Examples of indirect visualization may include endoscopic guidance, computer assisted navigation, magnetic resonance imaging (MM), CT scan, ultrasound, fluoroscopy, X-ray, or other visualization technique disclosed in any of the references incorporated herein. Asymmetric coating, radiopaque markers, or other features identifiable with indirect visualization may be used to identify and/or adjust orientation or position. Indirect visualization may also be used to align fastener 136 with holes in implant 162 or bondable material 164. The holes may be predrilled in implant 162 or bondable material 164 or may be drilled after installation of 162. Indirect visualization may be used to create a hole or holes in tissue to align with holes in implant 162 or bondable material 164.

For example, an intramedullary rod could be asymmetrically coated with PEEK. The intramedullary rod could have predrilled holes in the PEEK coating. After the rod is installed in the intramedullary canal of the tibia, the orientation of the rod may be determined using indirect visualization to locate the area with a thicker coating. The orientation of the rod may be adjusted to the appropriate location for holes to be made through the tissue.

Figure 29:
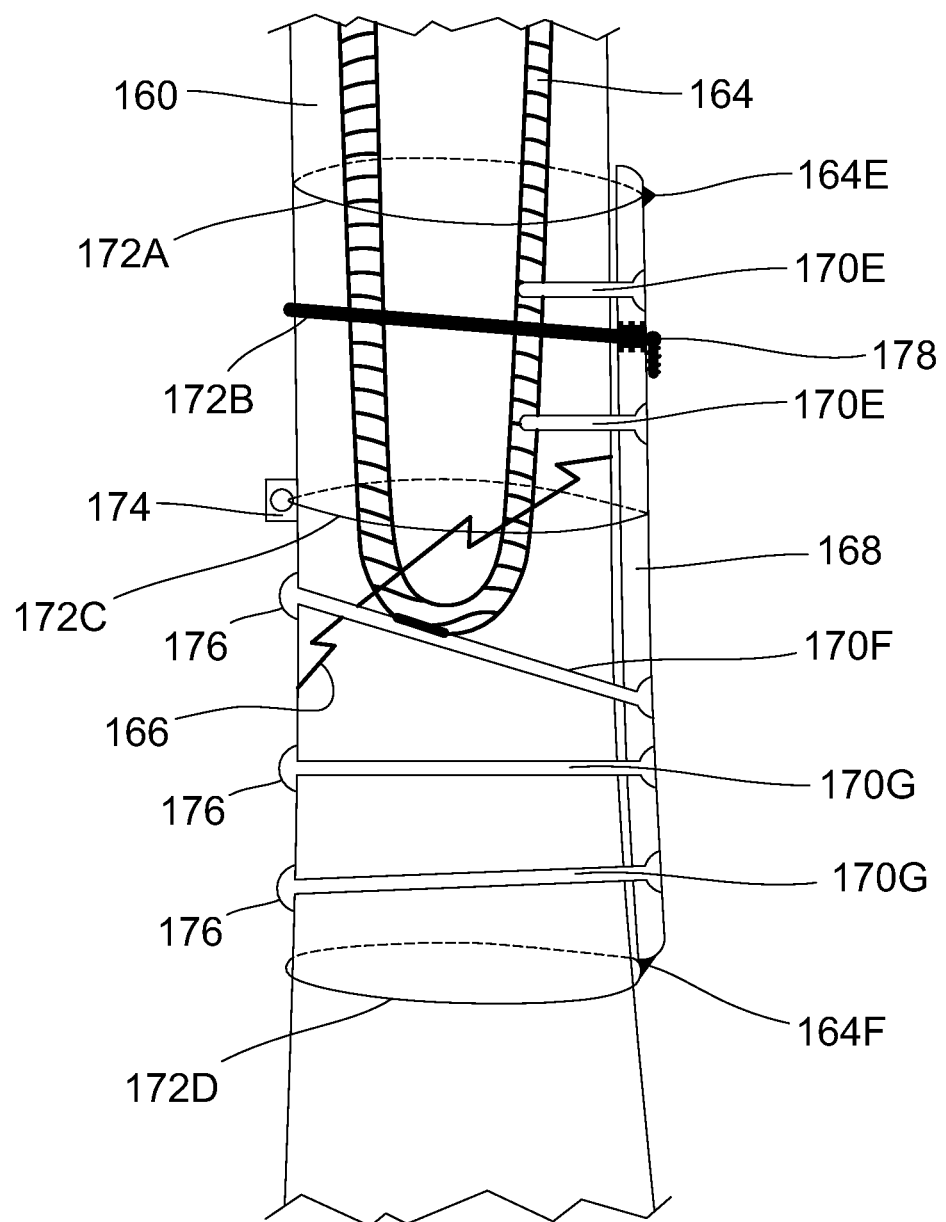
FIG. 29 illustrates alternatives for the devices and methods of FIG. 28.

With further reference to FIG. 28-29, various types of fastening devices are used to position support 168 along body tissue 160. Alternatively, support 168 may be positioned upon the surface of the skin, or at any point between the tissue surface and the skin, according to the requirements of the surgical procedure. Further, support 168 may be placed within the bone, for example in an intramedullary canal.

Referring to FIG. 29, fastener 170 may be used in intramedullary, percutaneous, and/or retrograde approaches. Fastener 170 may be bonded to bondable material 164, or a surface of implant 162. The head of fastener 170 may be provided, or may be formed using vibratory energy. A head may also be formed on the distal end of fastener 170. Fasteners 170E are shown to be bonded into the bondable material 164. Fastener 170F is shown to be bonded at the distal end and/or to bondable material 164 within the body tissue and is placed through tissue defect 166. Fasteners 170G are shown passing directly through body tissue 160, which may be fastener 170T and sleeve 171T in FIGS. 52-53 and as described below. Additional embodiments of fastener 170 are disclosed in U.S. patent application Ser. No. 12/202,210 entitled "Methods and Devices for Utilizing Thermal Energy to Bond, Stake and/or Remove Implants", which is incorporated by reference herein.

Additionally, cerclage wire 172 may be employed as known in the art, to provide further stabilization, in combination with fastener 170. For example, cerclage wire 172A may be bonded to support 168. Bondable material 164E could be used to affix cerclage wire 172A to support 168. In another example, cerclage wire 172B may be tied around support 168. Also, cerclage wire 172C may be fastened using a mechanical or bonded crimp 174. In additional example, cerclage wire 172D may be fastened to the side of support 168 or between support 168 and body tissue 160.

Figure 30:
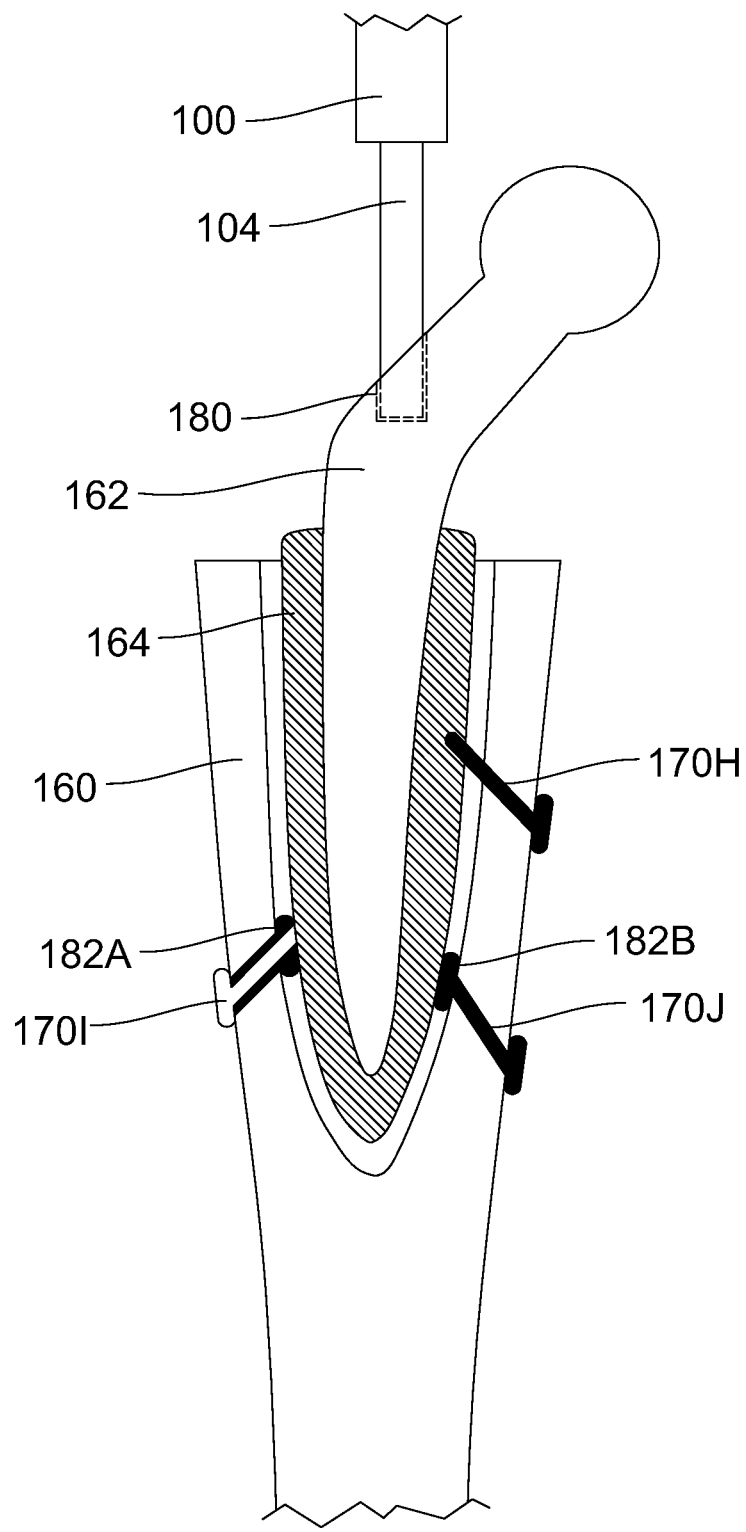
FIG. 30 illustrates alternatives for the devices and methods of FIG. 29 and illustrates a method of connecting an instrument to an implant.

Referring to FIG. 30, end effector 104 of instrument 100 may be connected into implant 162 at recess 180. This connection may be threaded, magnetic, friction, hex, ball and socket, linkage, adhesive, and other connections suitable for transferring vibratory energy as disclosed herein or known in the art. Also, other vibratory energy devices as disclosed herein or known in the art may be utilized.

FIG. 30 also shows additional methods of stabilizing a loose implant and/or facilitating the solidification and/or polymerization of bondable material 164. For example, fastener 170H may be a metal and/or polymer fastener, which may be affixed to the bondable material 164 and/or implant 162 to stabilize implant 162. In another example, fastener 170I may be metal coated with bondable material. Upon the application of vibratory energy and/or heat, distal end 182A deforms thereby stabilizing the gap between implant 162 and body tissue 160. In an additional example, fastener 170J may be made of bondable material. Upon the application of vibratory energy and/or heat, distal end 182B deforms, thereby stabilizing the gap between implant 162 and body tissue 160.

Figure 31:
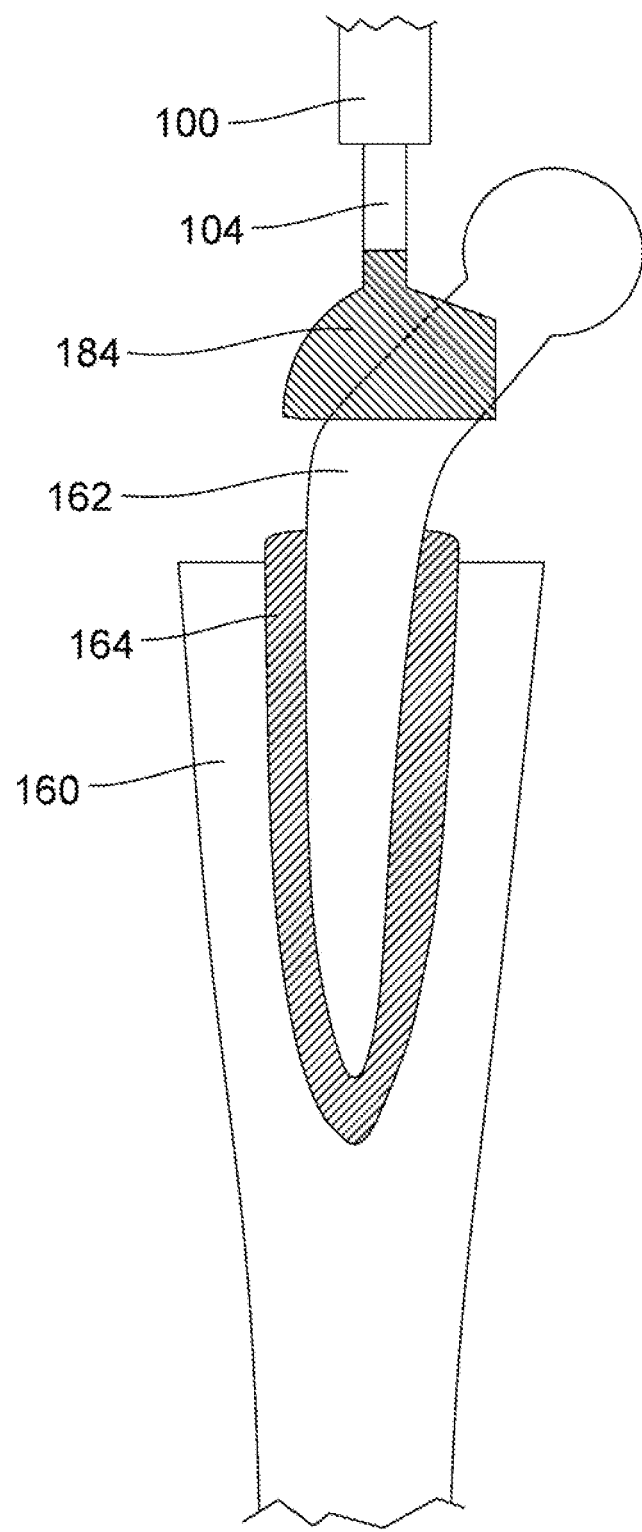
FIG. 31 illustrates an alternative method of connecting an instrument to an implant.

Referring to FIG. 31, end effector 104 of instrument 100 may be connected into implant 162 with coupler 184 to stabilize previously hardened and/or polymerized bondable material 164 or to facilitate solidification and/or polymerization of bondable material 164. This connection may be threaded, magnetic, friction, hex, ball and socket, linkage, adhesive, and other connections suitable for transferring vibratory energy as disclosed herein or known in the art. Also, other vibratory energy devices disclosed herein or known in the art may be utilized.

Figure 32:
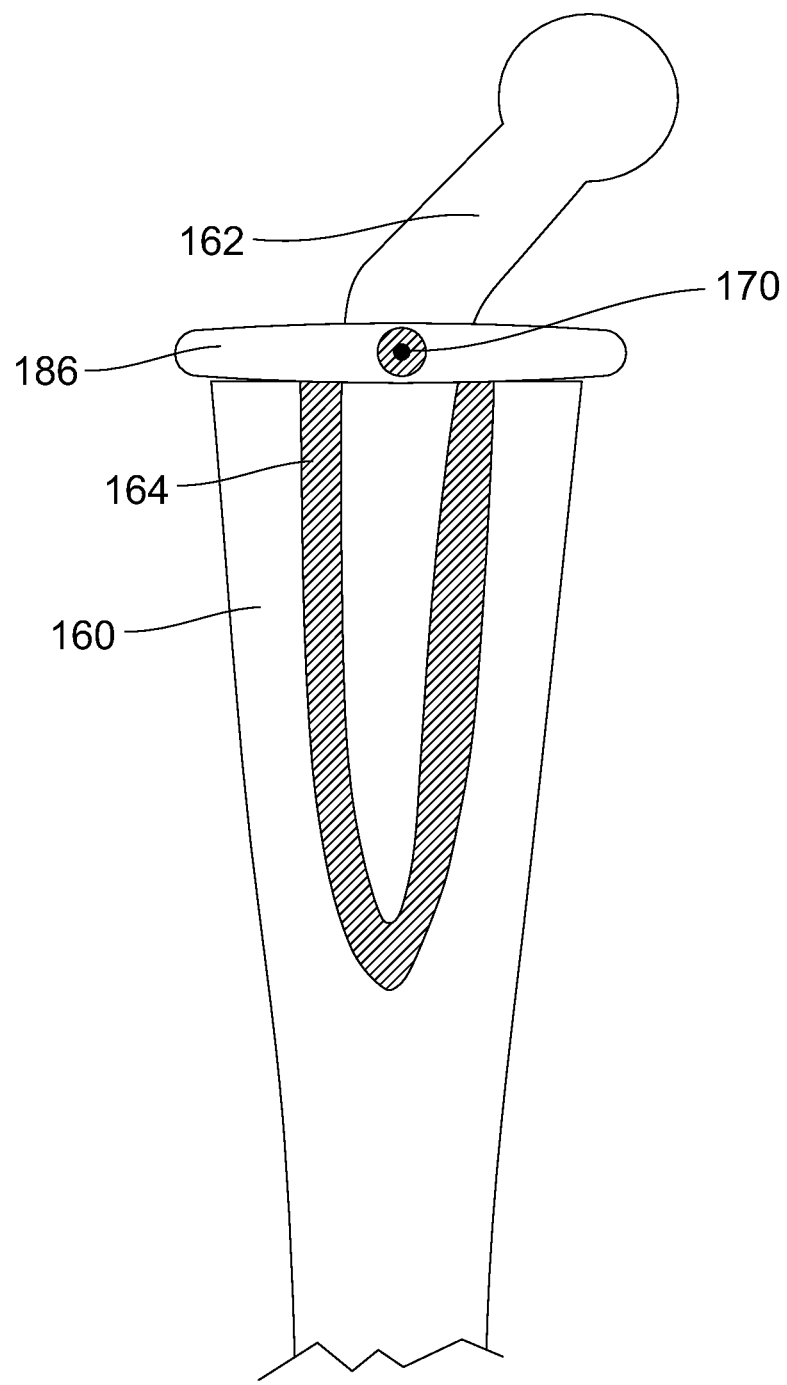
FIG. 32 illustrates the affixing an attachment to an implant.

Referring to FIG. 32, attachment 186 may be attached and/or bonded to implant 162. Attachment 186 may be made from any material described herein (i.e. collagen, graft, or growth promoter) or any other material known in the art, preferably to promote healing and/or contain bondable material 164. For example, vibratory energy may be used to bond attachment 186 to implant 162. In another example, fastener 170 may secure attachment 186 to implant 162. In an additional example, vibratory energy may be used to bond fastener 170 to attachment 186.

Figure 33:
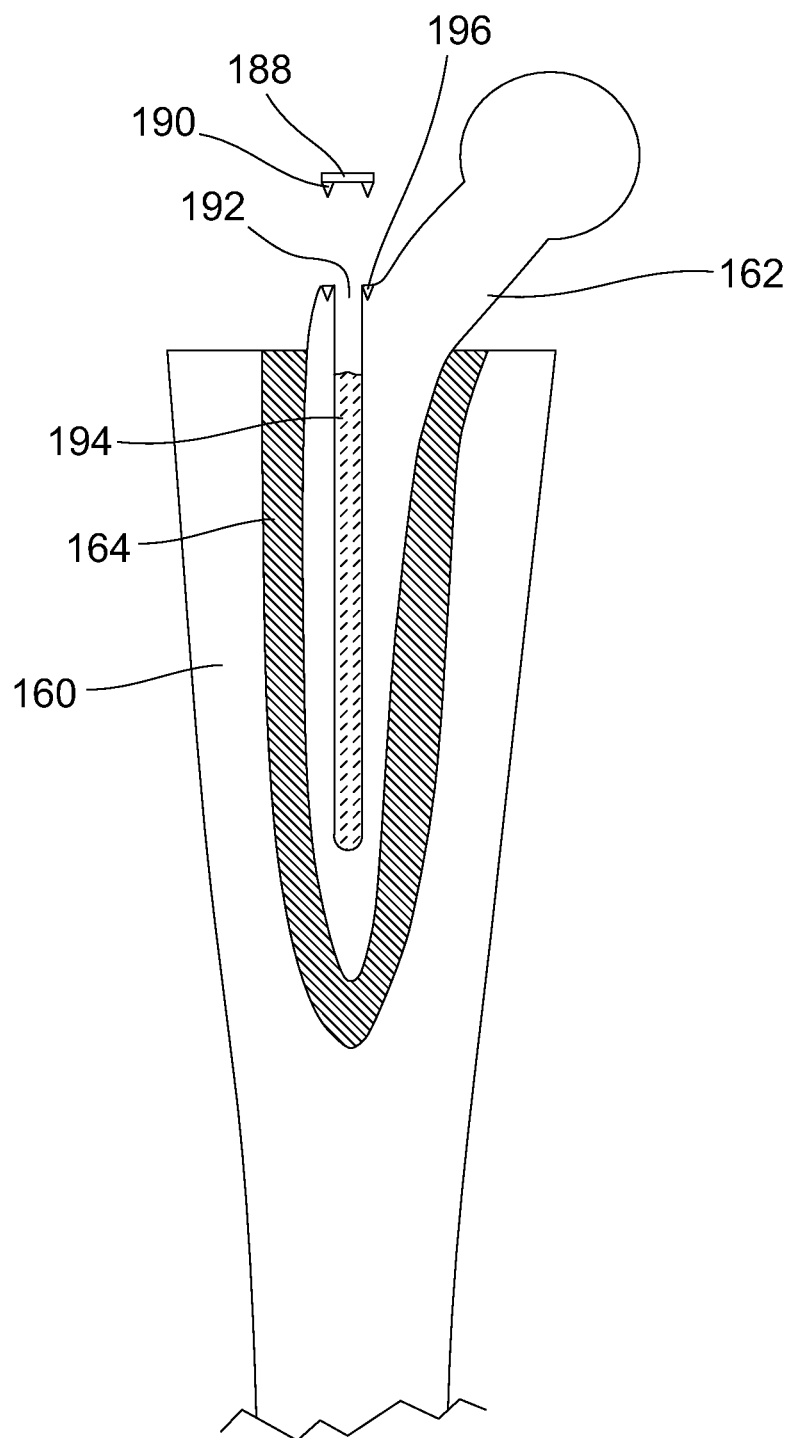
FIG. 33 illustrates the use of a reservoir.
Figure 34:
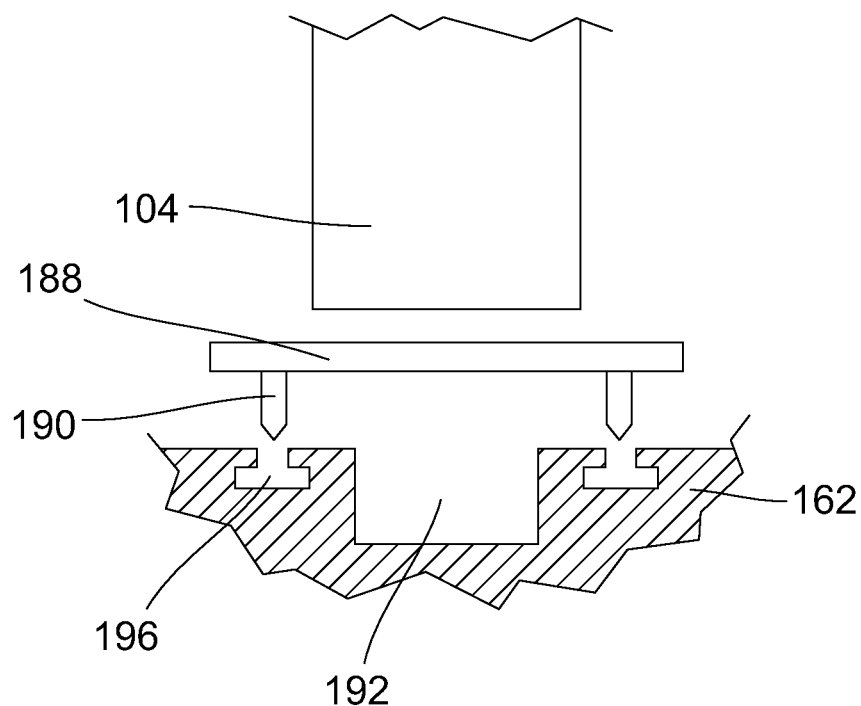
FIG. 34 illustrates an alternative configuration of FIG. 33.

Referring to FIGS. 33-34, implant 162 may be manufactured with reservoir 192 or reservoir 192 may be formed during or after implantation. Additionally, therapeutic substance 194 may be incorporated in reservoir 192 of implant 162, impregnated in implant 162, or coated on or in implant 162. As shown in FIG. 33, reservoir 192 may be located in implant 162. Alternatively, reservoir 194 may be formed in body tissue 160, as shown in FIG. 34. Cap 188 may be made of bondable material. Additionally, cap 188 may be attached and/or bonded to enclose reservoir 192. Implant 162, cap 188, and/or body tissue 160 may contain attachment feature 190 and/or attachment recess 196 to facilitate mechanical attachment and/or bonding with end effector 104. Additionally, implant 162, cap 188, and/or bondable material 164 may be porous to facilitate the delivery of therapeutic substance 194.

Figure 35:
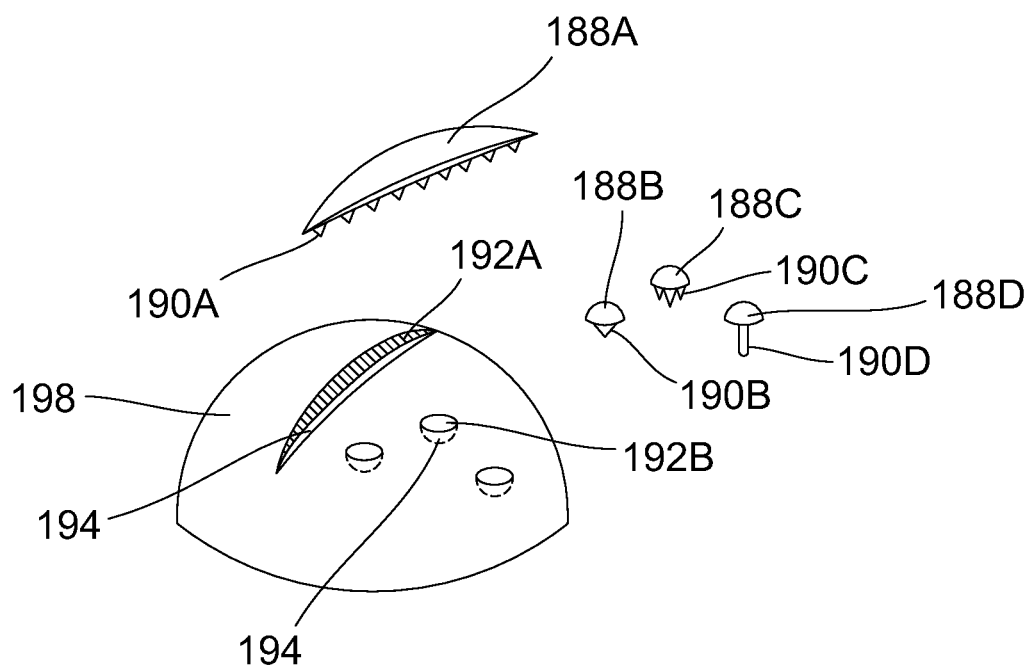
FIG. 35 illustrates alternative types of reservoirs in an alternative type of implant.

Referring to FIG. 35, therapeutic substance 194 may be contained in implant 198, for example drugs or antibiotics contained in an acetabular cup. Implant 198 may be manufactured with reservoir 192A and/or reservoir 192B or the reservoirs may be formed during implantation. Any combination of one or more reservoir 192A and/or reservoir 192 may be used. Cap 188 may be coated with bondable material. Additionally, any of caps 188A-D may be attached and/or bonded to enclose reservoir 192A or 192B, which may provide the potential benefit of multiple release times for therapeutic substance 194 Caps 188A-D may contain attachment features 190A-D to facilitate mechanical attachment and/or bonding. Additionally, implant 198 and/or any of caps 188A-D may be porous to facilitate the delivery of therapeutic substance 194.

Figure 36:
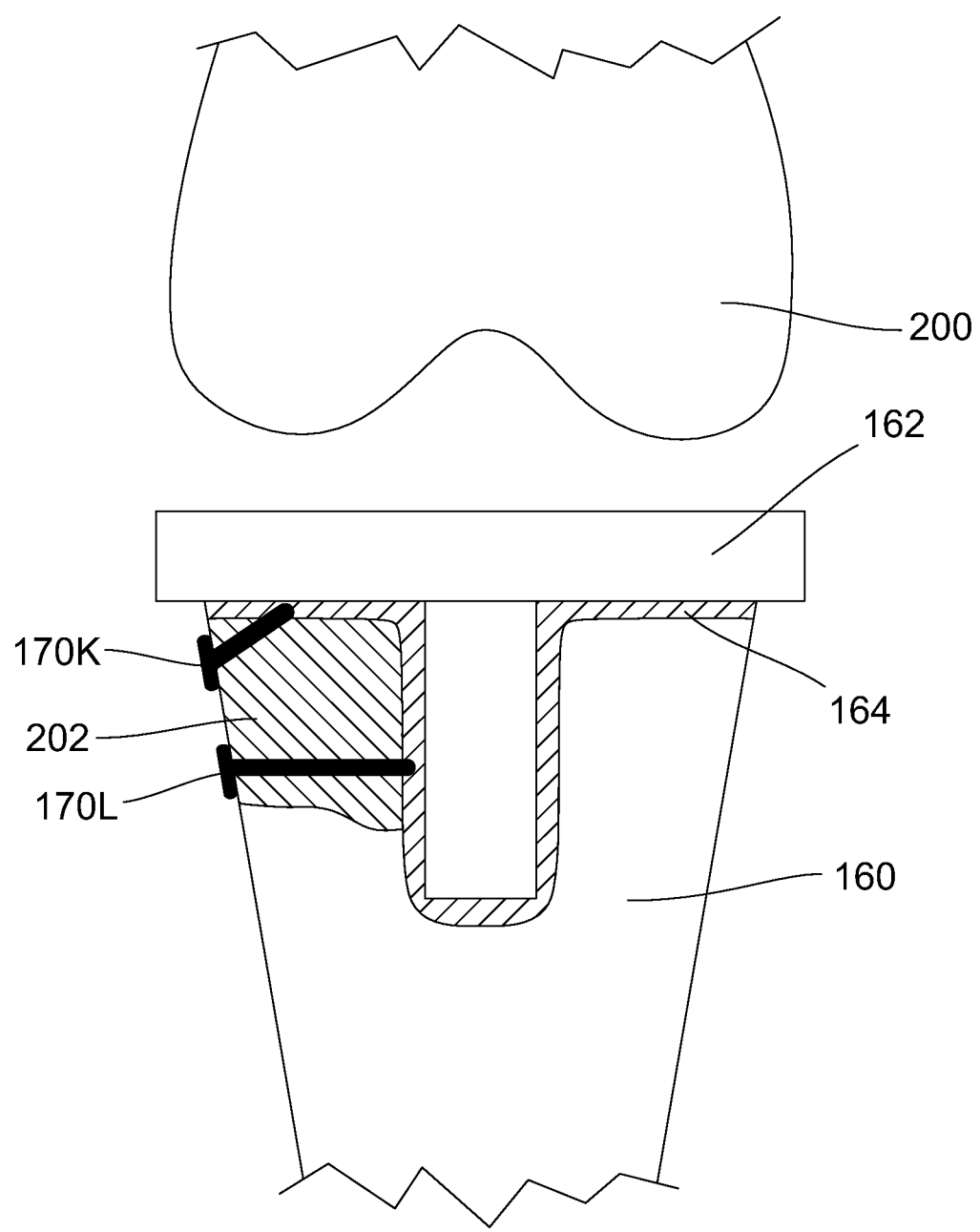
FIG. 36 illustrates an additional alternative type of implant.

Referring to FIG. 36, fastener 170 may be used to stabilize implant 162, for example a tibial component of a total knee arthroplasty (TKA). In an embodiment, fastener 170K may be bonded to bondable material 164 on the underside of the implant or bonded directly to implant 164. In another embodiment, fastener 170L may be bonded to the portion of implant 162 that is within body tissue 160. In an additional embodiment, fastener 170 may be used to secure tissue graft 202 to implant 162 and/or body tissue 160. For example, tissue graft 202 may be an allograft. Any embodiment of fastener 170 that has been described herein or known in the art may be used.

Figure 37:
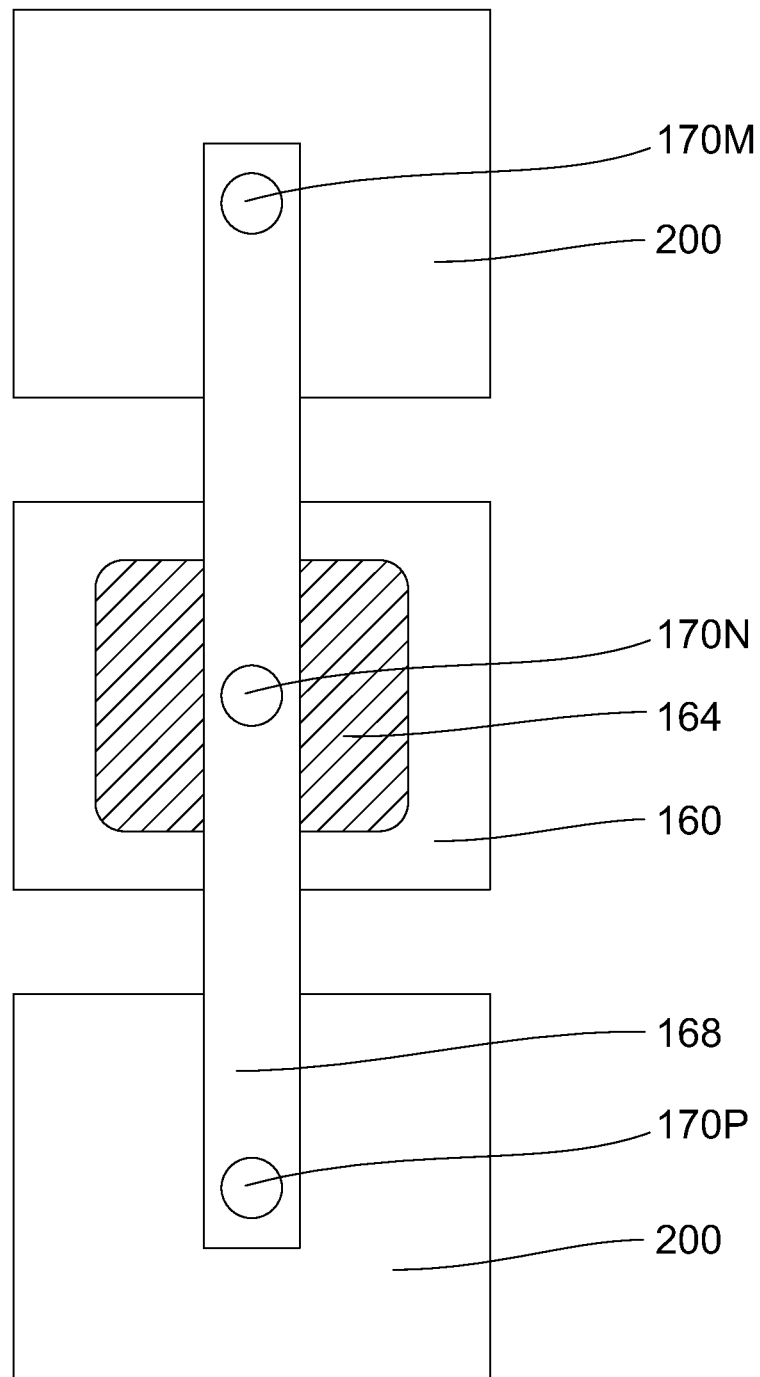
FIG. 37 illustrates fixation to previously implanted bondable material.
Figure 38:
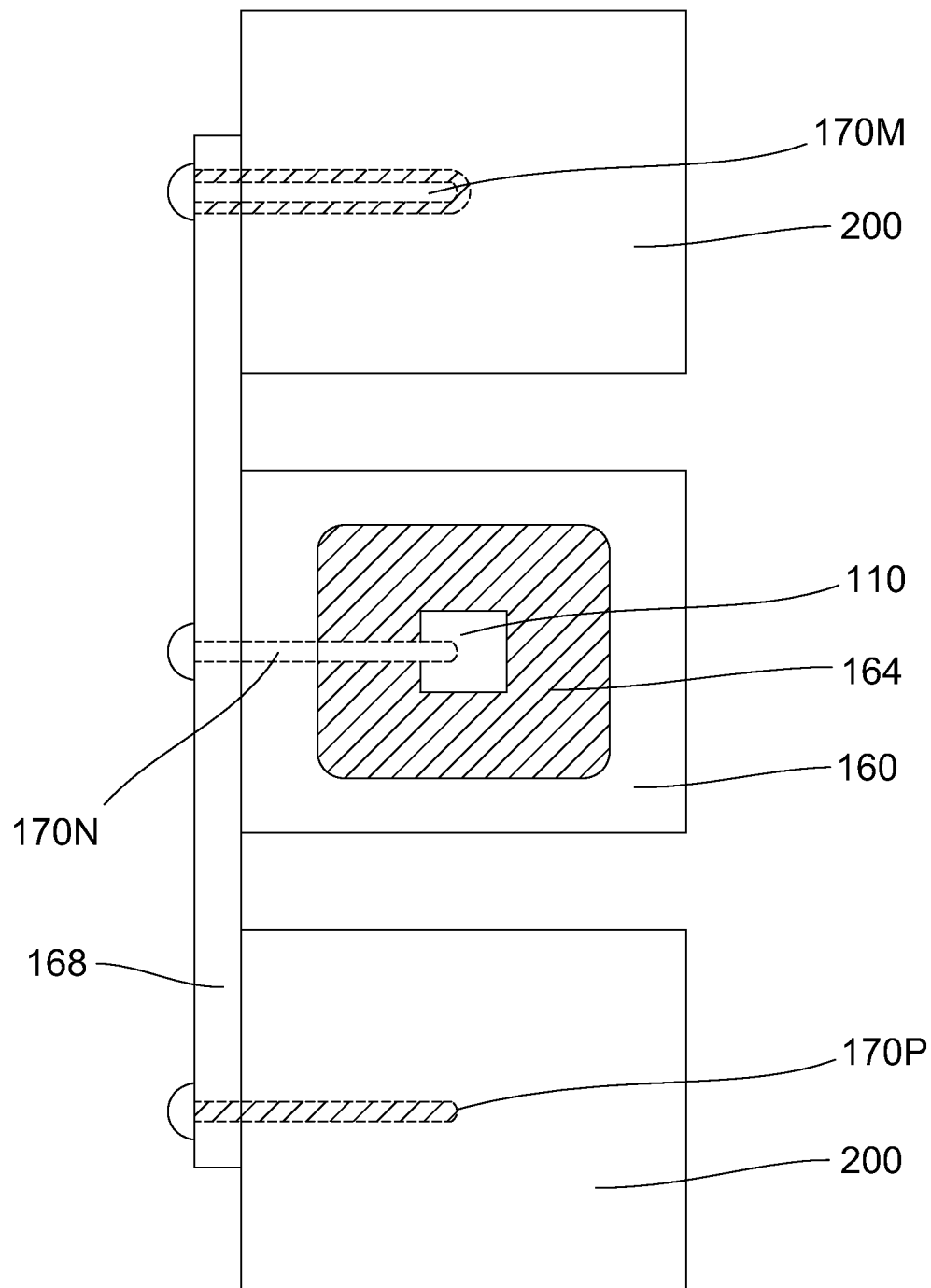
FIG. 38 illustrates an alternative view of FIG. 37.
Figure 39:
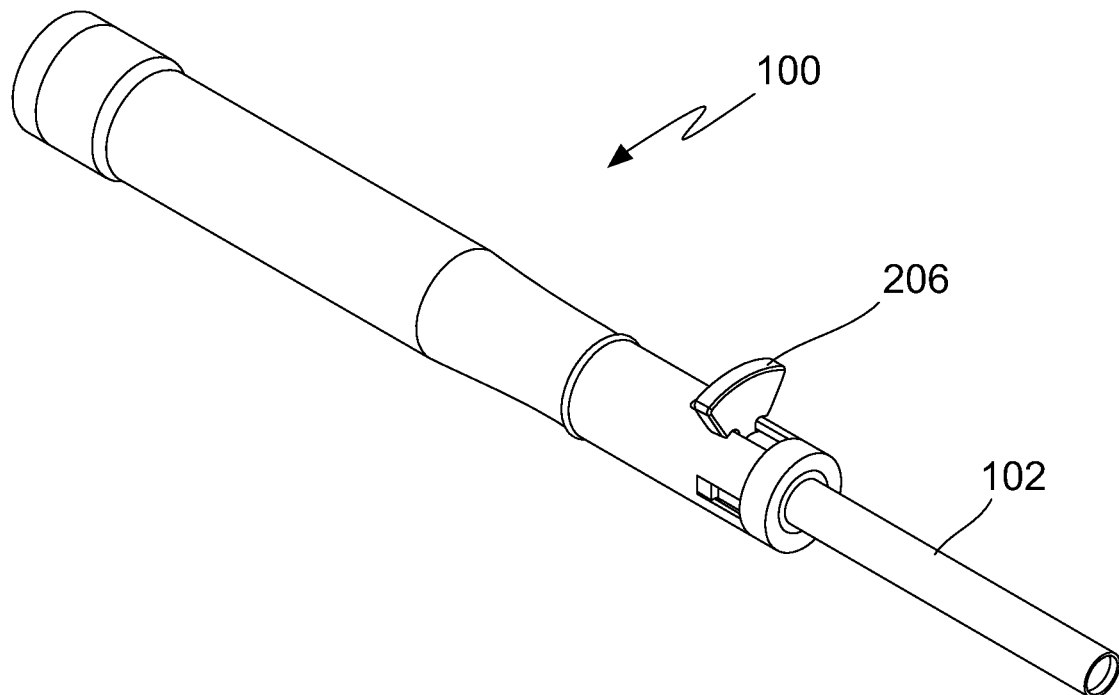
FIG. 39 illustrates an alternative configuration of the instrument of FIG. 1.
Figure 40:
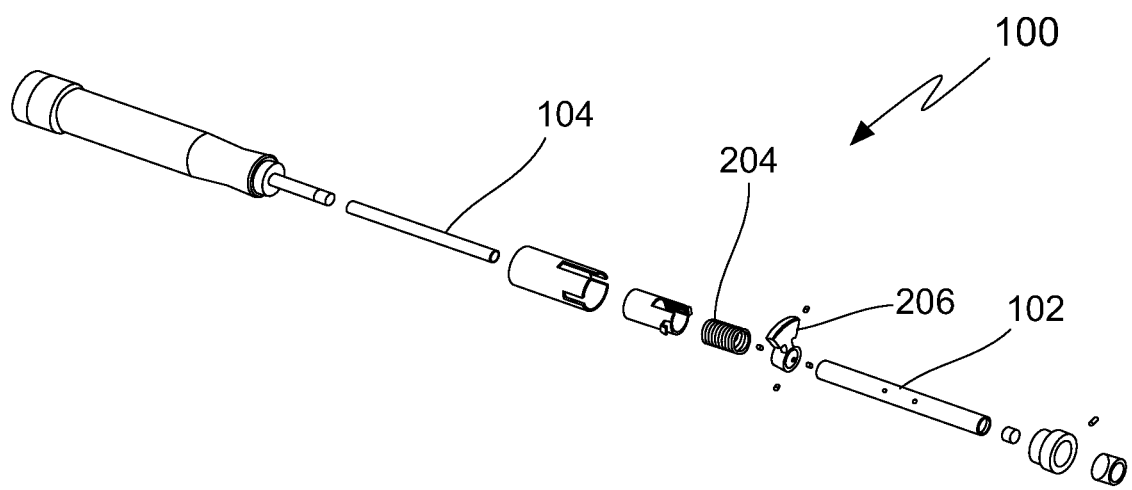
FIG. 40 illustrates an exploded view of the instrument of FIG. 39.
Figure 41:
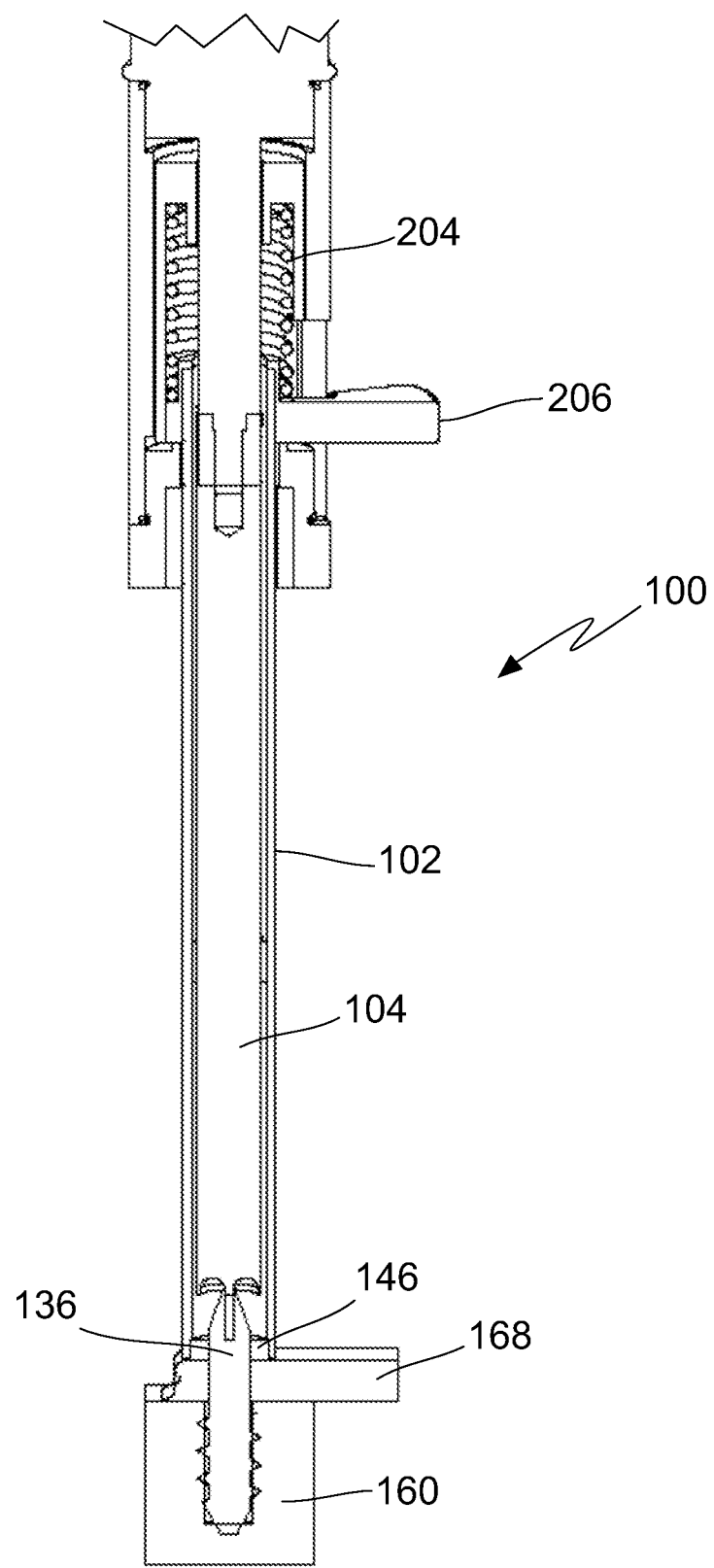
FIG. 41 illustrates a method of utilization for the instrument of FIG. 39.

Referring to FIGS. 37-38, bondable material 164 may be utilized to stabilize body tissue 160. For example, bone cement in previously performed kyphoplasty may become loose and require additional stabilization. In this example, the fasteners may utilize the previously implanted bone cement to stabilize the spine instead of removing and reapplying bone cement. In an embodiment, body tissue 160 has been previously implanted with bondable material 164. Fastener 170N is passed through support 168 and bonded to bondable material 164. As shown in FIG. 37, one or more fastener 170 is passed through support 168 and secured and/or bonded to surrounding tissue 200. Fasteners 170M, 170N, and 170P may be any embodiment disclosed herein or known in the art. Additionally, fasteners 170M, 170N, and 170P may be used with embedding fastener 110 as described above. Also in these embodiments, vibratory energy may be used to stabilize previously hardened and/or polymerized bondable material or to facilitate the solidification and/or polymerization of bondable material.

Referring to FIGS. 39-41 and 50-51, an additional embodiment of instrument 100 includes guide sheath 102, spring 204, and/or force regulator 206. In an embodiment in FIG. 41, guide sheath 102 may align washer 146 when the tip of end effector 104 is placed in contact with fastener 136. As fastener 138 is staked and the tip of fastener 136 is shaped with the application of vibratory energy, such as ultrasonic energy, guide sheath 102 may allow end effector 104 to advance while applying force to washer 146, support 168, body tissue 160, and/or bondable material 164 (not shown in FIG. 41). In a further embodiment in FIG. 41, guide sheath 102 may hold, guide, align, and/or deliver washer 146, fastener 136, or other fasteners referenced herein or known in the art. In an additional embodiment, regulating sheath 206 may have a spring 204, for example any spring, cushion, or other material or device known in the art for spring/damping applications. Additionally, instrument 100 may have regulating tab 206 for manually applying and/or regulating the movement of guide sheath 102. Although the embodiment in FIG. 41 may be used under a limitless number of configurations and settings, Table 2 is being set forth with operative examples:

TABLE 2

Polycarbonate Fastener Bonding
Instrument: Handpiece P05 with tuning of 39,000-45,000 Hz
System Settings: 39,500 Hz, SOW, 1.0 sec weld time

| Test Sample Number | Power (watts) | Energy Application Time (sec) | Force Applied to Break (lbs.) | Deformation Depth (inches) |
|---|---|---|---|---|
| 1 | 30 | 1.69 | 93.2 | 0.115 |
| 2 | 28 | 1.68 | 86.4 | 0.110 |
| 3 | 31 | 1.78 | 98.2 | 0.111 |
| 4 | 27 | 1.80 | 91.3 | 0.108 |
| 5 | 31 | 1.69 | 109.2 | 0.109 |

In additional embodiments, frequency may preferably be between 20 to 80 khz, power may preferably be between 5 to 200 watts, and energy application time may be preferably between from 0.1 to 5 seconds.

In an embodiment, a sensor may be included in instrument 100. For example, a force, pressure, or temperature sensor may be used to measure bonding and/or staking. In another example, a visual and/or audio indicator may be operatively connected to the sensor, which may be used to indicate a proper bond/stake. In another embodiment, a visual and/or audio indicator may be connected to instrument 100 or the energy generator, which may be used to illustrate and/or teach proper technique during bonding and/or surgery. In another example, the visual and/or audio indicator may indicate completion of a proper bond/stake, over/under application of force, or expiration of desired energy application time.

In another embodiment, a vacuum may be operatively connected to 100. For example, the vacuum may be communicatively connected between the guide sheath 102 and end effector 104, which may be used for the removal of debris from instrument 100.

Figure 42:
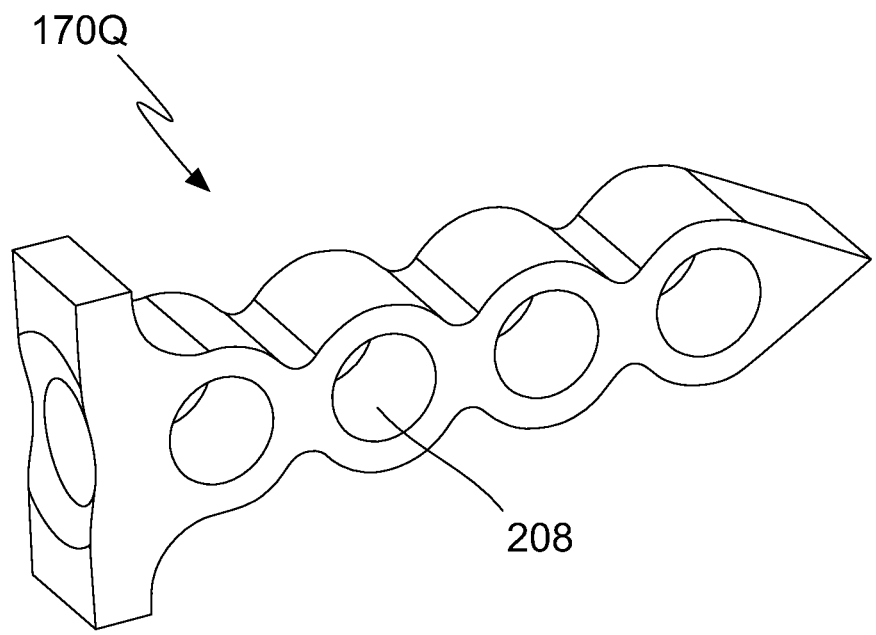
FIG. 42 illustrates an alternative configuration of a fastening implant.
Figure 43:
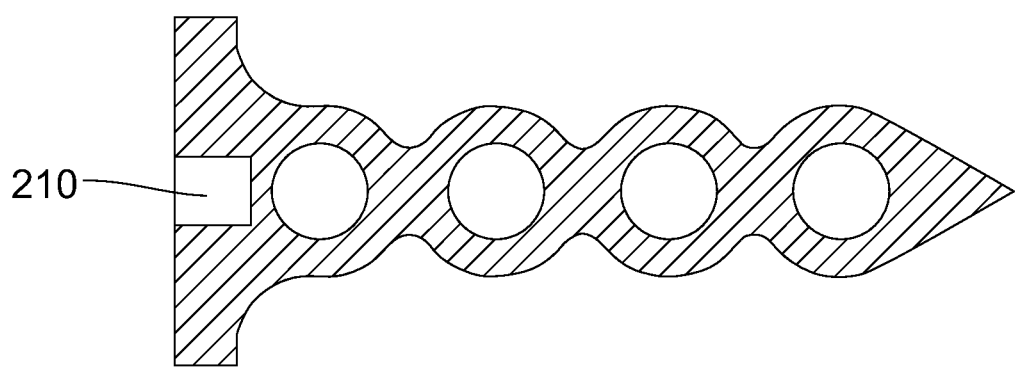
FIG. 43 illustrates an alternative view of FIG. 42.

Referring to FIGS. 42-43, an additional embodiment of fastener 170 may include one or more feature 208. Feature 208 may increase or decrease the transfer of energy across fastener 170. Feature 208 may pass into the surface or through fastener 170. Feature 208 may be on any surface or surfaces of fastener 170 and/or contain therapeutic substances. Fastener 170 may include effector interface 210, preferably for engagement with end effector 104.

Figure 44:
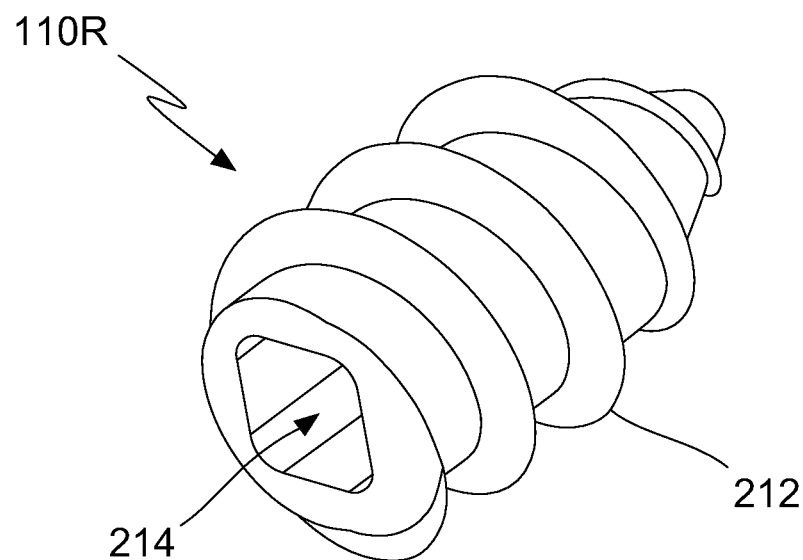
FIG. 44 illustrates an alternative configuration of an embedding implant.
Figure 45:
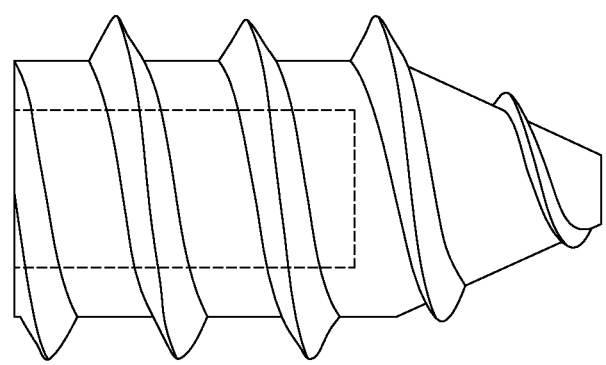
FIG. 45 illustrates an alternative view of FIG. 44.

Referring to FIGS. 44-45, embedding fastener 110 may also include thread 212. Embedding fastener 110 may be screwed and/or engaged into bondable material, tissue, and/or any other material disclosed herein, preferably by engaging interface 214 with a screw driver or other tool. Embedding fastener 110 may include an interface 214 which may be radiused, chamfered, funnel-shaped, threaded, or any other shape, for example square, rectangular, circular, elliptical, triangular, hexagonal, or asymmetrical shape. Embedding fastener 110 may be made of any metal, polymer, or other material disclosed herein.

Figure 46:
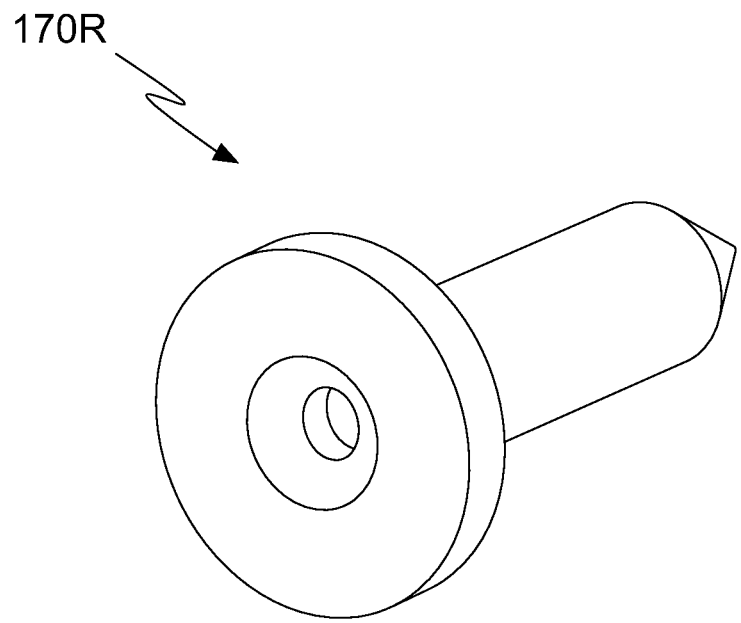
FIG. 46 illustrates an alternative configuration of a fastening implant.
Figure 47:
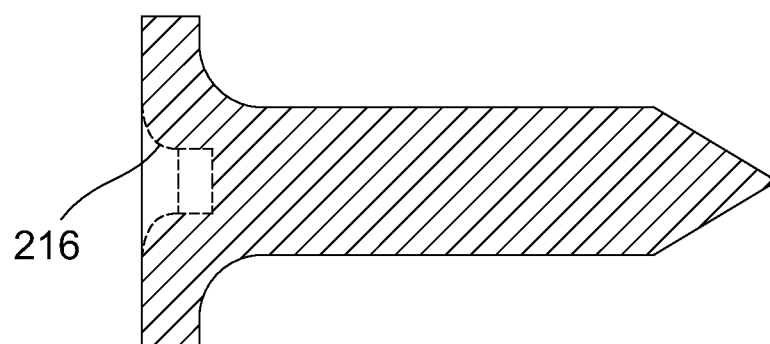
FIG. 47 illustrates an alternative view of FIG. 46.

Referring to FIGS. 46-47, fastener 170 may include effector interface 216. Preferably for engagement with end effector 104, effector interface 216 may be radiused, chamfered, funnel-shaped, threaded, or any other shape, for example square, rectangular, circular, elliptical, triangular, hexagonal, or asymmetrical shape.

Figure 48:
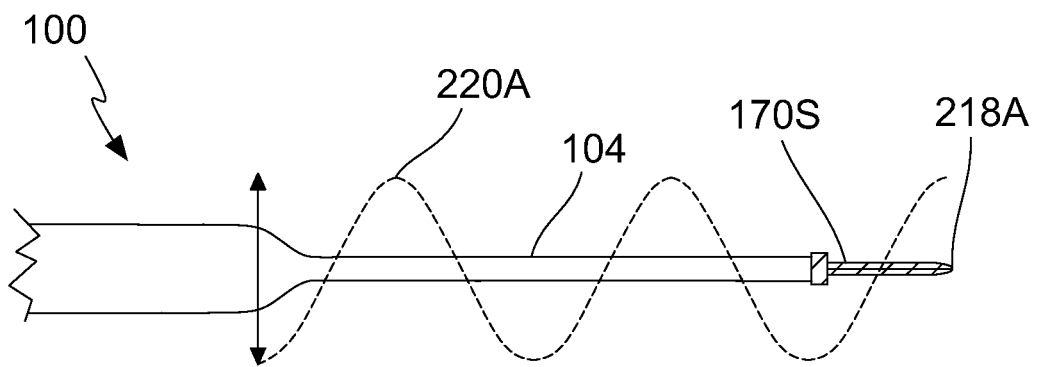
FIG. 48 illustrates an energy signal through an end effector and implant.
Figure 49:
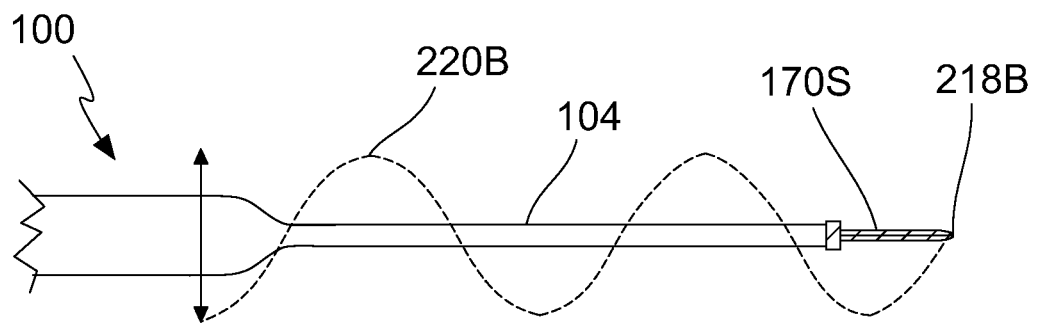
FIG. 49 illustrates an alternative configuration of an energy signal through an end effector and implant.
Figures 50, 51:
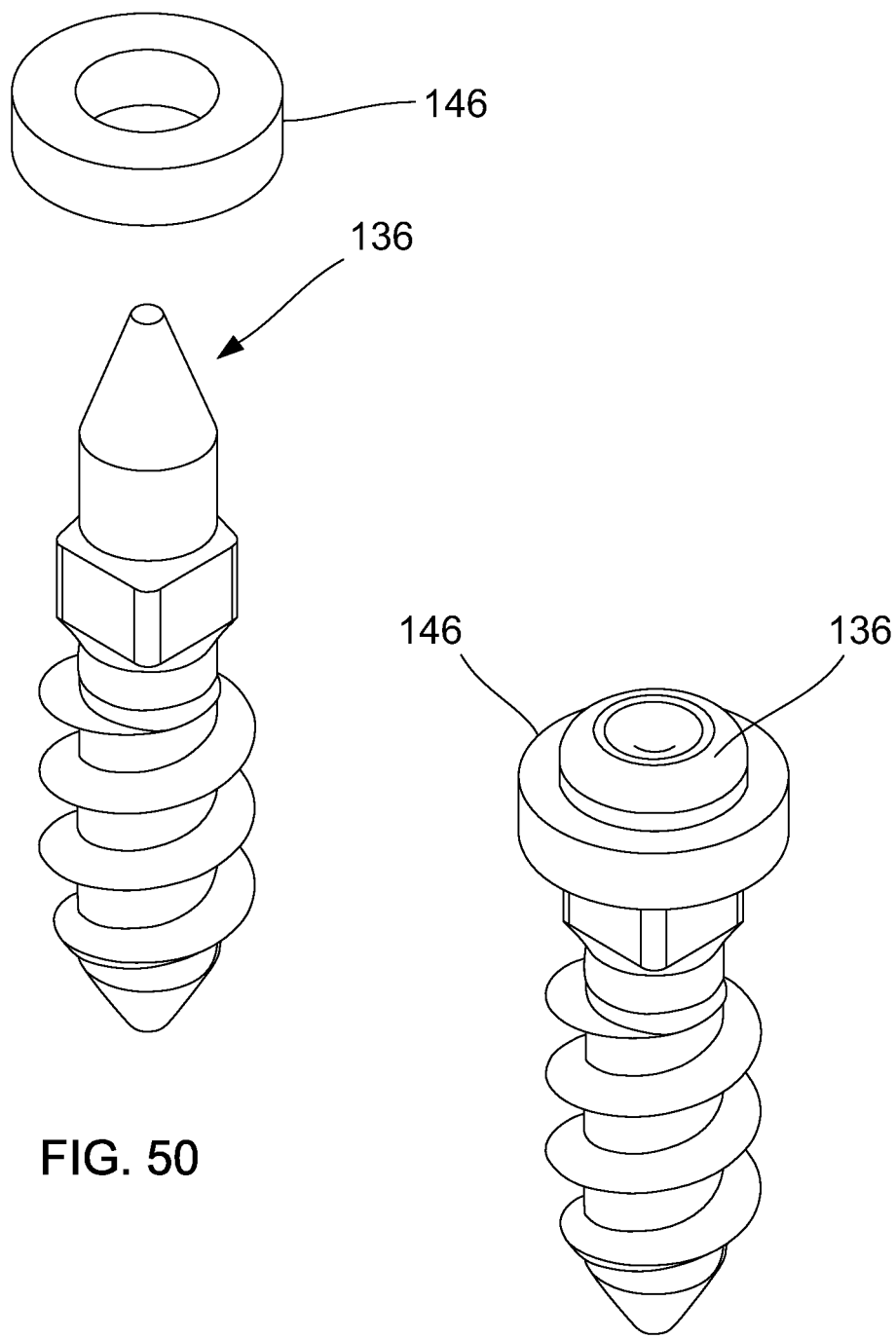
FIG. 50 illustrates an exploded view of the fastening implant of FIG. 41.
FIG. 51 illustrates the fastening implant of FIG. 50 after staking.

Referring to FIGS. 48-49, instrument 100 may include end effector 104 dimensioned and configured for a point of maximum displacement at or near the middle of fastener 170 at or near point 218B (FIG. 49). In another embodiment, it may be preferable for instrument 100 to include end effector 104 dimensioned and configured for a point of maximum displacement at or near the end of fastener 170 at or near point 218A (FIG. 48). For most applications, a point of maximum displacement at or near point 218B is preferred. Fastener 170 may be threaded or have an interference fit with end effector 104.

A point of maximum displacement along end effector 104 may occur at increments of about half its wavelength, which may be determined by the ratio of the speed of sound through the material of end effector 104 to the frequency of the wave propagated through end effector 104. The end effector 104 may be made of titanium or any material disclosed herein. For example, at a frequency of 20 khz, points of maximum displacement along end effector 104 made of titanium may be in increments of about 4 to 6 inches, preferably 4.8 to 5.1 inches. For example, at a frequency of 40 khz, points of maximum displacement along end effector 104 made of titanium may be in increments of about 2 to 3 inches, preferably 2.4 to 2.5 inches A point of maximum displacement along fastener 170 may also occur at increments of about half its wavelength. Fastener 170 may be made of PEEK, PLLA, or any material disclosed herein. As an example for PEEK, at a frequency of 20 khz, points of maximum displacement along end effector 104 may be in increments of about 1 to 2 inches, preferably 1.6 to 1.7 inches. As another example for PEEK, at a frequency of 40 khz, points of maximum displacement along end effector 104 may be in increments of about 0.5 to 1 inch, preferably 0.8 inches. As an example for PLLA, as an example at a frequency of 20 khz, points of maximum displacement along end effector 104 may be in increments of about 1 to 2 inches, preferably 1.3 to 1.4 inches. As an example for PLLA, as an example at a frequency of 40 khz, points of maximum displacement along end effector 104 may be in increments of about 0.5 to 1 inch, preferably 0.7 inches.

To optimize bonding and/or reduce the stress applied, the desired point of bonding on fastener 170 should be at or near a point of maximum displacement. For example, the desired point of bonding on fastener 170 may be along half its length or at its tip (see 218A of FIG. 48). If the desired point of bonding is at a point of minimal or zero displacement (see 218B of FIG. 49), bonding may be difficult. To facilitate bonding, it may be preferable to increase power or amplitude of the signal, thereby increasing energy applied to fastener 170.

Figure 52:
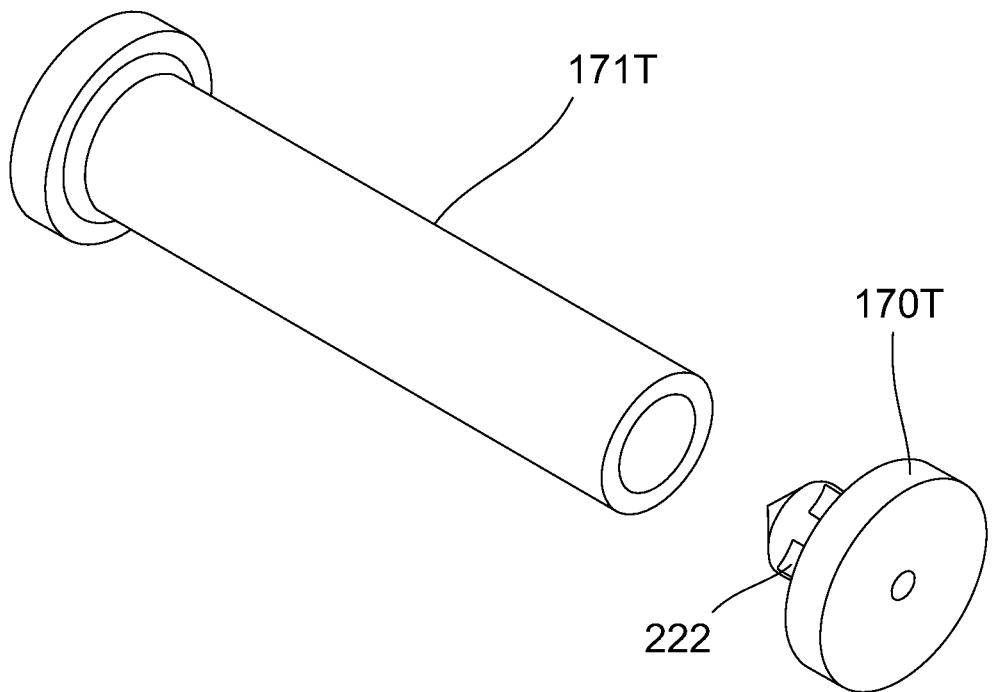
FIG. 52 illustrates an exploded view of an alternative type of fastening implant.
Figure 53:
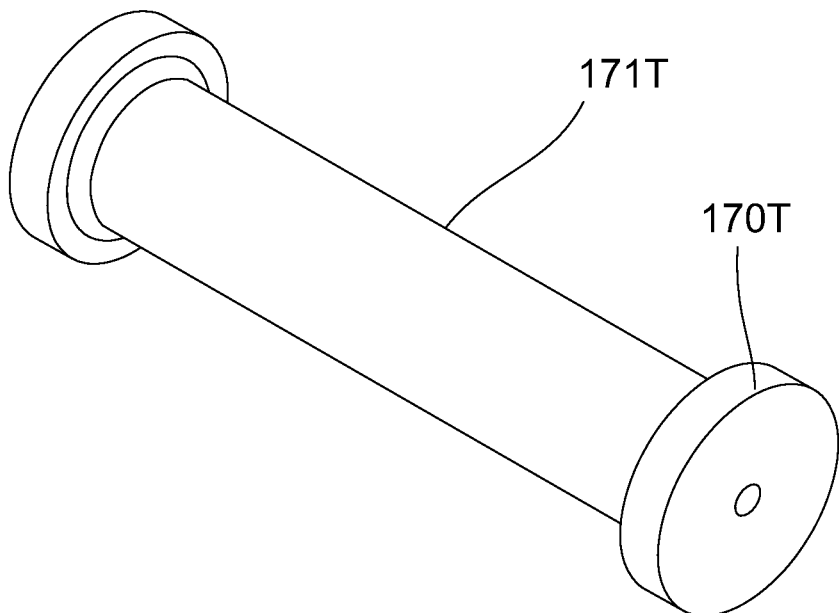
FIG. 53 illustrates an alternative view of FIG. 52.

Referring to FIGS. 52-53, fastener 170T may be used with sleeve 171T, potentially to contain and/or release therapeutic substances into a body. Fastener 170T may engage with sleeve 171T by mechanical interlock, thread, or vibratory energy bond. End effector 104 may engage with fastener 170T for vibratory energy bonding. Any fastener 170 disclosed herein may have energy director 222 to facilitate bonding by directing energy to the desired location of bonding.

Figure 54:
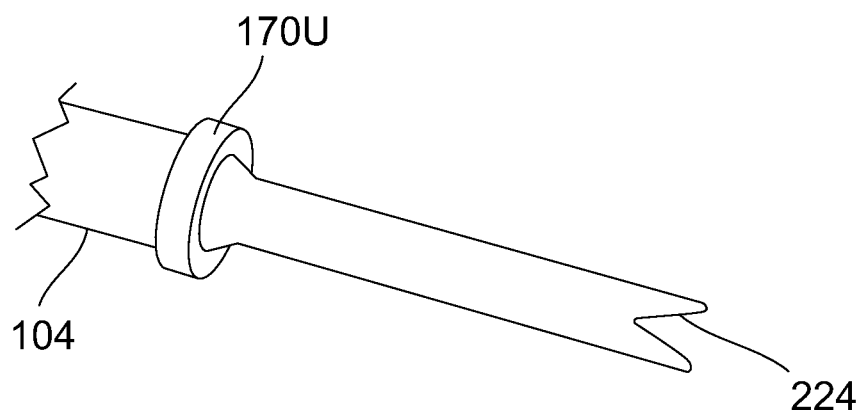
FIG. 54 illustrates an alternative configuration of a fastening implant.
Figure 55:
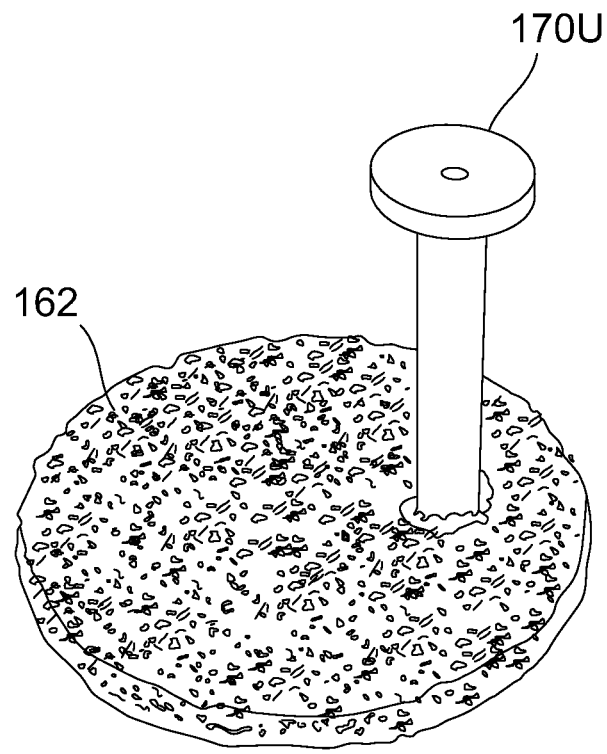
FIG. 55 illustrates the fastening implant of FIG. 54 bonded to another implant.

Referring to FIGS. 54-55, fastener 170U may have energy director 224. Energy director 224 may facilitate bonding with implant 162, especially if a portion or the entirety of implant 162 includes a porous material. For example, implant 162 may include a porous metal. End effector 104 may engage with fastener 170U for vibratory energy bonding.

Figure 56:
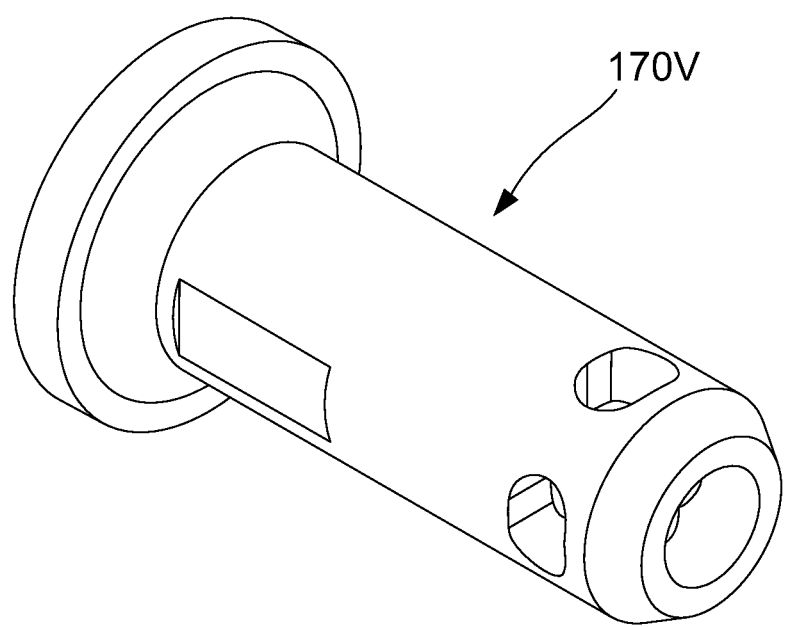
FIG. 56 illustrates an alternative configuration of a fastening implant or embedding implant.

Referring to FIG. 56, fastener 170F may be embedded into a bondable material with its leading end and stabilize a support 168 (i.e. plate) with its trailing end. End effector 104 may engage with fastener 170F, preferably near the trailing end, for vibratory energy bonding. Fastener 170F may include any material disclosed herein, but preferably titanium or titanium with at least a portion coated with PEEK or PLLA.

Figure 57:
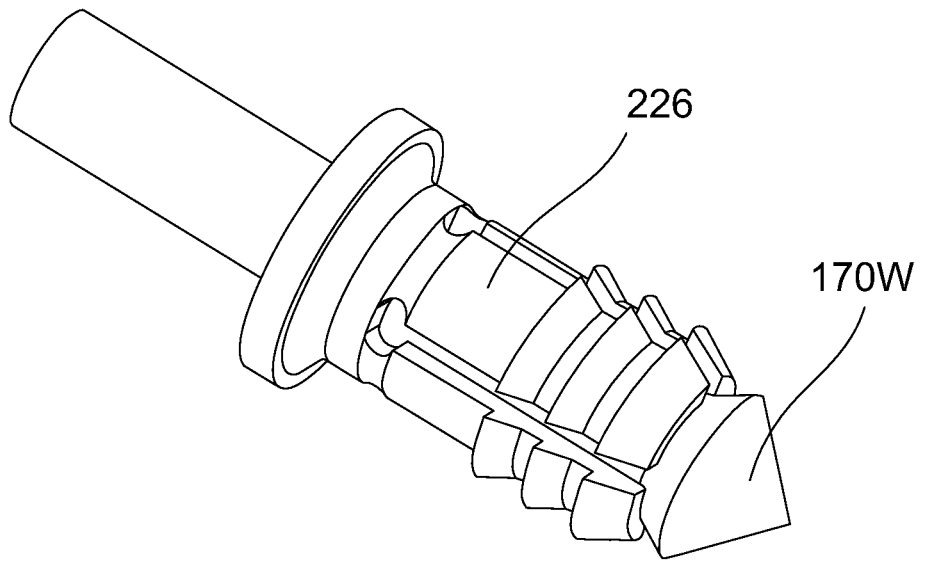
FIG. 57 illustrates an expandable configuration of a fastening implant and expanding implant.
Figure 58:
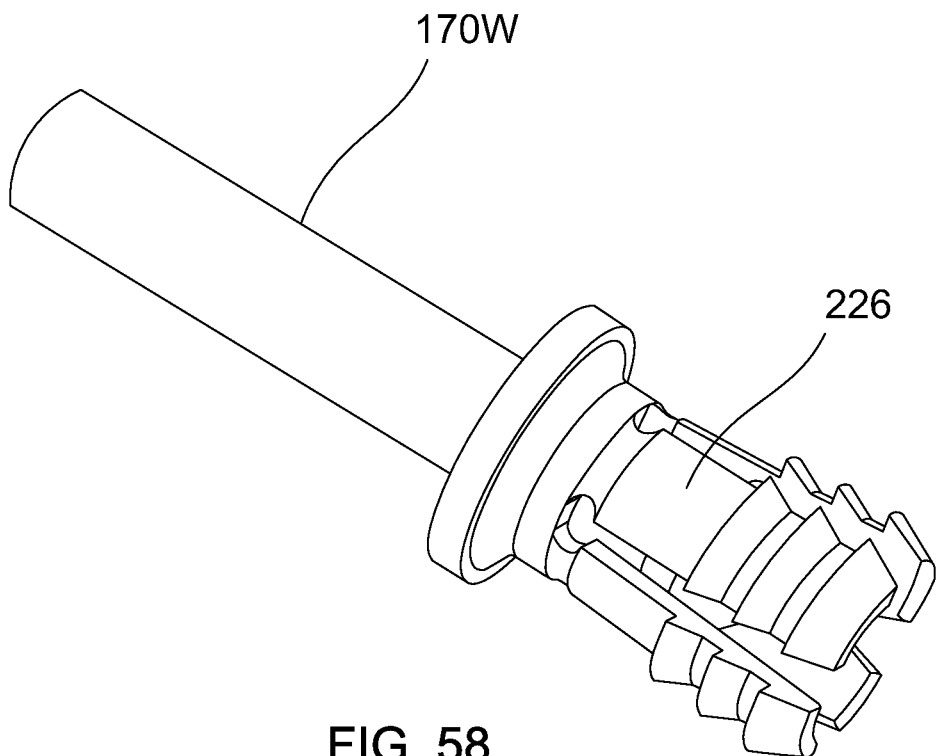
FIG. 58 illustrates an alternative view of FIG. 57.

Referring to FIGS. 57-58, fastener 170W may be used with, preferably disposed within, expanding anchor 226. End effector 104 may engage with fastener 170W, preferably near the trailing end, for vibratory energy bonding. A hole in tissue and/or bondable material may be formed or drilled into body tissue 160 prior to or during the implantation of fastener 170W and expanding anchor 226. Fastener 170W and expanding anchor 226 may pass into body tissue 160, for example in the configuration shown in FIG. 57. Fastener 170W may be retracted into expanding anchor 226, preferably after being positioned in body tissue 160. Expanding anchor 226 may expand outwards (shown in FIG. 58), thereby engaging and/or exerting a radially outward force on body tissue 160. Preferably after fastener 170W and expanding anchor 226 are in an expanded condition, vibratory energy may be applied to fastener 170W, preferably near the trailing end, to bond fastener 170W and expanding anchor 226 together. In another embodiment, fastener 170W and/or expanding anchor 226 may be configured to bond into a bondable material. After fastener 170W and expanding anchor 226 have been stabilized in the expanded configuration, the excess length of the trailing end of fastener 170W may be removed to be substantially flush with the trailing end of expanding anchor 226.

Figure 59:
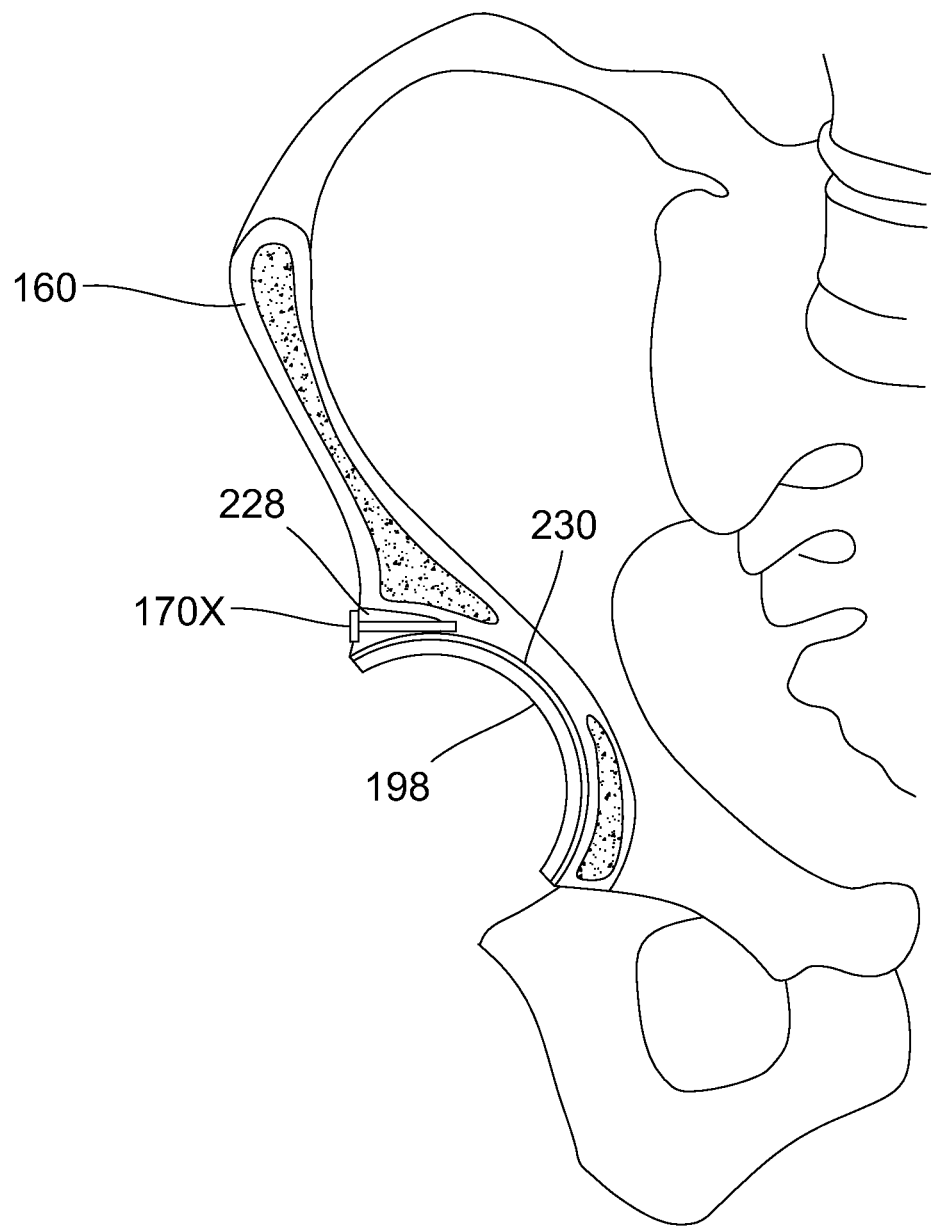
FIG. 59 illustrates an alternative configuration of an implant, interference implant, and fastening implant.

Referring to FIG. 59, fastener 170 may be used to increase interference between body tissue 160 and implant 198. Fastener 170 may be an interference screw and/or used in conjunction with interference implant 228 to position and/or stabilize implant 198. Fastener 170 may pass through all or a portion of implant 198. In additional embodiments, fastener 170 may stabilize body tissue 160 (i.e. ACL graft) against the side of a hole in body tissue 160 (i.e. bone) (not shown), stabilize body tissue 160 (i.e. soft tissue) to another body tissue 160 (i.e. bone), or stabilize interference implant 228 (or tissue graft 202) to body tissue 160 (i.e. bone) and/or implant 198 (FIG. 59). In another embodiment, fastener 170 may be part or entirely made of a biodegradable and/or bondable material. In an embodiment, fastener 170 may have a snap that would overlay part of implant 198 for interference. In another embodiment, implant 198 may include porous surface 230 (FIG. 59) or a coating of bondable material. In another example, implant 198 may be bonded with vibratory energy, hydrophilic, and/or mechanically expandable against body tissue 160 (i.e. bone), which may allow the implant to sequentially expand and provide interference against body tissue 160 (i.e. bone) or another implant.

In an embodiment related to hip (or shoulder) resurfacing, implant 198 may be an acetabular component or cup (or glenoid component), which is commonly stabilized using screws through its center. To replace the use of these screws or to provide additional stabilization, implant 198 may be stabilized by positioning fastener 170 between implant 198 and body tissue 160 (i.e. acetabulum or glenoid), which may urge implant 198 to the desired position and/or enhance interference with body tissue 160. In an embodiment, implant 198 may be free of holes, as fastener 170 may provide the majority of interference.

There are many different features to the present invention and its contemplated that these features may be used together or separately. Thus, the invention should not be limited to any particular combination of features or to a particular application of the invention. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention.

The following is claimed:

1. A method of utilizing a bondable material to secure a fastener, said method comprising:

engaging an end effector with at least a trailing end of the fastener;

positioning a leading end feature of the fastener in direct contact with a surface of the bondable material, wherein the bondable material is in a fixed position;

applying energy to the fastener to heat and melt at least a portion of the bondable material in contact with the leading end feature of the fastener;

applying force to the fastener during the application of energy to the fastener to form an opening through the surface of the bondable material and embed at least a portion of the fastener within the bondable material to secure the fastener within the bondable material; and disengaging the end effector from the trailing end of the fastener.

2. The method of claim 1 further comprising retaining force on the fastener after the application of energy to allow the bondable material to cool and harden.

3. The method of claim 1 wherein at least a portion of the fastener is mechanically interlocked within the bondable material.

4. The method of claim 1 wherein the bondable material is a solidified polymer before the application of energy.

5. The method of claim 1 wherein at least a portion of the bondable material flows into at least one surface feature of the fastener to secure the the fastener to the bondable material.

6. The method of claim 1 wherein leading end feature of the fastener is a taper.

7. The method of claim 1 wherein at least a portion of the fastener comprises at least one of titanium, stainless steel, and cobalt-chrome alloy.

8. The method of claim 1 wherein the fastener is internally threaded.

9. The method of claim 8 further comprising securing a second fastener having external threads to the fastener embedded in the bondable material.

10. The method of claim 1 wherein the fastener includes at least a portion of titanium and at least a portion of a polymer.

11. The method of claim 1 wherein the energy is at least one of vibratory energy, ultrasonic energy, radiofrequency energy, microwave energy, laser energy, electromagnetic energy, and resistive heating.

12. The method of claim 1 wherein the fastener remains solid when embedded within the bondable material.

13. The method of claim 1 wherein the bondable material is bone cement.

14. The method of claim 1 wherein the fastening implant is positioned relative to a supporting element.

15. A method of securing a fastener in a bondable material, said method comprising:

positioning a leading end of a fastener in direct contact with a portion of the bondable material, wherein the bondable material is in a fixed position;

applying ultrasonic energy to the fastener to melt the portion of the bondable material in contact with the leading end of the fastener; and applying force to the fastener during the application of energy to the fastener to form an opening in the bondable material and embed at least a portion of the fastener within the bondable material.

16. The method of claim 15 wherein the fastener is mechanically interlocked within the bondable material.

17. The method of claim 15 further comprising retaining force on the fastener after the application of ultrasonic energy to allow the bondable material to cool and harden.

18. The method of claim 15 wherein the fastener is internally threaded.

19. The method of claim 18 further comprising securing a second fastener having external threads to the fastener embedded in the bondable.

20. The method of claim 15 wherein the fastener is engaged with an end effector prior to the application of ultrasonic energy and the end effector is disengaged from the fastener after the fastener is embedded within in a hole in the bondable material.

\* \* \* \* \*